(12) United States Patent
Shmilovich et al.

(10) Patent No.: US 10,350,593 B2
(45) Date of Patent: Jul. 16, 2019

(54) CHIP DEVICE FOR MONITORING AND REGULATING FLUID FLOW, AND METHODS OF MANUFACTURE THEREOF

(71) Applicant: EZMEMS LTD., Kfar Saba (IL)

(72) Inventors: Tsvi Shmilovich, Pardes Hanna-Karkur (IL); Nicola Molinazzi, Kfar Saba (IL)

(73) Assignee: EZMEMS LTD., Kfar Saba (IL)

(*) Notice: Subject to any disclaimer, the term of this patent is extended or adjusted under 35 U.S.C. 154(b) by 31 days.

(21) Appl. No.: 15/227,278

(22) Filed: Aug. 3, 2016

(65) Prior Publication Data
US 2016/0339431 A1 Nov. 24, 2016

Related U.S. Application Data

(63) Continuation-in-part of application No. PCT/IL2015/050111, filed on Feb. 1, 2015.
(Continued)

(51) Int. Cl.
*B01L 3/00* (2006.01)
*G01N 35/00* (2006.01)
(Continued)

(52) U.S. Cl.
CPC ... *B01L 3/502715* (2013.01); *A61M 5/16804* (2013.01); *A61M 5/16877* (2013.01);
(Continued)

(58) Field of Classification Search
CPC ........ G01N 31/16; G01N 35/00; G01N 27/00; B01L 3/00; B01L 3/02; H05B 6/00
(Continued)

(56) References Cited

U.S. PATENT DOCUMENTS 4,227,151 A 10/1980 Ellis et al.
6,857,449 B1 2/2005 Chow
(Continued)

FOREIGN PATENT DOCUMENTS

CN 102741979 10/2012
CN 103185612 7/2013
(Continued)

OTHER PUBLICATIONS

Engel, et al., Multi-Layer Embedment of Conductive and Non-Conductive PDMS for All-Elastomer MEMS, Proceedings IEEE MEMS, 2016, pp. 246-250.
(Continued)

*Primary Examiner* — Brian J. Sines
(74) *Attorney, Agent, or Firm* — Browdy and Neimark, P.L.L.C.

(57) ABSTRACT

A device for monitoring fluid media, and methods of manufacture thereof are disclosed. The monitoring device may be implemented as a single monolithic unit made from a certain type of material without a separate packaging, and having a base element comprising at least one fluid port and at least one cavity or fluid flow path fluidly coupled to the at least one fluid port for enabling fluid exchange of fluid media therewith. The device comprises at least one sensing element associated with the cavity or fluid flow path and configured and operable for measuring at least one property or condition of fluid media introduced thereinto, and generate measurement data or signals indicative thereof. Electrical contacts disposed on the base element of the device, and electrically coupled to the at least one sensing element are used for establishing electrical connection with the at least one sensing element.

40 Claims, 22 Drawing Sheets

Related U.S. Application Data

(60) Provisional application No. 62/029,512, filed on Jul. 27, 2014, provisional application No. 61/943,417, filed on Feb. 23, 2014, provisional application No. 61/934,715, filed on Feb. 1, 2014.

(51) Int. Cl.
*G01N 27/00* (2006.01)
*G01N 31/16* (2006.01)
*G01L 1/22* (2006.01)
*A61M 5/168* (2006.01)

(52) U.S. Cl.
CPC ...... *B01L 3/502707* (2013.01); *G01L 1/2262* (2013.01); *B01L 3/502746* (2013.01); *B01L 2200/0605* (2013.01); *B01L 2200/143* (2013.01); *B01L 2200/147* (2013.01); *B01L 2300/023* (2013.01); *B01L 2300/0645* (2013.01); *B01L 2300/123* (2013.01); *B01L 2400/0655* (2013.01); *B01L 2400/082* (2013.01)

(58) Field of Classification Search
USPC ........ 422/502, 503, 504, 68.1, 521, 552, 50, 422/82.01, 82.02; 436/43, 180, 149; 264/478
See application file for complete search history.

(56) References Cited

U.S. PATENT DOCUMENTS

| | | | |
|---|---|---|---|
| 7,108,354 B2 | 9/2006 | Gulvin et al. | |
| 7,246,524 B1 | 7/2007 | Kholwadwala et al. | |
| 7,250,775 B1 | 7/2007 | Collins et al. | |
| 7,291,126 B2 | 11/2007 | Shekalim | |
| 7,311,693 B2 | 12/2007 | Shekalim | |
| 7,318,351 B2 | 1/2008 | Cobianu et al. | |
| 7,375,404 B2 | 5/2008 | Park et al. | |
| 7,377,907 B2 | 5/2008 | Shekalim | |
| 2002/0053242 A1 | 5/2002 | Tai et al. | |
| 2002/0097303 A1 | 7/2002 | Gulvin et al. | |
| 2002/0117517 A1 | 8/2002 | Unger et al. | |
| 2002/0127736 A1 | 9/2002 | Chou et al. | |
| 2003/0116738 A1 | 6/2003 | O'Connor et al. | |
| 2004/0086427 A1 | 5/2004 | Childers et al. | |
| 2004/0209354 A1 | 10/2004 | Mathies et al. | |
| 2005/0067286 A1 | 3/2005 | Ahn et al. | |
| 2005/0230767 A1* | 10/2005 | Park | B01L 3/502707 257/414 |
| 2005/0279635 A1 | 12/2005 | Chow et al. | |
| 2006/0213275 A1 | 9/2006 | Cobianu et al. | |
| 2007/0028683 A1 | 2/2007 | Ionescu-Zanetti | |
| 2007/0224084 A1 | 9/2007 | Holmes et al. | |
| 2007/0250007 A1 | 10/2007 | Shekalim | |
| 2009/0129952 A1 | 5/2009 | Patrascu et al. | |
| 2009/0317298 A1 | 12/2009 | McAvoy et al. | |
| 2010/0018584 A1 | 1/2010 | Bransky et al. | |
| 2010/0072565 A1 | 3/2010 | Liu et al. | |
| 2010/0098585 A1* | 4/2010 | Chiu | B01L 3/502707 422/68.1 |
| 2010/0202038 A1* | 8/2010 | Chung | G02B 26/001 359/291 |
| 2013/0217598 A1 | 8/2013 | Ludwig et al. | |
| 2014/0273187 A1* | 9/2014 | Johnson | G01N 27/3274 435/287.2 |

FOREIGN PATENT DOCUMENTS

| | | |
|---|---|---|
| WO | 2003000416 A2 | 1/2003 |
| WO | 2008/030284 | 3/2008 |

OTHER PUBLICATIONS

Hasenkamp, et al., Polyimide/SU-8 catheter-tip MEMS gauge pressure sensor, Biomed Microdevices, 2012, pp. 819-828, vol. 14.
English Translation of Chinese Search Report dated May 21, 2018 for application No. 2015800182483.

* cited by examiner

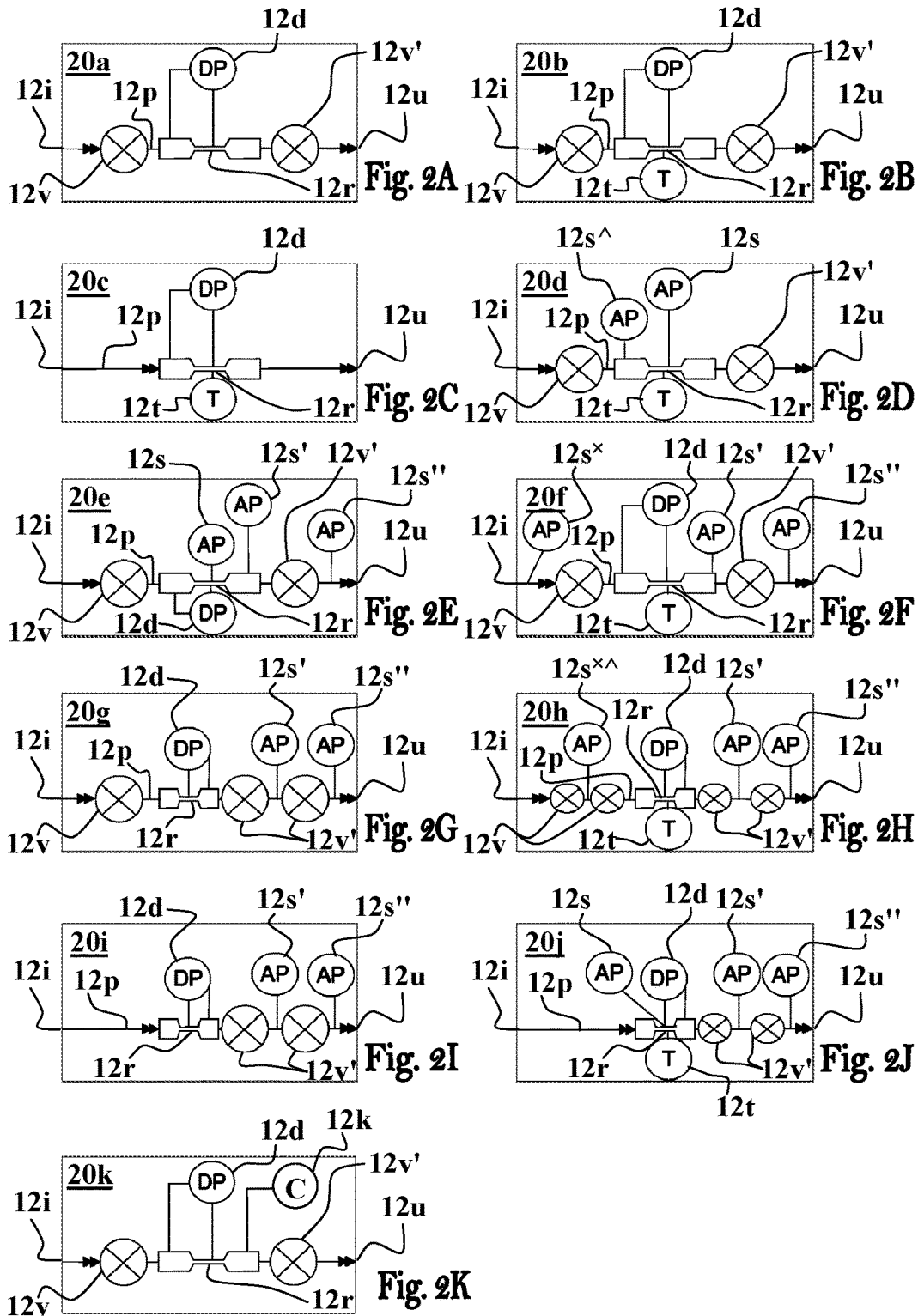

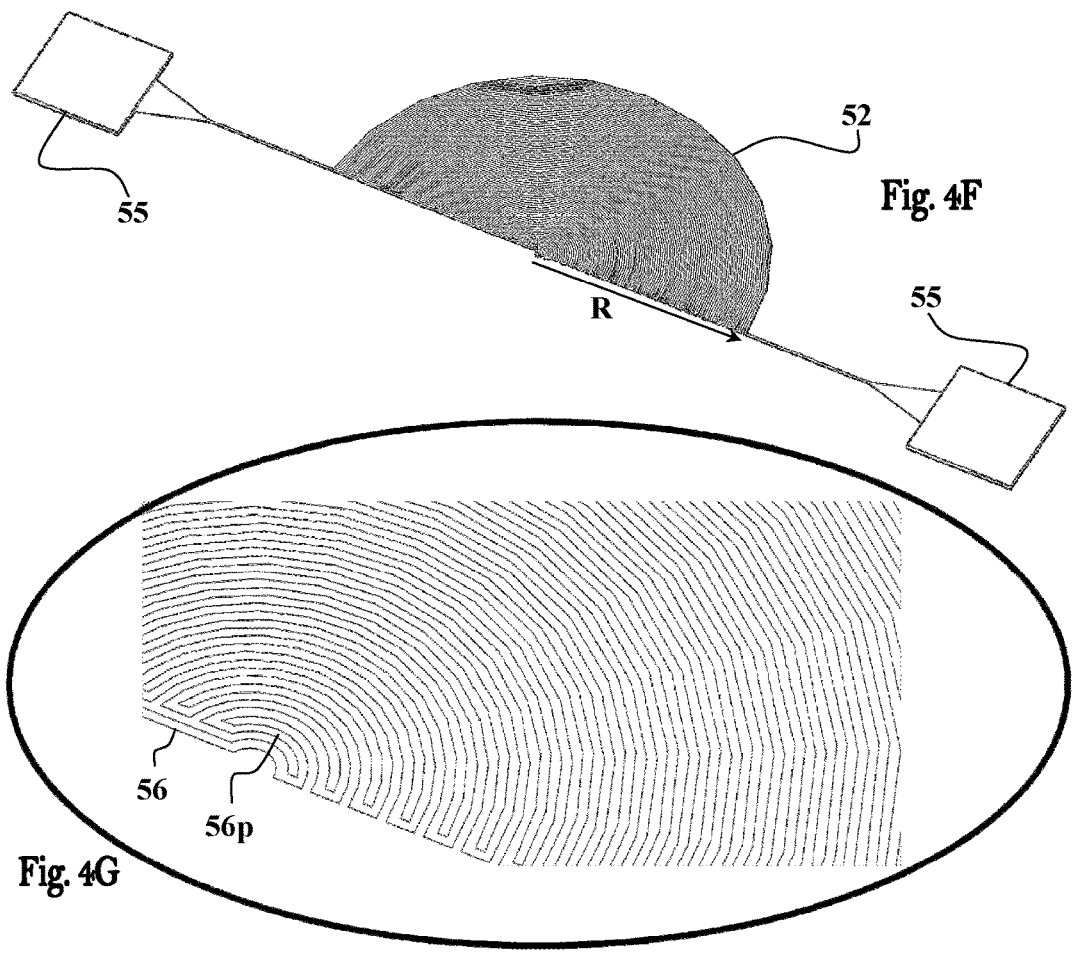
Fig. 4F
Fig. 4G
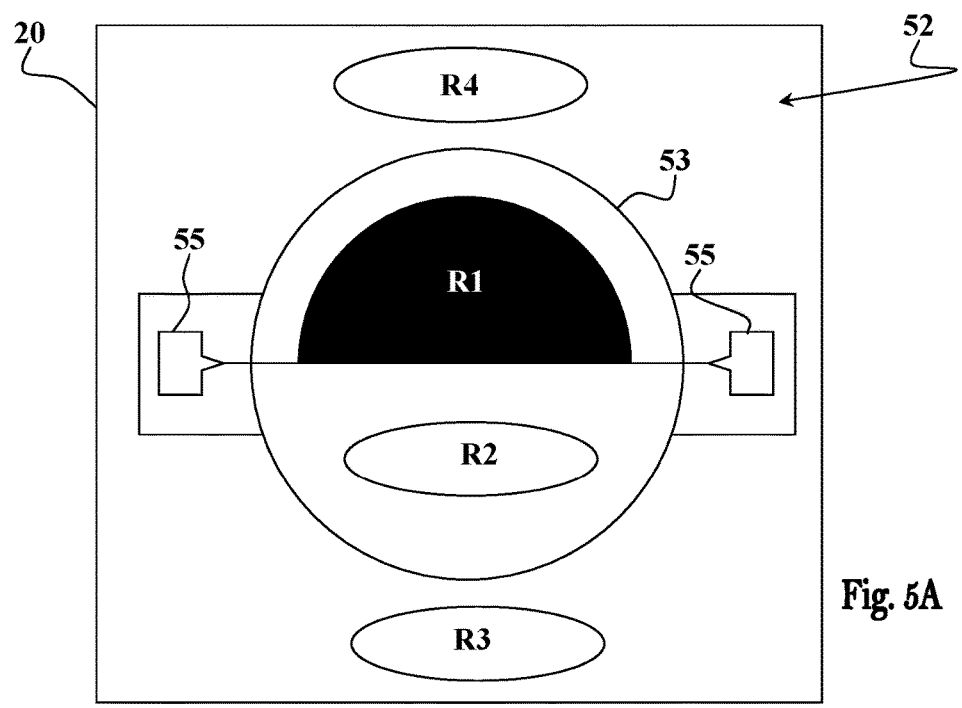
Fig. 5A

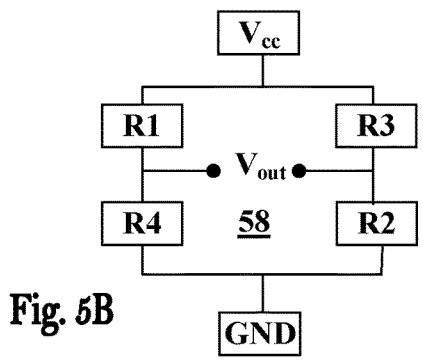
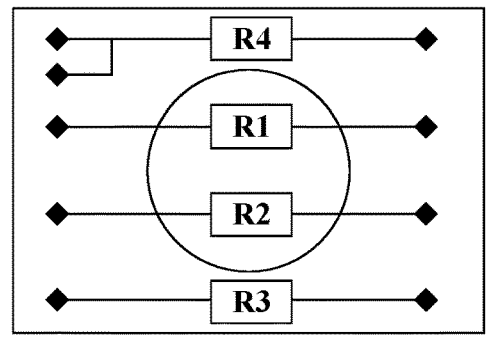
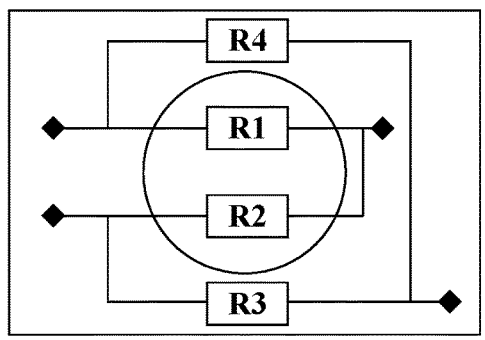
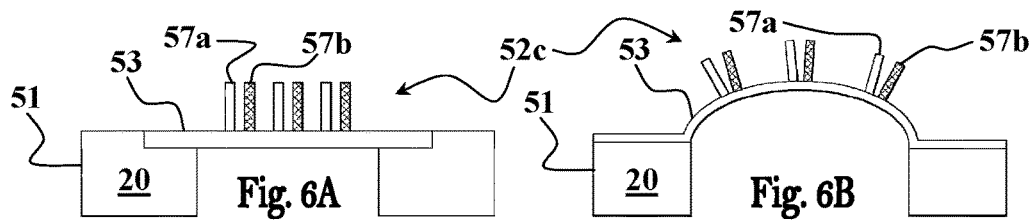
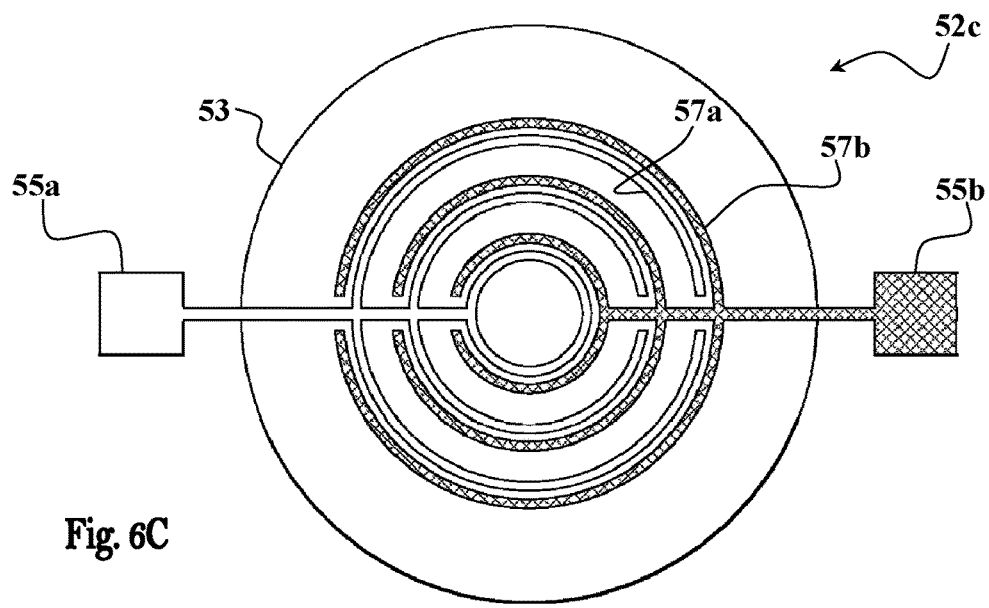

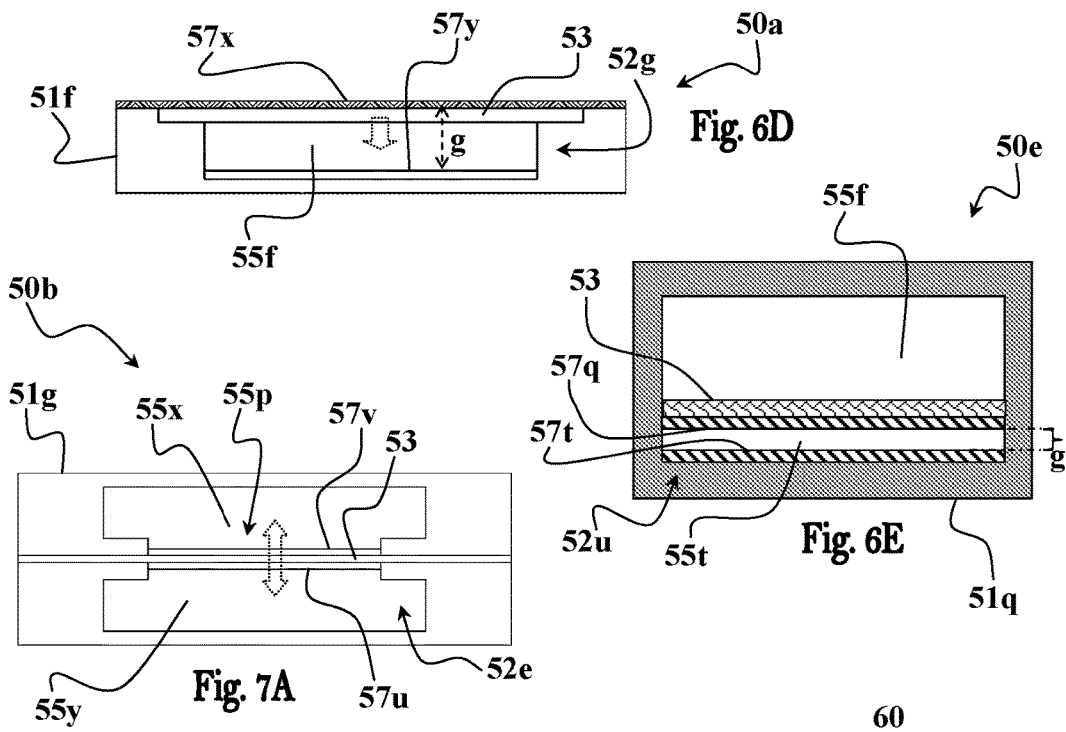
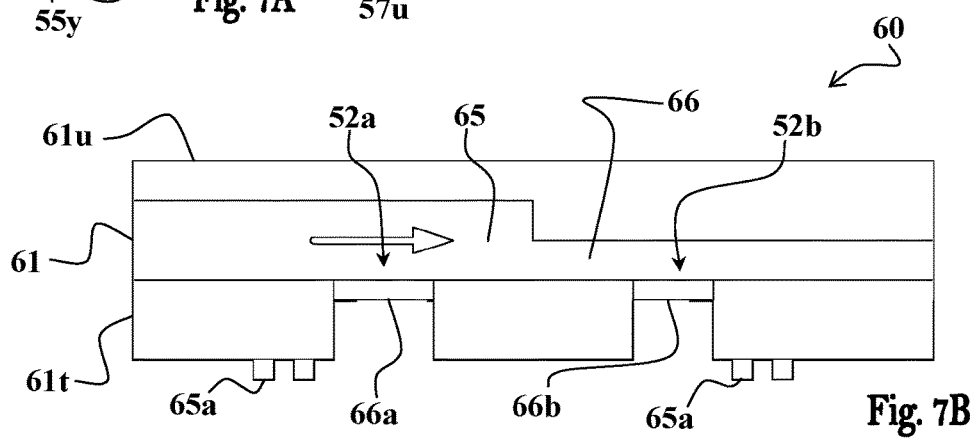
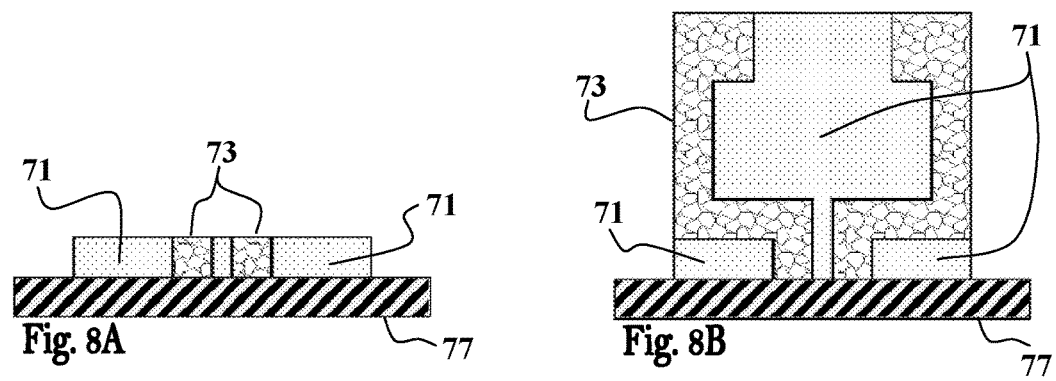

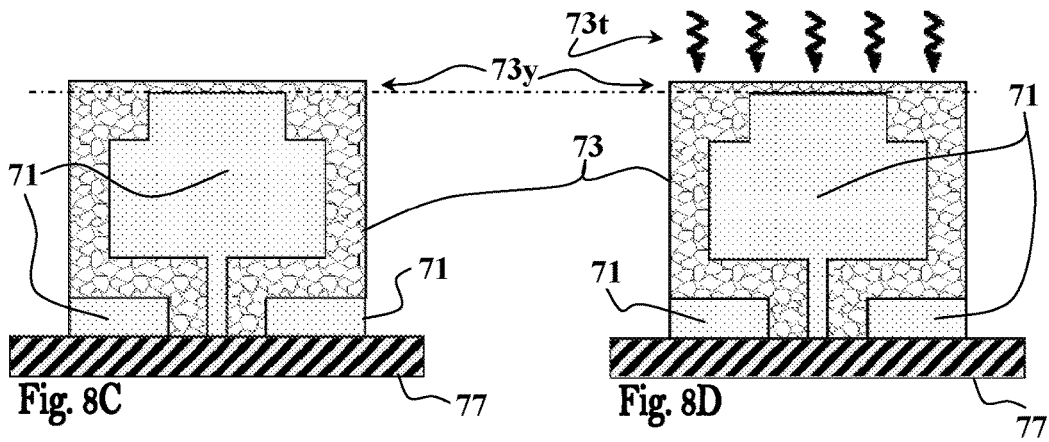
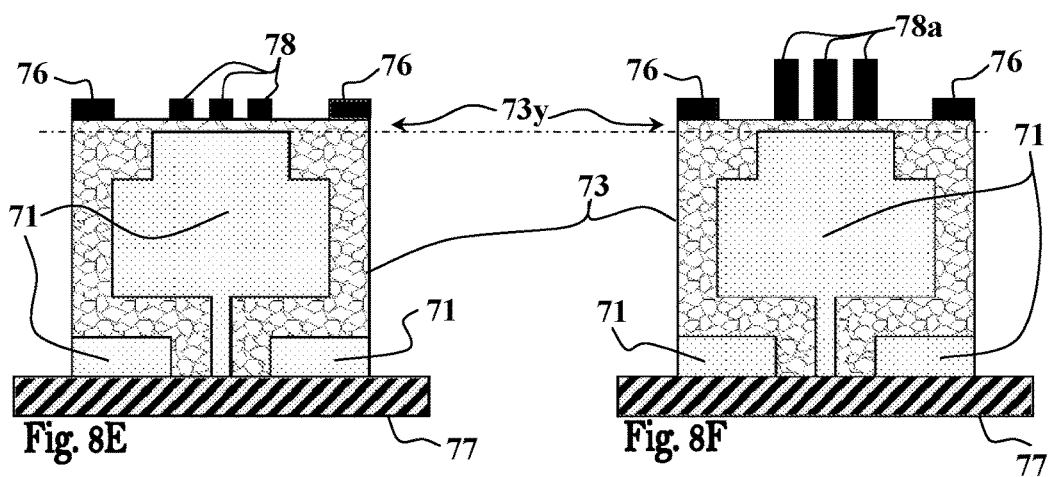
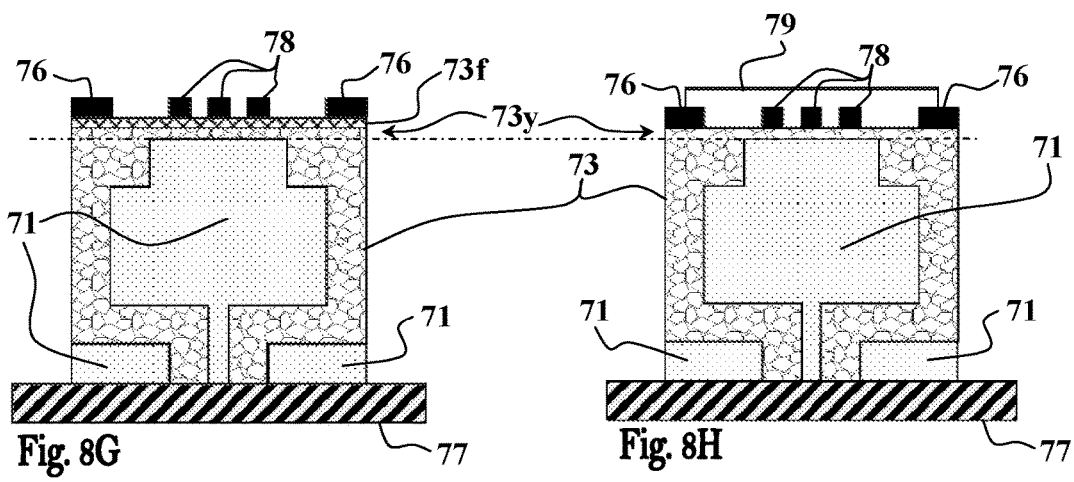

CHIP DEVICE FOR MONITORING AND REGULATING FLUID FLOW, AND METHODS OF MANUFACTURE THEREOF

TECHNOLOGICAL FIELD

The present invention is generally in the field of micro-electro-mechanical fluidic systems. More particularly, the invention relates to a polymeric chip device for measurement and control of one or more conditions of a fluid.

BACKGROUND

This section is intended to introduce various aspects of art that may be related to various aspects of the present disclosure described and/or claimed below, and to facilitate a better understanding of the various aspects of the present disclosure. It should be therefore understood that these statements are to be read in this light, and not as admissions of prior art.

The fluidic devices (e.g., medical devices) used nowadays usually incorporate micro-electro-mechanical (MEM) sensing elements. In such devices, the sensors are usually implemented by semiconductor structures, and the fluid flow path of the device and their connections with the fluid system, their packaging, and their mechanical/electrical interfaces are implemented by plastic fabrication techniques. In addition, electrical connectivity of such MEM devices with external systems is not implemented directly on the semiconductor die, and requires, inter alia, additional electrical interface involving wiring and electrical contacts, plastic structures, and printed circuit board (PCB).

These manufacturing techniques require accurate attachment and complex of the semiconductor die to its carrier to achieve electrical and mechanical connectivity to guarantee that pressure forces are correctly transmitted to the sensing elements, and obtain proper alignment between the fluid flow structures formed in the plastic packaging with the sensors and/or actuators implemented in the semiconductor die. This combination of manufacturing techniques typically results in a costly, and considerably complex, fabrication and integration of the fluidic MEM sensor (e.g., Silicon) into the fluidic devices.

Fluidic MEM devices fabrication techniques known from the patent literature are described in the following patent publications.

U.S. Pat. No. 7,311,693 describes a drug delivery device with a pressurized reservoir in communication with a flow path to an outlet. The flow path includes two normally-closed valves and a flow restriction. A pressure measurement arrangement measures a differential fluid pressure between two points along the flow path which span at least part of the flow restriction, one of the points being between the valves. A controller selectively opens the valves to deliver a defined quantity of the liquid medicament to the outlet.

U.S. Pat. No. 7,377,907 describes a portable insulin delivery device that supplies insulin in a pre-pressurized chamber, passes the insulin through a pressure-dropping labyrinth to a flow control valve. The valve is activated by a piezoelectric actuator. This allows for precise insulin delivery. An electronic package provides for programming of basal rates and bolus. A pressure sensor relays data concerning normal operation and pressure changes that indicate problems. The processor, keypad, displays power source, fluid pressure sensor and fluid flow control actuator are housed in a base unit. A removable cartridge unit houses the pre-pressurized fluid reservoir, flow path labyrinth, and flow control valve.

U.S. Pat. No. 7,318,351 describes a pressure sensor constructed of a plastic package. The plastic package incorporates in the same material a sensing diaphragm including tensile and compression regions. Deposited on the diaphragm are metal electrodes and a polymer film having piezoresistive properties. The electrodes and/or the polymer film are directly printed onto the plastic package without the use of a mask.

U.S. Pat. No. 7,375,404 describes a micro-electro-mechanical system (MEMS) device, along with means for its fabrication and operation for microfluidic and/or biomicrofluidic applications. The MEMS device includes a substrate, optional electrodes on the substrate, a patterned structure on the substrate, the patterned structure having a fluidic microchannel aligned with one or more of the optional electrodes, an encapsulation membrane covering the microchannel, and an optional reactive layer deposited over the electrode in the microchannel. MEMS devices of preferred embodiments permit a leak-tight seal to be formed around the microchannel and fluidic interconnects established for robust operation of fluidics-based processes. MEMS devices of other preferred embodiments permit reversible attachment and separation of the encapsulation membrane relative to the patterned structure.

GENERAL DESCRIPTION

Certain aspects of possible embodiments are presented hereinbelow merely to provide certain forms the embodiments might take. It is noted that these aspects are not intended to limit the scope of the presently disclosed subject matter. Indeed, the embodiments may encompass a variety of aspects that may not be set forth below.

The present invention is directed, in some embodiments, to a fluidic monolithic micro-electro-mechanical (MEM) device. More particularly, the present invention provides embodiments of fluidic MEM devices which functional components and packaging are implemented as a single massive undifferentiated unit (also referred to herein as a single polymeric chip, or SPC for short). This is different from conventional micro-electro-mechanical systems (MEMS) in which mechanical and electrical components are typically implemented in a semiconductor wafer and wherein separate packaging components are usually required to provide electrically connectivity to the semiconductor die and to properly align between the electro-mechanical elements implemented by the semiconductor die and fluid flow structure of the device.

Optionally, and in some embodiments preferably, the fluidic MEM device of the present invention is mostly, or entirely, fabricated from polymeric materials. The use of polymeric material in the fabrication of the fluidic MEM device is beneficial as it permits manufacture of the body/package and functional electro-mechanical components of the device by similar processes, and within the same fabrication framework. It was found by the inventors of the present invention that MEM devices fabricated from polymeric materials with, or without, non-polymeric materials, is substantially advantageous over MEM devices fabricated only from non-polymeric materials.

The advantages of such polymeric material implementations include, inter alia, allowing a mass production process of fully integrated monolithic polymeric devices (e.g., within one piece of wafer) with conductive or semi-conductive materials for connection and transduction. As will be appreciated, the fabrication techniques described herein also advantageously provides fluidic MEM devices having high robustness, fracture durability, and biocompatibility.

In addition, as will be described and demonstrated hereinbelow, fabrication techniques of the fluidic MEM device according to some embodiment of the present invention allows embedding together the functional electro-mechanical components and the packaging of the fluidic MEM device into a single/monolithic piece/unit during the device fabrication. This is unlike conventional fabrication techniques of fluidic MEMS, typically made of Silicon, which must be separately packed inside another piece of material to provide fluidic alignment and sealing, and electrical connectivity to the device.

Polymeric materials for fluidic MEMS offer various advantages over conventional Silicon MEMS. These may include: Biocompatibility, better shock tolerance, low cost of raw material, light weight, easier processing and integration with conventional fluidic plastics, large variety of manufacturing techniques, large variety of available polymers and molecular structures, high flexibility, easy mixture with various ingredients (e.g., to produce conductive polymers). Various properties of polymeric materials (e.g., high elastic modulus) are advantageously employed in different embodiments of the present invention to incorporate into the fluidic MEM devices various sensing elements, flow restrictors, valves, and other functional elements. The fabrication cost, integration cost and overall performance (e.g. in terms of minimal dimensions, accuracy, resolution and sensitivity) can be appreciably better compared with conventional Silicon MEMS.

For example, and without being limiting, in some embodiments the fluidic MEM device comprises one or more pressure sensors, such as, but not limited to, strain gauge, capacitive gauge, piezoresistive gauge and suchlike. The elasticity of the polymeric materials from which the fluidic MEM device is manufactured allows implementing pressure sensors that are much more sensitive, relative to the conventional Silicon implementations of such sensors, thereby providing for higher measurement resolution. For example, and without being limiting, in some embodiments polymeric implementations of pressure sensors of the fluidic MEM device of the present invention are configured to measure fluid pressures in the range of about −5000 mmHg to about +5000 mmHg.

In various exemplary embodiments of the present invention the fluidic MEM device can comprise at least one element made from an electrically conductive polymer, such as, but not limited to, polypyrrole (PPy) or its derivatives. Also contemplated are other types of conductive polymers, including, without limitation, polyaniline (PANI), polythiophene, polyacetylene and poly-para-phenylene. Further contemplated for use according to some embodiments of the present invention are conductive polymeric composites, such as, but not limited to, a composite comprising electrically conductive particles and/or micro-particles and/or electrically conductive nano-particles (e.g., silver (Ag), carbon nanotubes (CNTs)) and a conductive (e.g., PPy or PANI) or non conductive polymer (e.g., PDMS).

Embodiments of the fluidic MEM device of the present invention can be used in a variety of applications, such as, but not limited to, drug delivery systems, measurement of blood flow parameters (e.g., flow rate, fluid pressure) and its components, inhalation, rhinomanometry, urine, infusion systems, and also in non-medical systems for monitoring other types of fluid media (e.g., water, ink). The fluidic MEM devices disclosed herein are also usable in harsh environments, e.g., environments that include dampness, wetness, damaging gases, heavy particulate matter, high G-forces, shocks, high temperatures, and other environmental conditions as well. Of course, the fluidic MEM devices disclosed herein may be also used in non-harsh environments.

For example, and without being limiting, the fluidic MEM device may be used (immersed) in liquid medicaments e.g., in drug delivery devices or other medical devices. For instance, in some possible embodiment the fluidic MEM devices of the present invention are used in insulin pumps, elastomeric devices, intravenous (IV) infusion (e.g., for measuring fluid pressure and/or flow rate and/or regulating the fluid flow), or as simple flow sensors in a syringe pump. The MEM devices may be also used to measure and/or control the flow in a nebulizer or any other gas medicament dispenser.

In some possible embodiments the fluidic MEM device is an implantable device.

The fluidic MEM device in some possible embodiment may be attached (e.g., bonded) to a printed circuit board (PCB) e.g., as a simple surface-mount device (SMD). Alternatively, in some possible embodiments, the fluidic MEM devices may be used as a PCB and SMD components can be attached (e.g., bonded) to them.

In some possible embodiments the fluidic MEM device comprises polymeric structures usable as mechanical matching and/or locking and/or guiding and/or latching mechanism for connection with external devices and/or systems. The fluidic MEM device in some embodiments can have the ability to be plugged to, and thereupon operate with, an external system (plug and play device). In such embodiments the external system automatically recognizes the connection established with the fluidic MEM device and responsively begins to operate the device and exchange with it data and/or instruction signals.

In some possible embodiments the fluidic MEM device is configured and operable to control flow of a fluid media (e.g., medicament administration) and/or measure conditions (e.g., pressure and/or flow rate and/or temperature) of the fluid media. For example, and without being limiting, the fluidic MEM device may comprise one or more pressure sensors (absolute and/or differential). Each pressure sensor may comprise one or more membranes. Preferably, the absolute pressure sensors are implemented to employ either the atmospheric pressure (gauge pressure sensor) or a fixed reference pressure provided within a sealed chamber (sealed pressure sensor), as their reference pressure.

The device may also comprise one or more temperature sensors (e.g., based on resistive transduction techniques) integrated therein. The temperature sensor is configured in some embodiments to measure fluid temperatures in the range of about −50° C. to about +150° C.

Optionally, and in some embodiments preferably, the pressure sensors are made of polymeric membranes and/or plates having conductive materials deposited thereon to perform transduction (e.g., resistive, capacitive or piezoresistive). A fluid channel or cavity provide in the MEM device is used to enable the fluid media to interact with the membrane. In some embodiments the fluidic MEM device can comprise additional channels/cavities (or any other polymeric structure) configured to permit interaction of another side or portion of the membrane of the sensor with the fluid media, which can be a part of the packaging of the device in a way allowing to use the device as a flow sensor, differential flow sensors, and/or pressure sensor.

Alternatively or additionally, the fluidic MEM device may comprise one or more flow rate sensors. The flow rate sensors may utilize at least one restrictor formed in a fluid flow path of the device. Optionally, and in some embodiments preferably, the restrictors are polymeric channels of defined dimensions. The flow rate sensors are configured in some embodiments to measure fluid flow rates in the range of about 0.1 nano liters per hour to about 300 liters per hour.

The fluidic MEM device of the present invention may comprise other types of sensing elements for measuring and monitoring properties of the delivered fluid substance. For example, and without being limiting, the fluidic MEM device may comprise sensing elements for measuring electrical and/or chemical properties of the fluid media (e.g., electrical conductivity).

In some possible embodiments the fluidic MEM device comprises one or more valves. Optionally, and in some embodiments preferably, the valves are made of polymeric membrane and/or frame with a boss located at its center. The valves may be actuated mechanically (e.g., using an external shiftable pin configured to controllably press a flow regulating structure implemented in the MEM device) and/or magnetically and/or electromagnetically (e.g., using a deposited magnetic polymer or a magnetic layer/piece attached to the central boss). In some embodiments the polymeric membrane and/or frame of the valves can be used as mechanical suspension element and/or spring. The payload boss element of the valves may be coupled to the suspension elements so as to ensure suspension of the payload boss element above the opening to be sealed. In some embodiments the payload boss element of the valve is used as a sealer.

A reservoir (e.g., a pressurized drug container) may be used to supply the device pressurized fluid with sufficient pressure to allow the correct flowing of the medicament from the reservoir to a patient. For example, and without being limiting, a pressurized reservoir used with the fluidic MEM device may be one of: an elastomeric device, a spring loaded device, a gravity device, any electrically powered device, any mechanically powered device, a syringe pump; or a peristaltic pump.

In some possible embodiments the fluidic MEM device comprises one or more elements made from non-polymeric materials (e.g., comprising semiconductor materials and/or metals). For example, and without being limiting, semiconductor methods (e.g., coating, evaporation, electroplating, liftoff, and suchlike) may be used to deposit conductive elements on (and/or in) the MEM device.

Accordingly, the fluidic MEM device may be used to measure the flow rate and/or pressure of a liquid, or gas, or nebulized substance (e.g., drug). Control and/or measurement electronic units of the fluidic MEM device may be separated units, or integrated into the device.

In some possible embodiments the fluidic MEM device is manufactured to integrally include one or more electronic control modules applicable to receive and process measurement data/signals from the sensing elements of the device, generate control signals for actuating valves and/or any other possible actuators of the device, and exchange data and/or instructions with external systems.

In some possible embodiments the fluidic MEM device is manufactured using standard mold techniques. The fluidic MEM device may be manufactured utilizing other possible techniques, such as, but not limited to, 3D printing, micro scale molding, micro machining, nano and micro imprinting, hot embossing, injection molding, lithography, laser micromachining, lamination, additive manufacturing, CNC and micro CNC, etc.

In some embodiments fluid regulating elements are implemented in the MEM device by coupling a mechanical suspension element to the payload boss element. For example, a flexible/elastic membrane coupled to a fluid flow path of the device may be used as the suspension element (acting as a spring), and the payload boss element can be attached to the center of the membrane, such that the fluid flow path can be restricted, or entirely occluded, by pressing the boss element towards the flow path. The mechanical suspension element and/or the payload boss element, may be coupled to an external (electromagnetic or mechanical) actuating element configured to drive the payload boss to restrict/occlude the fluid flow path.

As will be appreciated by those skilled in the art, the fluidic MEM device may comprise microstructures and/or MEMS, and/or macrostructures. The MEM device can have an integrated polymeric packaging having integrated conductive pads, and/or pins, and/or wires, and/or tracks, and a connection system for connecting it to an external system and/or device. In some possible embodiments the total size of the MEM device is in a range of about 0.125 cubic millimeters to about 125 cubic centimeters, but smaller geometrical dimensions are also possible.

Optionally, and in some embodiments preferably, the fluidic MEM device is fabricated from wafers made at least in part of polymeric materials, which allows embedding the wafer level packaging of each fluidic MEM device on the wafer during the wafer fabrication. This is different from conventional fabrication techniques of MEM fluidic devices made of silicon, where each device (i.e., die element) of the wafer must be separately packed inside another material by additional fabrication steps. This polymeric manufacture technique permits mass production of the fluidic MEM devices with all their electro-mechanical elements and fluid flow structures/components within a single piece of wafer material, and many other advantages as well, such as the ability to perform additional semiconductor fabrication processes (e.g., lithography, metal deposition, electroforming, and etching), layer by layer fabrication, easy integration with semiconductors and electronics.

In some possible embodiments at least one of a top and bottom layer of the wafer is a complete flat surface. The dies structures within the wafer may be connected to each other by one or more bridges and/or gates, and/or connection layers. The wafer may be fabricated using any polymeric manufacture technique, such as, but not limited to, 3D printing, micro scale molding techniques, micro machining, nano and micro imprinting, hot embossing, injection molding, lithography, laser micromachining, etc.

The wafer can include one or more dies implementing the fluidic MEM device. In exemplary embodiments the wafer can comprise at least one layer/pattern comprising an electrically conducting material such as, but not limited to, gold (Au), Copper (Cu), Aluminum (Al), Platinum (Pt), Nickel (Ni), and/or alloy of a specified material. In other exemplary embodiments the conductive layers/patterns may be coated by one or more layers of electrically insulating materials (e.g., PDMS, Parylene, SU8) to electrically isolate them from the fluid media or protect them from causes of degradation (e.g., humidity, oxygen).

According to some embodiments, the wafer can have circular, rectangular, or any other geometrical shape of any dimension.

In some embodiments the wafer can comprise at least one layer/pattern comprising a conductive polymer, such as, but not limited to, polypyrrole (PPy) or its derivatives. Also contemplated are other types of conductive polymers, including, without limitation, polyaniline (PANI), polythiophene, polyacetylene and poly-para-phenylene. Further contemplated for use according to some embodiments of the present invention are conductive polymeric composite, such as, but not limited to, a composite comprising electrically conductive particle and/or micro particles and/or electrically conductive nanoparticles (e.g., silver (Ag), carbon nanotubes (CNTs)) and a conductive (e.g., PPy or PANI) or non-conductive polymer (e.g., PDMS, SU8).

In some embodiments the wafer is constructed from two or more semi-finished semi-wafers such that each semi-wafer comprises dies of semi-finished devices which construction is completed by attaching (e.g., ultrasonic welding, bonding, gluing, laser welding) the semi-finished wafers one to the other. For example, the complete wafer may be constructed from two semi-finished wafers, each comprising certain flow and/or measuring and/or actuating elements designed to be joined and yield the MEM device by attaching the wafers one to the other. Conductive elements may be deposited on the dies in each semi-finished wafer configured to establish electrical connection between elements of the semi-finished wafers and/or with external devices/systems.

In some embodiments one or more metal layers are deposited and/or patterned onto the wafer using any suitable metal deposition technique, such as, but not limited to, sputtering, evaporation, electroplating electroforming, printing, and printed circuit board (PCB) technology.

In some embodiments the mechanical elements may be fabricated with, or without, a supportive sacrificial layer, depending on the fabrication technique and the functionality of the mechanical element. For instance, if the fabrication process requires a sacrificial layer any mechanical element of the MEM device remains fixated/immobilized until the sacrificial layer is removed, (e.g., mechanically, by pressurized air and/or water, chemical solution, temperature, melting, or any other technique) i.e., membrane deformation will not be possible prior to the removal of the sacrificial layer. If the fabrication process doesn't require a sacrificial layer, the mechanical elements will be movable within the wafer immediately after fabrication, according to the design of the MEM device.

The wafer may comprise structural elements, which can be considered as part of the packaging of the fluidic MEM device structured therein.

In some embodiments the wafer can be configured such that the dies of the fluidic MEM devices within the wafer can be bonded directly to a printed circuit board (PCB) e.g., as a standard surface-mount device (SMD).

One inventive aspect of the present invention relates to a device for monitoring fluid media. The device comprises a base element having at least one fluid port and at least one cavity or fluid flow path fluidly coupled to the at least one fluid port for enabling fluid exchange of fluid media therewith. Optionally, and some embodiments preferably, the base element is a monolithic unit made from a certain (same) type of material. At least one sensing element associated with the cavity or fluid flow path is used in the device for measuring at least one property or condition of fluid media introduced into the device, and for generating measurement data or signals indicative thereof. The device further comprises electrical contacts disposed on the base element, or other part of the device, and electrically coupled to the at least one sensing element.

In some embodiments the sensing element comprises two or more electrodes disposed inside the cavity or fluid flow path configured and operable to measure electrical conductivity of the fluid media. The sensing element may comprise a first pair of spaced apart electrodes for flowing a predefined electrical current through the cavity or fluid flow path when filled with the fluid media, and a second pair of spaced apart electrodes for measuring an electrical voltage induced by the predefined electrical current.

At least one membrane may be used in the device, the membrane is associated with the cavity or fluid flow path and configured and operable to elastically deform responsive to pressure conditions inside said cavity or fluid flow path. Optionally and in some embodiments preferably the at least one membrane is made from the same material from which the base element is made.

The at least one sensing element may comprise a transducing element disposed on at least one side of the membrane and being configured and operable to generate the measurement data or signals responsive to the pressure conditions. For example, and without being limiting, the at least one transducing element may comprise electrically conducting lines deposited on the membrane and forming a plurality of adjacently located predetermined patterns comprising at least one of rectangular-wave pattern, zigzag-like wavy pattern, and arc-shaped pattern. The patterns are preferably configured to maximize a length of the electrically conducting lines deposited on the membrane.

In some possible embodiments the fluid flow path comprises a constriction, and at least one membrane of the device is associated with the constriction and being configured and operable to elastically deform responsive to pressure conditions inside it. The device may comprise at least one membrane in a section of the fluid flow path not including the constriction. Alternatively or additionally, the device may comprise at least one membrane coupled to the constriction, and actuating means coupled to the membrane are used to controllably deform the membrane and to thereby regulate fluid passage through the constriction.

In some possible embodiments the device comprises at least one transducing element disposed on a surface area of the base element of the device not affected by the deformations of the at least one membrane. At least one of the transducing elements disposed on a surface area of the base element not affected by the deformations of the at least one membrane may be used as a temperature sensor. Optionally, and in some embodiments preferably, the transducing elements are configured and operable to implement a Wheatstone bridge circuitry.

The device may comprise at least one electrical circuitry mounted on the base element of the device and electrically coupled to one or more of the electrical contacts. Optionally, and in some embodiment preferably, the electrical circuitry comprises a control unit configured and operable to receive and process the measurement data generated by the at least one sensing element and generate corresponding control signals for measuring and/or regulating the flow of the fluid media.

In some embodiments the device has a layered structure formed on the base element and comprises at least one encapsulating layer structured and arranged to sealably form the at least one membrane over the at least one cavity or fluid flow path to thereby enable the at least one membrane to interact with fluid media when introduced into the at least one cavity or fluid flow path. Optionally, and in some embodiments preferably, the base element is made from two or more layers structured and arranged to construct the at least one cavity or fluid flow path and the at least one fluid port of the base element by their attachment one to the other.

In some embodiment the device has a layered structure formed on the base element. The device may comprise a fluid path layer having the cavity or fluid flow path and configured and operable to sealably connect to the base element and establish fluid communication between the at least one fluid port and the cavity or fluid flow path, and an encapsulating layer having the at least one membrane and configured and operable to sealably connect the fluid path layer and align said at least one membrane with the cavity or fluid flow path to thereby enable the at least one membrane to interact with fluid media when introduced into said cavity or fluid flow path. The device may comprise an intermediate layer disposed between the flow path and encapsulating layers and comprising at least one slot, each slot being aligned with a membrane of the encapsulating layer and configured to receive fluid media from the cavity or fluid flow path of the flow path layer.

In a possible variant the device has a layered structure formed on the base element, where the base element comprises the at least one membrane, and wherein the device comprises a transition layer, having at least one fluid passage, each fluid passage being associated with a respective fluid port of the base element, and at least one slot, each slot being associated with a membrane of the base element, the transition layer configured and operable to sealably connect to the base element and fluidly communicate each fluid passage with its respective fluid port and align each slot with its respective membrane, and an encapsulating layer having the cavity or fluid flow path and configured and operable to sealably connect to the transition layer and fluidly communicate between the cavity or fluid flow path and the at least one fluid passage, thereby enabling passage of fluid media into the cavity or fluid flow path from the at least one fluid port in the base section via its respective fluid passage in the transition layer, and align the cavity or fluid flow path with the at least one slot, to thereby enable each membrane to interact with fluid media introduced into its respective slot via the cavity or fluid flow path. The device may comprise a fluid flow path in the encapsulating layer, where the fluid flow path having a constriction, and wherein at least one slot of the transition layer is in fluid communication with the constriction to enable its respective membrane to interact with fluid media introduced thereinto, and at least one other slot is in fluid communication with a non-constricted section of the fluid flow path to enable its respective membrane to interact with fluid media introduced thereinto. The device may comprise a fluid passage in the base element communicating between constricted and non-constricted regions of the fluid flow path. The fluid passage may comprise membrane configured and operable to an elastically deform responsive to pressure differences between the constricted and non-constricted regions of the fluid flow path, and the membrane having a transducing element configured and operable to generate measurement data or signals responsive to the deformations.

In some possible embodiment the encapsulating layer comprises at least one elastically deformable membrane having a flow regulating element configured and operable to engage a fluid passage of the transition layer to thereby alter fluid passage therethrough.

Optionally, and in some embodiments preferably, the device includes at least one transduction element in the encapsulating layer.

The device may be configured and operable to be mounted on a PCB while establishing electrical contact with at least some of the electrical contacts of the device. Optionally, and in some embodiments preferably, the PCB comprises a cavity, and the at least one of the membranes of the device is adapted to deform towards or away said cavity of the PCB.

Optionally, and in some embodiments preferably, the device comprises quick connection means configured and operable to secure the device to an external device while establishing electrical connectivity therewith.

In another aspect there is provided a fluid delivery system comprising at least one monitoring device as described hereinabove or hereinbelow, at least one fluid source for supplying the fluid media to the at least one monitoring device, and at least one fluid dispensing device for receiving fluid media from either the at least one monitoring device or the fluid source.

In yet another aspect there is provided a fluid delivery system comprising at least one monitoring device as described hereinabove or hereinbelow, at least one fluid source for supplying the fluid media to the monitoring device, at least one fluid dispensing device for receiving fluid media from either the at least one monitoring device or the fluid source, and a control unit coupled to the monitoring device and configured to receive and process the measurement data generated by the sensing element. The monitoring devices may be connected to each other in the system in series via their fluid ports. Alternatively, the monitoring devices are connected via their fluid ports to a fluid delivery line connecting between the fluid source and the fluid dispensing device.

In yet another aspect there is provided a method for constructing a flow control device. The method comprises constructing from a specific material a monolithic base structure comprising at least one fluid port and a cavity of a fluid flow path in fluid communication with the at least one fluid port for enabling exchange of fluid media therewith, constructing at least one sensing element associated with a cavity or fluid flow path of the device and configured and operable for measuring at least one property or condition of fluid media introduced thereinto and generating measurement data or signals indicative thereof, and forming on the device electrically conducting patterns for providing electrical connection to the at least one sensing element. The constructing of the base structure may comprise forming at least one membrane associated with the cavity or fluid flow path and configured and operable to elastically deform responsive to pressure conditions inside said cavity or fluid flow path, and wherein the at least one sensing element is at least partially structured on the membrane. The constructing of the base structure may comprise forming a constriction in the cavity or fluid flow path and forming at least one elastically deformable membrane associated with the constriction, and wherein at least one membrane associated with the constriction comprises a sensing element for measuring fluid pressure conditions in the constriction or mechanically coupled to an actuator for altering fluid passage through the constriction.

The method may comprise constructing a flow path layer comprising the cavity or fluid flow path, constructing an encapsulating layer comprising at least one elastically deformable membrane, wherein the at least one sensing element associated with at least one membrane and the electrically conducting patterns are constructed on the encapsulating layer, assembling a layered structures by sealably attaching the encapsulating layer to the flow path layer such that at least one membrane of the encapsulating layer is disposed over the cavity or fluid flow path of the flow path layer, and sealably attaching the layered assembly to the base structure such that fluid communication is established between the at least one fluid port of the base structure and the cavity or fluid flow path of the flow path layer.

Alternatively, the method may comprise constructing a flow path layer comprising the cavity or fluid flow path, constructing an intermediate layer comprising at least one slot, constructing an encapsulating layer comprising at least one elastically deformable membrane, wherein the at least one sensing element associated with at least one membrane and the electrically conducting patterns are constructed on the encapsulating layer, assembling a layered structure by sealably attaching the encapsulating layer to the intermediate layer such that at least one membrane of the encapsulating layer is disposed over at least one slot of the intermediate layer, and sealably attaching the intermediate layer to the flow path layer such that fluid communication is established between at least one slot of the intermediate layer and the cavity or fluid flow path of the flow path layer, and sealably attaching the layered assembly to the base structure such that fluid communication is established between the at least one fluid port of the base structure and the cavity or fluid flow path of the flow path layer.

The constructing of the base structure may comprise forming at least one membrane in the base structure, wherein the at least one sensing element associated with at least one membrane and the electrically conducting patterns are constructed on the base structure, the method may further comprise constructing a transition layer having at least one fluid passage and at least one slot formed therein, constructing an encapsulating layer having a cavity or fluid flow path, assembling a layered structure by sealably attaching the encapsulating layer to the transition layer such that fluid communication is established between the cavity or fluid flow path of the encapsulating layer and at least one fluid passage and at least one slot of the transition layer, and sealably attaching the layered structure to the base structure such that fluid communication is established between at least one slot of the transition layer and at least one fluid port of the base structure and such that at least one slot of the transition layer is positioned over at least one membrane of the base structure.

The constructing of the base structure may comprise forming at least one membrane in the base structure, wherein the at least one sensing element associated with at least one membrane and the electrically conducting patterns are constructed on the base structure. The method may further comprise constructing a transition layer having at least one fluid passage and at least one slot formed therein, constructing an encapsulating layer having a cavity or fluid flow path and at least one elastically deformable membrane having a flow regulating element, assembling a layered structure by sealably attaching the encapsulating layer to the transition layer such that fluid communication is established between the cavity or fluid flow path of the encapsulating layer and at least one fluid passage and at least one slot of the transition layer, and sealably attaching the layered assembly to the base structure such that fluid communication is established between at least one slot of the transition layer and at least one fluid port of the base structure, at least one slot of the transition layer is positioned over at least one membrane of the base structure, and the flow regulating element of at least one membrane of the encapsulating layer becomes engaged with a fluid passage of the transition layer.

In some embodiments the constructing of the encapsulation layer comprises forming the fluid flow path with a constriction, wherein the assembling of the layered structure comprises establishing fluid communication between the constriction of the encapsulating layer and at least one slot of the transition layer, where the at least one slot being associated with one of the membranes in the base structure. The constructing of the base structure may comprise forming a fluid passage in the base structure for communicating between constricted and non-constricted regions of the fluid flow path via respective slots of the transition layer, where the fluid passage comprising membrane configured and operable to elastically deform responsive to pressure differences between the constricted and non-constricted regions of the fluid flow path, and where the membrane is having a transducing element configured and operable to generate measurement data or signals responsive to said deformations.

Optionally, and on some embodiment preferably, the constructing of the at least one sensing element comprises patterning electrically conducting structures on the at least one membrane. The patterning may comprise forming at least one resistive element on the membrane configured and operable to change electrical resistance thereof responsive to the deformations of the membrane. Alternatively or additionally, the patterning may comprise forming at least one capacitive element on the membrane configured and operable for changing electrical capacitance thereof responsive to the deformations of the membrane.

The method may comprise coating at least some of the electrically conducting patterns with one or more isolating layers.

In some embodiment the base structure, or layers of the device, are made from a polymeric material, and the electrically conducting patterns of the device are made by deposition of conductive material on the polymeric material.

In some applications the forming of at least one of the base structure and one or more of the sealably attached layers, utilizes one of the following techniques: additive manufacturing, 3D printing, micro scale molding, micro machining, nano imprinting, micro imprinting, hot embossing, injection molding, lithography, and laser micromachining, CNC, lamination and micro-CNC.

The constructing of the sensing element may utilize one of the following techniques: lithography, evaporation, liftoff, electrodeposition, electroforming, electroplating, electroless deposition and other IC techniques.

The method may comprise manufacturing an array of the flow control devices as dies of a wafer in a mass production process. The wafer may comprise alignment marks to facilitate wafer orientation and the forming of the electrically conducting patterns (e.g., by lithography). The method may comprise sealing the wafer to prevent contamination by non-biocompatible materials (e.g., during chemical processing-electroforming). The wafer may be circular or rectangular in shape, and can have a cuffed edge usable to identify the wafer orientation. In some embodiments one face of the wafer is made substantially flat for forming the electrically conducting patterns thereon, and another face of the wafer is prepared for wafer dicing.

The method may comprise manufacturing in a mass production process a wafer stack comprising a plurality of said wafers stack one on top of the other. The method may comprise manufacturing in the mass production process a stack holder adapted to hold the wafer stack.

Thus, according to yet another inventive aspect there is provided a MEM production wafer comprising a plurality of dies, each die having one or more internal lumens structured and arranged to implement at least one fluid port and at least one cavity or fluid flow path. The at least one cavity or fluid flow path can be structured and arranged to couple with at least one sensing element for measuring at least one property or condition of fluid media introduced thereinto. The wafer can comprise a plurality of lateral openings, at least some of which being in fluid communication with the internal lumens of the dies. Optionally, and in some embodiments preferably, the plurality of lateral openings are structured and arranged to facilitate sealing of the internal lumens to prevent contamination of the internal flow paths or cavities during the fabrication process.

BRIEF DESCRIPTION OF THE DRAWINGS

In order to understand the invention and to see how it may be carried out in practice, embodiments will now be described, by way of non-limiting example only, with reference to the accompanying drawings. Features shown in the drawings are meant to be illustrative of only some embodiments of the invention, unless otherwise implicitly indicated. In the drawings like reference numerals are used to indicate corresponding parts, and in which:

FIG. 1C depicts a fluid delivery system utilizing a plurality of fluidic MEM devices for monitoring a fluid streamed in a fluid stream line, and FIG. 1D exemplify a fluid delivery system using a fluidic MEM-device having a restrictor and configured to control and measure at least one condition of the delivered fluid;

FIG. 2A to FIG. 2K are block diagrams showing possible embodiments of the fluidic MEM device having a restrictor in its fluid flow path, wherein FIG. 2A exemplifies a fluidic MEM device comprising two valves and a differential pressure (DP) sensor, FIG. 2B exemplifies a fluidic MEM device comprising two valves, a differential pressure sensor, and a temperature sensor, FIG. 2C exemplifies a fluidic MEM device comprising a differential pressure sensor and a temperature sensor, FIG. 2D exemplifies a fluidic MEM device comprising two valves, two absolute pressure (AP) sensors, and a temperature sensor, FIG. 2E exemplifies a fluidic MEM device comprising two valves, a differential pressure sensor, and three absolute pressure sensors, FIG. 2F exemplifies a fluidic MEM device comprising two valves, a differential pressure sensor, three absolute pressure sensors, and a temperature sensor, FIG. 2G exemplifies a fluidic MEM device comprising three valves, a differential pressure sensor, and two absolute pressure sensors, FIG. 2H exemplifies a fluidic MEM device comprising four valves, a differential pressure sensor, three absolute pressure sensors, and a temperature sensor, FIG. 2I exemplifies a fluidic MEM device comprising two valves, a differential pressure sensor, and two absolute pressure sensors, FIG. 2J exemplifies a fluidic MEM device comprising two valves, a differential pressure sensor, three absolute pressure sensors, and a temperature sensor, and FIG. 2K exemplifies a fluidic MEM device comprising two valves, a differential pressure (DP) sensor and a conductivity sensor;

FIGS. 4A to 4G schematically illustrate possible embodiments of the fluidic MEM device having resistive/piezoresistive sensing element(s), wherein FIG. 4A shows a sectional view of a possible embodiment of the MEM device having a chamber/channel and a membrane, FIG. 4B demonstrates arrangement of conducting lines/electrodes of a resistive transducing element formed on the membrane and electrical contacts (pads) thereof, FIG. 4C demonstrates a transducing element implemented by an electrically conducting line arranged to form a rectangular wave pattern, FIGS. 4D and 4E demonstrate a transducing element implemented by an electrically conducting line arranged in a zigzag wavy pattern, FIGS. 4F and 4G demonstrate a transducing element implemented by an electrically conducting line arranged to form a circular pattern;

FIGS. 5A to 5D demonstrate possible arrangements of the transducing elements for implementing a Wheatstone bridge in the fluidic MEM device;

FIGS. 6A to 6E schematically illustrate transducing sensing elements formed on the membrane of the MEM device according to some possible embodiments, wherein FIGS. 6A and 6B respectively show the membrane and electrodes of a capacitive transducing element formed on it in a resting state and in a deformed state, FIG. 6C demonstrates a Rosette-like circular arrangement of a capacitive transducer on the membrane, FIG. 6D exemplifies a parallel plate capacitive transducing sensor element employing conductive surfaces, and FIG. 6E exemplifies a MEM device having a capacitive transducer in a gas compartment of the device;

FIGS. 7A and 7B are sectional views of fluidic MEM device employing different types of differential pressure sensing elements according to possible embodiments, wherein FIG. 7A shows a MEM device having two chambers/channels used to implement the differential pressure sensor and FIG. 7B shows a MEM device usable for measuring differential pressure across a restrictor using two absolute pressure sensors;

FIGS. 8A to 8I are sectional views schematically illustrating a process suitable for fabricating a fluidic MEM device according to some possible embodiments;

FIGS. 10A to 10F show a possible configuration of the fluidic MEM device and arrangements for quick connection/disconnection to/from external devices/systems, wherein FIG. 10A shows a perspective view of the MEM device, FIG. 10B shows a sectional view of the MEM device, and FIGS. 10C to 10F exemplify possible mechanisms for connecting the MEM device to external systems;

FIGS. 11A to 11I exemplify structures and constructions of various possible embodiments of the fluidic MEM device, and arrangements for quick connection/disconnection to/from external devices/systems, wherein FIG. 11A to 11C show MEM device structure usable for measurement of fluid pressure and/or flow rate, FIG. 11D to 11F show another MEM device structure usable for measurement of fluid pressure and/or flow rate, FIG. 11G shows a sectional view of a MEM device structure usable for flow control and for measurement of fluid pressure and/or flow rate, and FIG. 11H and FIG. 11I exemplify a possible mechanism for connecting the MEM device to external systems/devices;

FIGS. 12A and 12B demonstrate attachment of a fluidic MEM device to a PCB according to possible embodiments, wherein FIG. 12A is an exploded view and FIG. 12B is a sectional view of the MEM device and of the PCB;

FIGS. 14A and 14B show a MEM device configured according to some possible embodiments to measure electrical conductivity of a fluid, wherein FIG. 14A is a perspective view and FIG. 14B shows a based portion of the device;

FIGS. 15A to 15F are perspective views demonstrating mass production of fluidic MEM devices using wafers according to some possible embodiments, wherein FIGS. 15A to 15C show rectangular wafers comprising arrays of MEM devices, FIGS. 15D and 15E show a circular wafer comprising an array of MEM devices, and FIG. 15F demonstrate a fabrication technique of a stack of wafers of MEM devices with a wafer holder assembly;

FIGS. 16A and 16B schematically illustrate another possible configuration of the fluidic MEM device according to some embodiments, wherein FIG. 16A shows a sectional view of the fluidic MEM device and FIG. 16B shows fabrication of a plurality of fluidic MEM devices.

DETAILED DESCRIPTION OF EMBODIMENTS

Figure 1A:
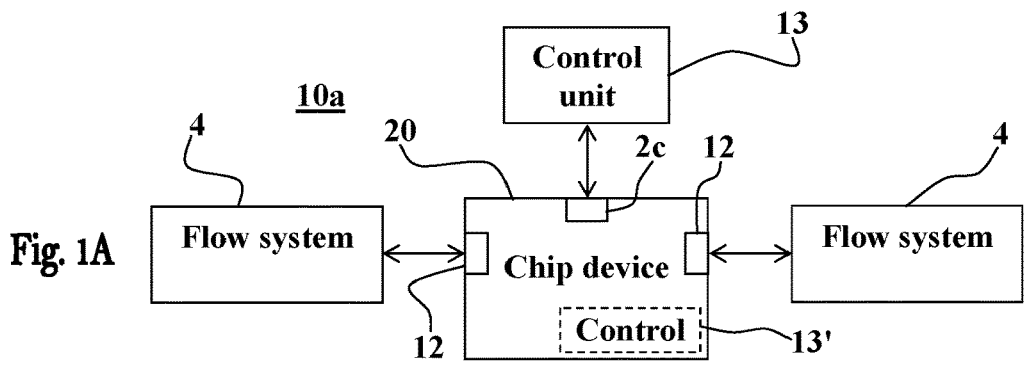
FIGS. 1A to 1D are block diagrams schematically illustrating fluid delivery systems according to some possible embodiments, wherein FIG. 1A exemplifies general structure of a fluid delivery system, FIG. 1B demonstrates a fluid delivery system utilizing a concatenated arrangement of a plurality fluidic MEM devices.

One or more specific embodiments of the present disclosure will be described below with reference to the drawings, which are to be considered in all aspects as illustrative only and not restrictive in any manner. In an effort to provide a concise description of these embodiments, not all features of an actual implementation are described in the specification. Elements illustrated in the drawings are not necessarily to scale, emphasis instead being placed upon clearly illustrating the principles of the invention. This invention may be provided in other specific forms and embodiments without departing from the essential characteristics described herein.

The present invention provides structures, arrangements, and manufacture techniques, of fluidic MEM devices implemented as small sized chips (e.g., having a length of about 1 to 50 mm, width of about 1 to 50 mm, and height of about 1 to 50 mm) having one or more fluid flow structures, sensing and/or actuating elements. The MEM device can be implemented as a monolithic device fabricated in a single process (e.g., molding, 3D printing, micro scale molding techniques, micro machining, nano and micro imprinting, hot embossing, injection molding, lithography, laser micromachining, and suchlike) to include all required fluid flow and sensing/actuating structures. Optionally, and in some embodiments preferably, the fluidic MEM device is configured and operable to be directly connected to external devices/systems and instantly establish electrical and/or fluid connection therewith.

FIGS. 1A to 1D are block diagrams schematically illustrating fluid delivery systems according to some possible embodiments. General structure of a fluid delivery system 10a is shown in FIG. 1A. In this non-limiting example the delivery system 10a comprises a fluidic MEM/chip device 20 (also referred to herein as MEM device) used to communicate fluid media between two flow systems 4 via fluid ports 12 thereof. A control unit 13 electrically and/or mechanically coupled to the MEM device 20 through connectors 2c (e.g., conductive pads, mechanical locking matching mechanism for connecting the device to the external control unit 13 and/or external mechanical actuation mechanism of the valves) provided on the MEM device, is used to monitor and/or regulate the fluid flow through the MEM device 20. As exemplified in FIGS. 1A to 1C, in possible embodiments control unit 13' may be integrated in the MEM device 20, and in this case the external control unit 13 may be removed if redundant.

Figure 1B:
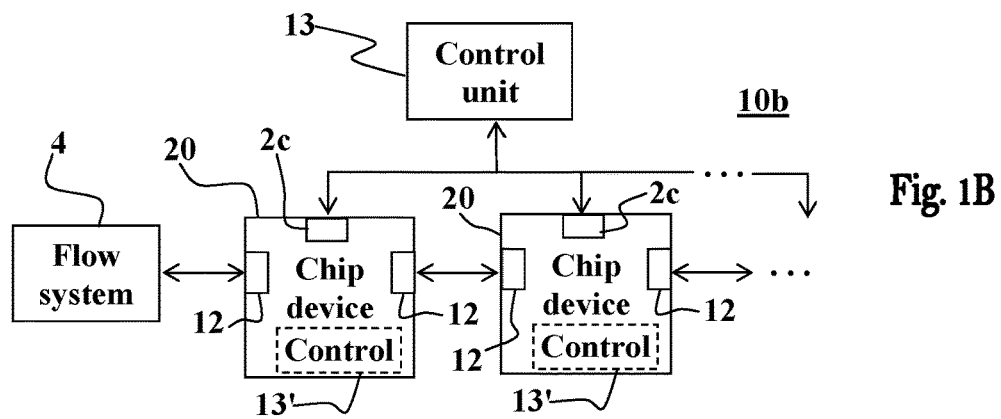

FIG. 1B demonstrates a fluid delivery system 10b utilizing a concatenated (serial) arrangement of a plurality fluidic MEM devices 20 serially connected to each other via their fluid ports 12 for monitoring and/or regulating the flow of the fluid media steamed from the flow system 4. The MEM device 20 at each end of this concatenated arrangement may be connected to a respective flow system 4 via its free fluid port 12. This arrangement of system 10b is particularly useful for monitoring fluid pressure in different points of a tube/line/pipe/channel. For example, and without being limiting, between two consecutive measurement points there may be an additional flow system or element, such as a filter or pump or restrictor that effects the flow parameters. In some cases, due to properties of the fluid media, only the concatenated system arrangement 10b can be used for monitoring and regulating the flowed fluid e.g., in medical applications wherein the monitored fluid media should not be steady, for instance if the fluid is blood, which should not be held steady in the system to prevent it from becoming clotted. Another advantage of the concatenated system arrangement 10b is that there is less risk of air getting trapped within the system.

Figure 1C:
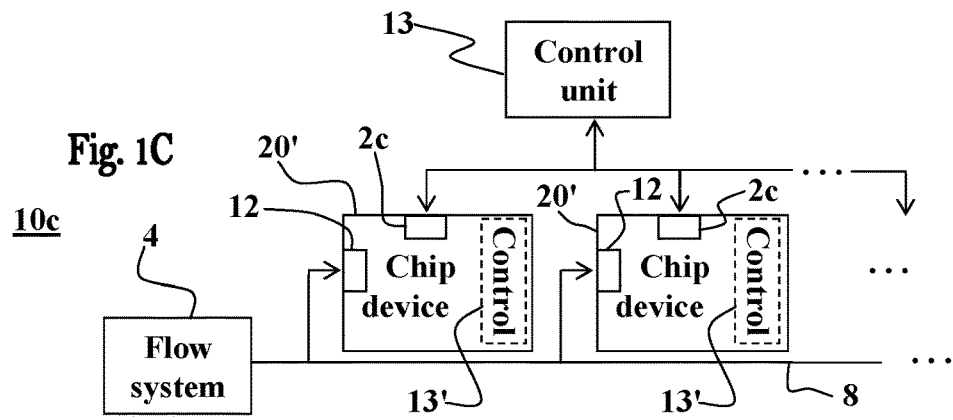

FIG. 1C shows a fluid delivery system 10c utilizing a plurality of fluidic MEM devices 20' for monitoring fluid media streamed into a fluid transfer line 8 by the fluid system 4. In this non-limiting example each MEM device 20' comprises a single fluid port 12 for communication of fluid media thereinto from the transfer line 8. Thus, in this example the MEM devices 20' are usable only for monitoring properties/conditions of the fluid media (e.g., fluid pressure) streamed through the line 8. In this system arrangement 10c the flow system is less (or not at all) effected from the presence of the MEM device 20'. This arrangement is usable in situations wherein the measurements should be double checked by introducing more than one sensing element, while not effecting the system, in order to achieve a more reliable and/or accurate measurements. Another advantage of the system arrangement 10c is that it allows replacing one of the MEM devices 20' while keeping the system 10c operable to monitor the fluid media by the sensing elements of the other MEM device 20'.

Figure 1D:
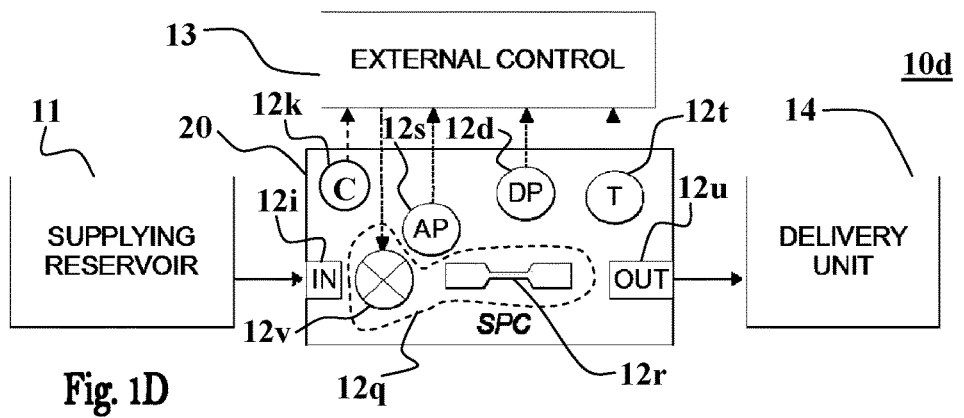

FIG. 1D depicts a fluid delivery system 10d using a fluidic MEM-device 20 to monitor and/or regulate fluid media flowing between a fluid supply system 11 and a fluid delivery unit 14 (e.g., a dispensing device). The MEM device 20 in this non-limiting example comprises a fluid flow regulating and monitoring arrangement 12q, one or more sensing elements, and at least one fluid inlet 12i and at least one fluid outlet 12u (only one inlet and outlet depicted in FIG. 1D). The regulating and monitoring arrangement 12q comprises a restrictor 12r (e.g., implemented by a constriction forming a slender fluid passage segment), and a controllable flow regulator (e.g., flow control valve) 12v. Fluid media supplied by the fluid reservoir 11 is introduced into the MEM device 20 via the at least one inlet 12i and transferred to the delivery unit 14 via the at least one outlet 12u of the fluidic MEM device 20. The control unit 13, electrically and mechanically (e.g., by a locking matching mechanism) coupled to the fluidic MEM device 20 (e.g., electrically via its contact pads), is used for monitoring and regulating the flow of the fluid media by processing measurement data/signals received front the sensing elements and generating control signals to change the state of the flow regulator 12v.

In some embodiments the coupling of the MEM device 20 to the external control system 13 is both mechanical and electrical. For example, a locking/matching mechanism may be used to establish electrical connection with the external control unit 13 and/or mechanical connection with mechanical actuators used to operate the flow regulator 12v.

The sensing elements provided in the MEM device 20 may be configured and operable for measuring one or more properties/conditions of the fluid introduced thereinto via the at least one inlet 12i. For example, and without being limiting, the MEM device 20 may comprise one or more pressure sensors 12s/12d for measuring pressure of the fluid media passing through the MEM device 20 and generating measurement data/signals indicative thereof, and/or one or more temperature sensors 12t for measuring temperature of the fluid media and/or one or more conductivity sensor and generating measurement data/signals indicative thereof. In particular, in this example the MEM device 20 comprises an absolute pressure sensor 12s, a differential pressure sensor 12d, an electrical conductivity sensor 12k, and a temperature sensor 12t. The pressure and temperature sensors are electrically coupled to the control unit 20 configured and operable to receive measurement data/signals from the sensor units, process and analyze (e.g., determine fluid flow rate) the received data/signals, and generate control signals for setting the state of the flow regulator 12v accordingly.

FIGS. 2A to 2K exemplify various possible embodiments of the fluidic MEM device 20. In FIG. 2A the MEM device 20a comprises a differential pressure sensor 12d configured and operable to measure differential pressure between a fluid flow path 12p upstream to the restrictor 12r and a slender fluid passage inside the restrictor 12r. In this non-limiting example two flow regulators are used to control the passage of the fluid through the MEM device 20a; a first flow regulator 12v located upstream to the flow restrictor 12r and a second flow regulator 12v' located downstream to the flow restrictor 12r.

In some possible embodiments upstream (12v) and downstream (12v') flow regulators are used in the MEM device to improve safety/reliability e.g., if one flow regulator malfunctions the fluid flow can be still controlled by the second regulator. In addition, this configuration also permits measuring the fluid pressures in the input and output channels in states wherein there is no fluid flow in the device, by measuring the pressure when only one of the flow regulators is open. Furthermore, the use of such two flow regulators provides for safety controls e.g., in situations wherein the input pressure has to be higher than the output pressure and/or where the input and output pressures should be within a predetermined safety range required by certain application needs.

FIG. 2B demonstrates a fluidic MEM device 20b which configuration is substantially similar to that of MEM device 20a shown in FIG. 2A, and further comprising a temperature sensor 12t configured and operable to measure temperature of fluid passing through the fluid flow path of the restrictor 12r and generate data/signals indicative thereof. In some possible embodiments measurement data received from the temperature sensor 12t is used by the control unit (13) to compensate for temperature effects in the flow measurement data from the pressure sensor(s) 12d. FIG. 2C demonstrates a MEM device 20c which configuration is substantially similar to that of MEM device 20b shown in FIG. 2B, but without the flow regulators 12v i.e., this configuration can be used in certain embodiments requiring only measurement/monitoring fluid conditions (e.g., flow rate, pressure, temperature) without flow control/regulating.

The configuration of MEM device 20d shown in FIG. 2D is substantially similar to MEM device 20b shown in FIG. 2B but having two absolute pressure sensors 12s instead of the differential pressure sensor 12d. In this non-limiting example a first absolute pressure sensor 12s^ is configured and operable to measure fluid pressure in fluid flow path 12p upstream to the fluid restrictor 12r and generate measurement data/signals indicative thereof, and a second absolute pressure sensor 12s is configured and operable to measure fluid pressure in a slender fluid passage formed inside the fluid restrictor 12r, and generate measurement data/signals indicative thereof. This configuration of MEM device 20d may be used in certain embodiments using the control unit 13 to determine fluid flow rate through the MEM device based of the measurement data received from the absolute pressure sensors 12s and 12s^.

It is noted that the use of absolute pressure sensors 12s as exemplified in FIG. 2D may be used to implement additional device controls functionalities, such as, but not limited to: disconnection of input and output flow paths/channels, verification of absolute pressure in the input channel (the flow path between the inlet 12i and the restrictor 12r) and/or output channel (the flow path between the outlet 12u and the restrictor 12r) and within the MEM device 20.

FIGS. 2E and 2F exemplify possible embodiments wherein absolute pressure sensors 12s are used together with a differential pressure sensor 12d in MEM devices having a upstream flow regulator 12v and an downstream flow regulator 12v'. The configuration of MEM device 20e shown in FIG. 2E is substantially similar to that of MEM device 20a shown in FIG. 2A but further comprises the following absolute pressure sensors: a first absolute pressure sensor 12s configured and operable to measure fluid pressure in a slender fluid flow path inside the fluid restrictor, and generate measurement data/signals indicative thereof; a second absolute pressure sensor 12s' configured and operable to measure fluid pressure in a fluid flow path downstream to the flow restrictor 12r (i.e., between the restrictor 12r and the downstream flow regulator 12v') and generate measurement data/signals indicative thereof; and a third absolute pressure sensor 12s'' configured and operable to measure fluid pressure in a fluid flow path downstream to the flow regulator 12v' (i.e., between the flow regulator 12v' and the outlet 12u of the device 20e) and generate measurement data/signals indicative thereof.

The configuration of MEM device 20f shown in FIG. 2F is substantially similar to that of MEM device 20b shown in FIG. 2B but further comprising three absolute pressure sensors 12s, as follows: a first absolute pressure sensor 12s^x configured and operable to measure fluid pressure in the fluid flow path between the inlet 12i of the device 20f and the upstream flow regulator 12v and generate measurement data/signals indicative thereof; a second absolute pressure sensor 12s' configured and operable to measure fluid pressure in a fluid flow path downstream to the flow restrictor 12r, and generate measurement data/signals indicative thereof; and a third absolute pressure sensor 12s'' configured and operable to measure fluid pressure in a fluid flow path downstream to the downstream flow regulator 12v', and generate measurement data/signals indicative thereof.

The configurations of the MEM devices 20e and 20f are particularly useful for improving resolution/precision of the fluid flow rate determined based on the absolute pressure measurement data, and for obtaining absolute pressure measurement data indicative of fluid pressure at the input channel, at the output channel, and across the restrictor $12r$, independent of the state of the flow regulators $12v$ and $12v'$. It is noted that these configurations are also useful for double checking the determined fluid flow rate by comparing the measurement data obtained from the differential pressure sensor $12d$ and to the measurement data obtained from the absolute pressure sensors $12s/12s^x$, $12s'$ and/or $12s''$.

FIGS. 2G and 2H exemplify possible embodiments wherein one or more concatenated upstream flow regulators $12v$ are used in the input channel and two or more concatenated downstream flow regulators $12v'$ are used in the output channel of the MEM device, and absolute pressure is measured at the output channel and in between the pairs of concatenated upstream/downstream flow regulators. The configuration of MEM device $20g$ shown in FIG. 20G is substantially similar to that of MEM device $20a$ shown in FIG. 2A, but comprising two concatenated downstream flow regulators $12v'$ between the flow restrictor $12r$ and the outlet $12u$ (instead of just one), and further comprising two absolute pressure sensors $12s$; a first absolute pressure sensors $12s'$ configured and operable to measure fluid pressure in a fluid flow path between the two downstream flow regulators $12v'$ and generate measurement data/signals indicative thereof, and a second absolute pressure sensors $12s''$ configured and operable to measure fluid pressure in a downstream fluid flow path between the flow regulators $12v'$ and the outlet $12u$ of the device $20g$ and generate measurement data/signals indicative thereof.

The configuration of MEM device $20h$ shown in FIG. 2H is substantially similar to that of MEM device $20b$ shown in FIG. 2B, but comprising two concatenated downstream flow regulators $12v'$ between the flow restrictor $12r$ and the outlet $12u$ (instead of just one), two concatenated upstream flow regulators $12v$ between the flow restrictor $12r$ and the inlet $12i$ (instead of just one), and further comprising three absolute pressure sensors $12s$. A first absolute pressure sensor $12s'$ is configured and operable to measure fluid pressure in a fluid flow path between the two downstream flow regulators $12v'$ and generate measurement data/signals indicative thereof, a second absolute pressure sensor $12s^{x}$ is configured and operable to measure fluid pressure in a fluid flow path between the two upstream flow regulators $12v$ and generate measurement data/signals indicative thereof, and a third absolute fluid pressure sensor $12s''$ configured and operable to measure fluid pressure in a fluid flow path between the downstream flow regulators $12v'$ and the outlet $12u$ of the device $20h$ and generate measurement data/signals indicative thereof.

FIGS. 2I and 2J exemplify possible embodiments having only the downstream flow regulators $12v'$ in the output channel. As seen, the input channel between the inlet $12i$ of the devices $12i$ and $20j$ and their restrictors $12r$ do not include neither sensor units nor flow regulators. As seen, the configuration of MEM device $12i$ shown in FIG. 2I is substantially similar to that of MEM device $20g$ shown in FIG. 2G, but without the upstream flow regulator $12v$, and the configuration of MEM device $20j$ shown in FIG. 2J is substantially similar to that of MEM device $20h$ shown in FIG. 2H, but without the two concatenated upstream flow regulators $12v$ and the absolute pressure sensor $12s^{x}$ between them.

FIG. 2K demonstrates a MEM device $20k$ with configuration substantially similar to that of MEM device $20a$ shown in FIG. 2A, and further comprising an electrical conductivity sensor $12k$ configured and operable to measure electrical conductivity in a part of the fluid flow path downstream to the restrictor $12r$. Of course, the conductivity sensor may be positioned in any other part of the fluid flow path e.g., in the restrictor $12r$ or in a part of the fluid flow path upstream to the restrictor $12r$. In some embodiments the measured conductivity is used to determine the type of fluid introduced into the MEM device $20k$. In addition the measured conductivity can also be useful to detect presence of air (or other gases) i.e., if air is present in the fluid chamber/channel there is no electrical current passing through the conductivity sensor $12k$.

It is noted that temperature sensors $12t$ of the MEM device may be placed anywhere along the fluid flow path of the MEM device, not limited to its restrictor $12r$ section. Optionally, and in some embodiments preferably, the temperature sensors $12t$ are situated at the restrictor $12r$ for measuring the fluid temperature in the restrictor in order to calculate/verify the fluid flow rate. In certain applications it is important to monitor the fluid pressure inside the MEM device to prevent high pressure conditions thereinside. The system utilizing the MEM device may be thus configured to issue an alarm (e.g., by the control unit $13$) whenever the measurement data obtained from the sensor elements indicates that the fluid pressure conditions in the MEM device are greater than some predetermined allowable pressure level.

Flow sensors for measuring flow rate of fluid media through the MEM device $20$ may be implemented using one or more pressure sensors, the fluid channel $12p$ and the restrictor $12r$ formed therein. The flow of the fluid media is related to the pressure difference across the restrictor which can be measured using a differential sensor pressure $12d$, two gauge pressure sensors AP, or two sealed pressure sensors (will described herein below). Combinations of these pressure sensor elements can be use to implement additional and safety controls such as (e.g., for detection of air/gas bubbles, output pressure out of range—if too high there could be an obstruction and if too low the delivery system could be disconnected, input pressure out of range—if too low relative to the output pressure there could be a reflow, and if too high could damage the MEM device and the fluid media may not be delivered according to specification).

The flow regulators $12v/12v'$ in the different configurations shown in FIG. 2 may be used to implement flow control schemes for the MEM device. The flow regulators can be controlled mechanically or electromagnetically by the external (or integrally embedded $13'$) control unit $13$, which may be configured and operable to measure the fluid flow rate through the MEM device and adjust the state of the flow regulators accordingly to regulate the amount of fluid media delivered through the device.

Figure 3A:
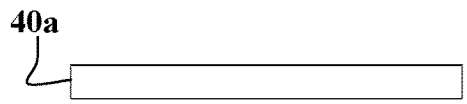
FIGS. 3A to 3H schematically illustrate a manufacture process of a fluidic MEM device according to some possible embodiments.
Figure 3B:
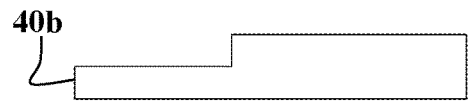
Figure 3C:
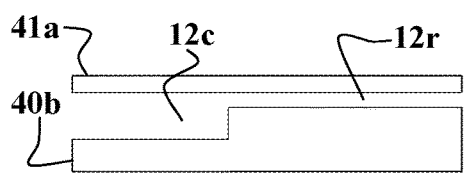

FIGS. 3A to 3H schematically illustrate a process for fabricating a fluidic MEM device ($20$) according to some embodiments. In FIG. 3A an initial substantially flat base layer $40a$ is prepared from a base-material (e.g., from a polymeric or any other suitable material) for deposition of layered structures/patterns thereon. The thickness of the base layer $40a$ may generally be about 0.1 to 5 mm. In FIG. 3B one or more base-material patterns (e.g., having total thickness of about 0.2 to 10 mm) are deposited on the base layer $40a$ to provide a predetermined geometrical shape for a base structure $40b$ of the device. Thereafter, a thin base-material layer $41a$ is deposited above the base structure $40b$ so as to define one or more fluid channels $12c$ (only one fluid channel is shown in FIG. 3) having one or more restrictors $12r$, and providing a build-layer for formation of one or more membranes ($47m$, $48m$ and $49m$, in FIG. 3E).

As seen, a restrictor 12r may be implemented by a constriction forming a slender fluid passage by the one or more base-material patterns deposited in FIG. 3B on the base layer 40a. The thickness of the thin layer 41a may generally be about 0.01 mm to 1.5 mm. In some embodiments, a sacrificial supportive layer (not shown in FIG. 3) is used for depositing the thin base-material layer 41a above the base structure 40b, which is thereafter removed to build the fluid channel 12c and its restrictor 12r. Alternatively, the design and fabrication process may be configured to allow the deposition of the thin base-material layer 41a without a sacrificial layer.

In FIGS. 3A to 3H the MEM device is constructed to include a single fluid channel 12c having a single restrictor 12r. In possible embodiments the cross-sectional area of the fluid channel 12c may be about 0.0005 mm$^2$ to 70 mm$^2$, and the cross-sectional area of its restrictor 12r may be about 0.0002 mm$^2$ to 70 mm$^2$.

Figure 3D:
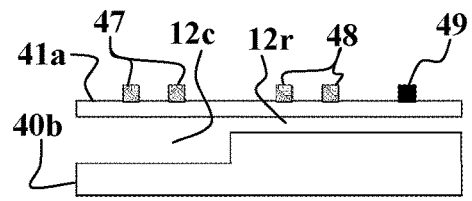
Figure 3E:
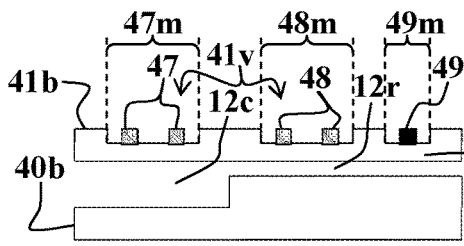

Next, as illustrated in FIG. 3D, electrically conductive and/or mechanically actuable (i.e., mechanically operated), elements are deposited in one or more layers on top of the thin layer 41a e.g., by electroplating, electroforming, printing, evaporation, sputtering, or electroless plating, or electropolymerization. For example, and without being limiting, the elements deposited on the thin layer 41a may comprise electrically conducting lines/contacts and/or flow regulators bosses, formed by depositing predetermined metallic patterns (e.g., having thickness of about 0.0001 to 0.2 mm). FIG. 3D specifically exemplifies formation of two electrodes 47 and 48, and an actuable boss 49. In FIG. 3E one or more base-material patterns 41b are deposited on top of the thin layer 41a to form a predetermined pattern having one or more void areas 41v (i.e., areas over thin layer 41a not covered by layer 41b) defining the membranes of the MEM device. The one or more base-material patterns 41b are deposited such that the electrically conductive/actuable elements 47, 48 and 49, are obtained in at least one of the void areas 41v, or as exemplified in FIGS. 3E and 3F, electrodes 47 and 48 are obtained inside the void areas 41v of membranes 47m and 48m, respectively, and actuable element 49 is obtained inside the void area 41v of membranes 49m. The thickness of the one or more base-material patterns 41b surrounding the electrically conductive/actuable elements 47, 48 and 49, may be substantially of the same thickness as that of said electrically conductive/actuable elements 47, 48 and 49.

Figure 3F:
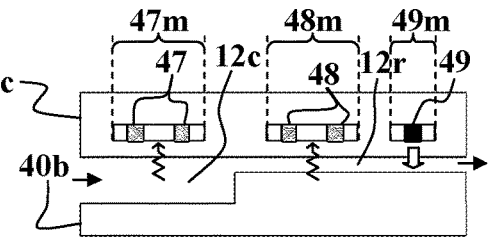

In FIG. 3F one or more base-material layers 41c are deposited on top of the base-material patterns 41b, and above/over the electrically conductive/actuable elements 47, 48 and 49, encapsulating the electrically conductive/actuable elements of the device, thereby isolating the conductive/actuable elements and finalizing the fabrication process of the MEM device. The thickness of the base-material patterns 41b may generally be about 0.1 to 2 mm, and in some possible embodiments about 0.0002 to 2 mm. The MEM device can be used to measure and/or regulate fluid flowed through it fluid channel(s) 12c. Horizontal arrowed lines shown in FIG. 3F illustrate passage of a fluid media streamed into the fluid channel 12c. Zigzagged arrowed lines illustrate in FIG. 3F fluid pressure applied over the membranes 47m and 48m due to the passage of the streamed fluid.

A vertical rectangular-shaped arrow illustrates in FIG. 3F represent deformation of membrane 49m downwardly by the actuable element 49 for regulating the fluid flow through the channel of the device by changing cross-sectional area of fluid flow path inside the restrictor 12r. The different membranes 47m, 48m and 49m are preferably made elastically (reversibly) deformable, for restoring their resting state shape whenever no actuating forces/fluid pressure conditions are being applied on them. Also as seen in FIG. 3F, a first pressure sensor implemented by membrane 47m and its electrodes 47 is configured and operable to measure the fluid pressure in the fluid channel 12c, and a second pressure sensor implemented by membrane 48m and its electrodes 48 is configured and operable to measure the fluid pressure in the restrictor 12r.

Figure 3G:
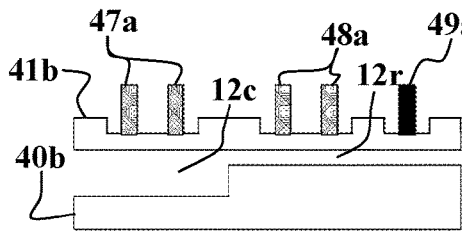
Figure 3H:
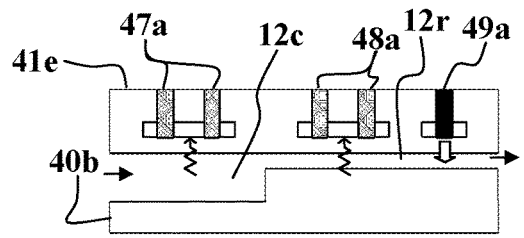

With reference to FIGS. 3G and 3H, in an alternative fabrication process the step of depositing of the electrically conductive and/or mechanically actuable elements (shown in FIG. 3D) is repeated a predetermined number of times within patterned grooves inside a previously deposited base-material 41e (seen in FIG. 3H), the grooves substantially encompassing the deposited electrically conductive and/or mechanically actuable elements. In this way electrically conducting pillars (vias, e.g., having height of about 0.001 to 2 mm) 47a, 48a and 49a, are formed contained encapsulated within the one or more layers of the base-material patterns 41e.

In the configuration demonstrated in FIGS. 3G and 3H larger conductive/actuable elements structures are prepared, which can be exploited electrically or mechanically, e.g., to improve robustness, or different conductivity properties, or to yield more complex shapes. In some embodiments a sacrificial supportive material is used in the steps shown in FIG. 3G, which are later removed, e.g., using lithography techniques. In the non-limiting example shown in FIG. 3H the base structure 40b or the base-material patterns 41e is used as both a structural material and a supportive material for the process.

It is important to note that the encapsulation of the MEM device by the layers 41c in FIG. 3F, and/or 41e in FIG. 3H, could be also carried out using a type of polymer different from that used for the base-material patterns 41b, e.g., Polydimethylsiloxane (PDMS), Parylene.

Figure 4A:
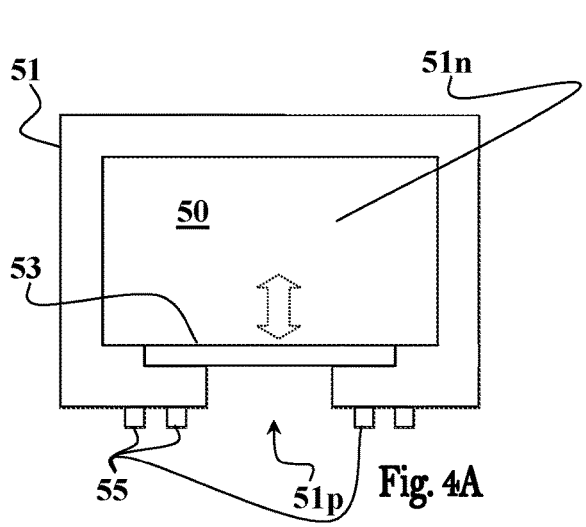

FIGS. 4A to 4G schematically illustrate possible embodiments of the fluidic MEM device having resistive/piezoresistive sensing element(s). With reference to FIG. 4A, wherein there is shown a cross-sectional view of a fluidic MEM device 50 fabricated as a single monolithic unit having a solid (massive) body 51 comprising electrical contact pads 55 deposited over an external surface area thereof to provide electrical connectivity with external devices/units and/or systems e.g., for pressure measurement. The MEM device 50 comprises a fluid chamber or channel 51n and a membrane 53 sealably mounted inside the chamber/channel 51n over an opening 51p formed in one of the walls of the device.

As will be described and illustrated hereinbelow, the membrane 53 is preferably made sufficiently elastic to permit deformations thereof towards/into the opening 51p responsive to fluid pressure conditions evolving inside the fluid chamber/channel 51n. The contact pads 55 are electrically coupled to transducing elements of the sensing means (not shown in FIG. 4A) formed over the membrane 53 to thereby permit an external device/system (not shown) coupled to the MEM device 50 to obtain measurement data/signals from its sensor(s).

Figure 4B:
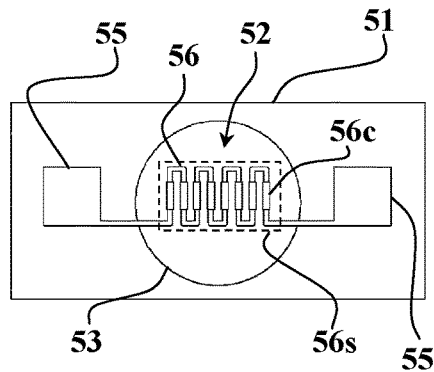

FIG. 4B demonstrates possible arrangement of electrically conducting lines of a resistive transducing element 52 formed on the membrane 53 of the MEM device 50, and electrical contacts (pads) thereof. In this specific and non-limiting example, the transducing elements 56 formed on the membrane 53 comprises either resistive and/or piezo-resistive transducing elements 56c mechanically coupled to the membrane 53 and electrically connected to the contact pads 55 of the MEM device for measuring at least one condition or property (e.g., pressure) of a fluid introduced into, or passed through, the fluid chamber/channel 51n (e.g., in response to deflection of the membrane 53). For example, and without being limiting, the transducing elements 56c may be prepared from an electrically conducting material, such as, but not limited to, Gold (Au), Copper (Cu), Platinum (Pt), Aluminum (Al), Nickel (Ni) or theirs alloy, deposited on the membrane surface e.g., printing, sputtering, evaporation, electroforming.

Figure 4C:
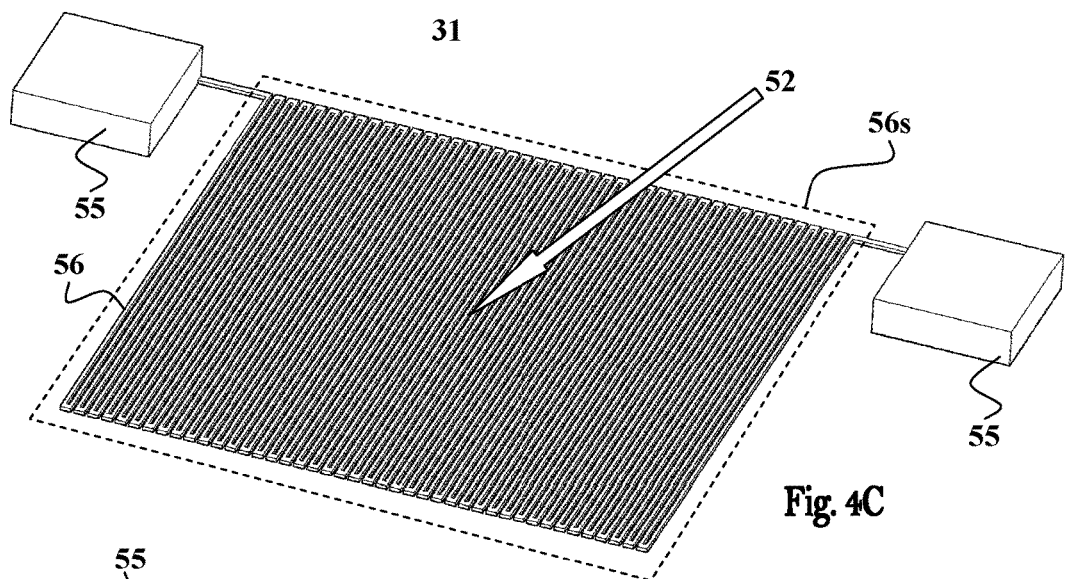

As seen in FIG. 4B and further demonstrated in FIG. 4C the transducing element may be implemented by an electrically conducting line arranged to form a dense rectangular wave-like pattern to maximize the length of the electrically conducing lines 56 traversing the surface of the membrane 53 and thereby substantially improve the sensitivity of the resistive transducing element 52.

For example, and without being limiting, in possible embodiments the thickness of the electrically conducing lines 56 may be about 0.0001 to 0.05 mm, and the distance between adjacently located electrically conducing lines 56 may generally be about 0.0001 to 0.1 mm. It is noted that while FIGS. 4B and 4C demonstrate rectangular configuration 56s of rectangular wave like patterns formed by the electrically conducing lines 56, other geometrical shapes are also possible, such as, but not limited to, circular, half-circle, elliptical, polygon, etc.

Figure 4D:
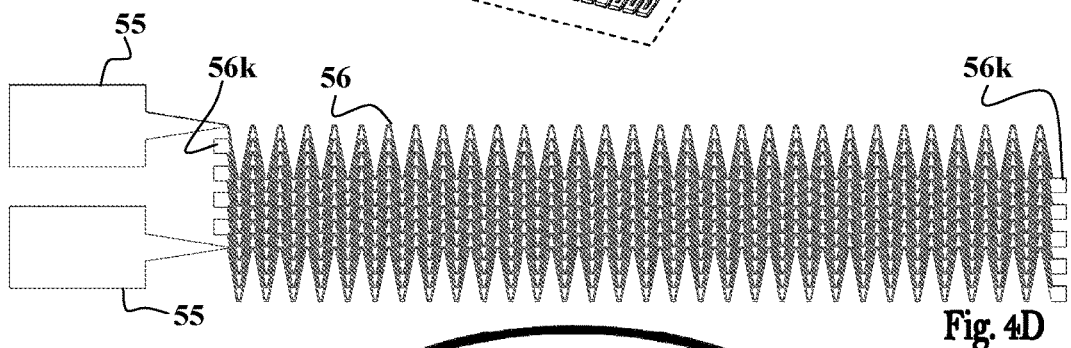
Figure 4E:
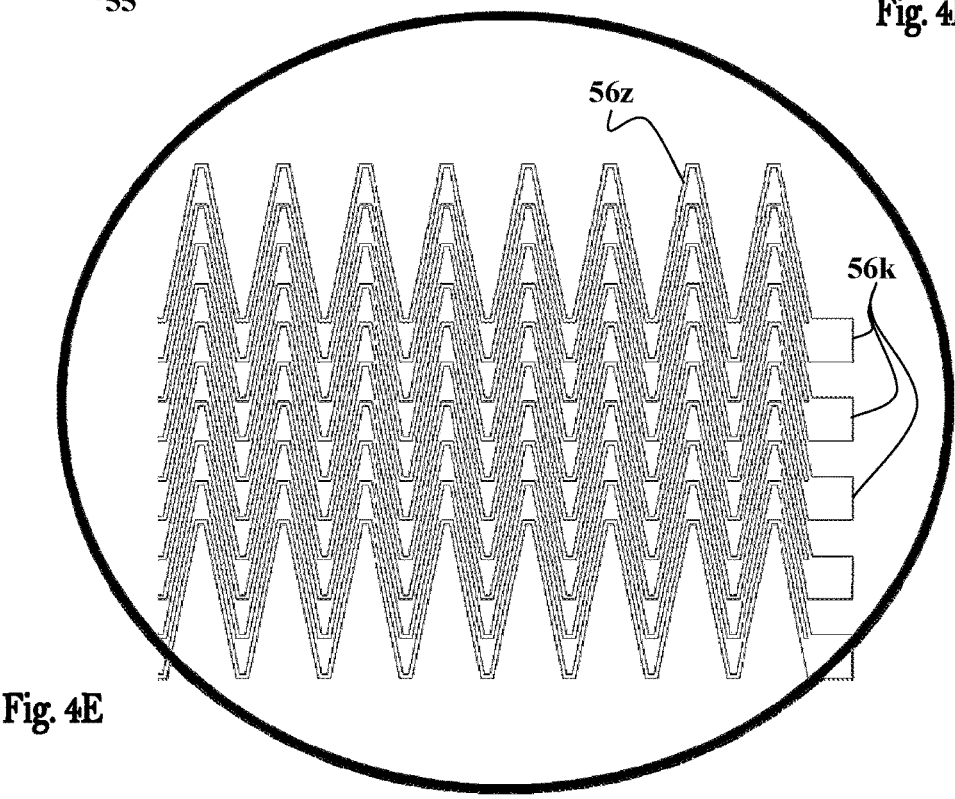

FIGS. 4D and 4E demonstrate arranging the electrically conducing lines 56 of the resistive transducing element 52 to form a plurality of zigzag (e.g., sine-wave like or saw-shaped) patterns 56z, according possible embodiments. The zigzag patterns 56z of electrically conducing lines 56 are successively arranged in close proximity to maximize the length of the conducing lines 56 and the membrane area covered by resistive transducing element 52. Each zigzag pattern 56z may be electrically connected to an adjacently located zigzag pattern by a contact pad 56k, to thereby electrically link the plurality of zigzag patterns 56z to form a substantially long electrically conducting line so as to maximize the membrane area covered by the resistive transducing element 52 and improve its sensitivity. The thickness of the electrically conducting line 56, and the distance between adjacently located zigzag patterns 56z may be within the same ranges indicated above with reference to FIGS. 4B and 4C.

FIGS. 4F and 4G demonstrate a circular arrangement (e.g., Rosette type) of the resistive transducing element 52. In this non-limiting example the electrically conducting lines 56 form a plurality of adjacently located arc-shaped patterns 56p, where each arc-shaped pattern 56p is enclosed between, and electrically connected to, at least one inner arc-shaped pattern 56p and at least one outer arc-shaped pattern 56p (except for innermost and outermost arcs), thereby obtaining a substantially half circle geometrical shape of the resistive transducing element 52. In this way the length of the electrically conducting line 56, and the membrane area it covers, are significantly maximized so as to improve the sensitivity of the resistive transducing element 52. The thickness of the electrically conducting line 56, and the distance between adjacently located arc-shaped patterns 56p may be within the same ranges indicated above with reference to FIGS. 4B and 4C. In a possible embodiment the radius R of the half-circle shape formed by the resistive transducing element 52 may be about 0.05 to 5 mm.

FIGS. 5A to 5D demonstrate possible arrangements of the resistive sensing elements for implementing a Wheatstone bridge circuitry in the fluidic MEM device. With reference to FIG. 5A, four resistive elements may be patterned over surface areas of the MEM device 20, R1, R2, R3 and R4. At least one element patterned over the deformable area of the membrane 53 (e.g., R1) is used as a sensing element, while the other elements patterned on other parts of the MEM device 20 (non-deformable or low-deflection regions) of the membrane 53 are used as dummy elements. In this way temperature and other possible effects that may influence the measurements are compensated.

In the non-limiting example shown in FIG. 5A the sensing elements R1 and R2 are formed over the deformable area of the membrane and the dummy elements R3 and R4 are used for temperature compensation and zero offsetting. Placing the two sensing elements R1 and R2 over the deformable region of the membrane 53 improves (doubles) the sensitivity of the sensor. It is noted that in possible embodiments the dummy elements R3 and R4 may be located external to the MEM device (e.g., in the control unit). The Wheatstone bridge connections can be completed external to the MEM device 20 using the circuitry configuration shown in FIG. 5C, or in some embodiments on the MEM device, as demonstrated in FIG. 5D.

In this way changes in the electrical resistance(s) of the sensing elements formed over the deformable regions of the membrane 53 may be measured using the Wheatstone bridge configuration 58 e.g., shown in FIG. 5B, and the measured signals/data obtained from the Wheatstone bridge circuit 58 (Vout) may be used by the control unit (13) to determine the pressure of the fluid media streamed through (or contained in) the MEM device 20. In possible embodiments the (dummy) sensing elements formed on the non-deformable (or low deflection) regions of the membrane 53 may be also used to implement a temperature sensor.

For example, the dummy resistors may be made from materials exhibiting specific resistance changes responsive to temperature changes (e.g., Gold (Au), Copper (Cu), Platinum (Pt), Nickel (Ni), and suchlike), which may be used as resistance temperature detectors (RTD). Such dummy resistors are preferably placed in areas not affected by the membrane deformations (or of low deformation), such that the main effect of their resistance change is due to temperature. In this case external switching circuitry (not shown) can be used to allow reading only the electrical resistance of a single resistor. The resistor reading could be done by 2, 3 or 4, point reading technique according to the accuracy needed.

In some embodiments the control unit 13 may be configured to implement a switching module capable of measuring the resistance of each sensing element separately (e.g., two terminals reading, three terminals reading or four terminals readings) according to the sensor configuration implemented in the MEM device 20. Such configuration permits self-test capability and enables verifying the correct insertion of the MEM device in its connections slot. The control unit 13 may be also configured to manipulate the resistors connections and establish a desired Wheatstone measurement circuitry configuration according to the needed measurement data (e.g., to implement a zero offset compensation scheme). The control unit may be also configured to present additional resistor elements into the measurement circuitry to establish a desired Wheatstone bridge configuration (e.g., add parallel or serial resistors to one or more of the elements formed on the MEM device to balance the Wheatstone bridge).

FIGS. 6A to 6C schematically illustrate possible embodiments of capacitive transducing sensing elements 52c that may be formed on the surface of the membrane 53 of the MEM device 20. FIGS. 6A and 6B are sectional views of a MEM device membrane showing the membrane 53 and high aspect ratio electrodes 57 of the transducing element 52c patterned on the membrane. FIG. 6A shows the membrane 53 in a resting state (i.e., when pressure is not applied over it), having a plurality of electrode pairs (for the sake of simplicity only three such electrode pairs depicted in FIGS. 6A and 6B), each comprising a reference electrode 57a and a sensing electrode 57b (generally referred to herein as electrode pair 57). Total capacitance of the electrodes in the resting state, as measured via the contact pads (55), may be used as a reference for fluid pressure measurement. In FIG. 6B the membrane 53 is elastically deformed/deflected (due to application of fluid pressure) and the distance between the reference and sensing electrodes in one or more (e.g., depending on the amount of applied pressure) of the electrode pairs is changed in response, thereby changing the total capacitance measurable via the contact pads. In this way a measure of the fluid pressure inside the chamber/channel (51n) of the MEM device 20 may be obtained according to the capacitance measured between the contact pads of the MEM device 20.

FIG. 6C schematically illustrates a possible electrode arrangement of a capacitive sensor element 52c arranged over the membrane 53 of the MEM device 20 according to some possible embodiments. In this non-liming example a plurality of substantially round high aspect ratio electrode pairs are coaxially arranged on (or in) the membrane 53. More particularly, in this non-limiting example each sensing electrode 57b is arranged to form an open loop ("C"-like shape) structure enclosing/encircling a respective adjacently located reference electrode 57a also having an open loop shape. The openings of the open loop shaped sensing electrodes 57b are facing one side of the plane of the membrane 53 (in which the contact pad 55a of the reference electrodes is disposed) for passage of electrically conducting lines connecting between the reference electrodes 57a and the contact pad 55a. Similarly, each reference electrode 57a (except the last one, which is in a form of a complete circle) is also arranged in a form of an open loop ("C"-like shape) structure enclosing another pair of adjacently located sensing and reference electrodes. The openings of the open loop shaped reference electrodes 57a are facing the other side of the plane of the membrane 53 (in which the contact pad 55b of the sensing electrodes is disposed) for passage of electrically conducting lines connecting between the sensing electrodes 57b and the contact pad 55b.

As exemplified in FIGS. 6A and 6B, the elastic deflection of the membrane 53 due to fluid pressure changes the distance between at least one of the open-loop adjacently located electrode pairs 57a and 57b, resulting in a measurable change in the capacitance of the capacitive sensor element 52c. It is understood that the high aspect ratio sensing (57b) and reference (57a) electrodes are substantially parallel to each other, and that the measured capacitance of the sensing element in the resting state of the membrane refers to zero pressure difference between the two sides of the membrane 53. It is also understood that the concentric adjacently located electrode pairs may be arranged to form various different open-shaped geometrical shapes, not necessarily round/circular e.g., elliptical, triangular, rectangular, polygon, and suchlike, mutatis mutandis, and that the electrode pairs may be arranged such that the sensing electrode 57b is enclosed by the open-shape structure of the reference electrode 57a.

The high aspect ratio electrode pairs 57 may be fabricated from, but not limited to, Gold (Au), Copper (Cu), Nickel (Ni), Aluminum (Al), or Platinum (Pt), or combinations thereof (e.g., applied by electrodeposition, electroforming, electroplating, electroless deposition). In some embodiments a thin adhesion improving layer (e.g., made of Chrome (Cr) and/or Titanium (Ti)) is used to improve the adhesion of the metal electrodes, conducting lines and/or contacts, to the polymer surface of the MEM device. In addition, a surface treatment to the polymer surface of the MEM device may used to improve adhesion of the metal electrodes, conducting lines and/or contacts, thereto e.g., by oxygen plasma. The aspect ratio (the ratio between the height and the width) of the electrodes 57 in some embodiments may be about 1 to 50, and the distance between each electrode pair 57 may be about 0.001 to 0.02 mm.

It is noted that electrically conducting lines 56, and/or the electrodes 57, of the sensing elements exemplified hereinabove may be formed on either the inner side (i.e., inside the fluid chamber/channel 51n of the MEM device) or the outer side of the membrane 53. In such embodiments wherein the conducting lines 56 and/or electrodes 57 are formed on the inner side of the membrane 53 they may be coated by one or more layers of electrically insulating materials (e.g., PDMS, Parylene C) to electrically isolate them from the fluid media inside the chamber/channel and protect them from causes of degradation (e.g., humidity, oxygen).

FIG. 6D shows a sectional view of a MEM device 50a having a body 51f and a capacitive sensor element 52g with parallel plates configuration. As seen, in this non-limiting example only one of the electrodes is placed on (or in) the membrane 53. Particularly, the sensing electrode 57x is arranged on (or in) the membrane 53 of the device, and the reference electrode 57y is placed on (or in) a surface area inside the chamber/channel 55f of the MEM device, opposite to the membrane 53. In this configuration a gap g formed between the reference and sensing electrodes is defined by the geometrical dimensions of the chamber/channel 55f of the MEM device 50a.

FIG. 6E exemplifies a MEM device 50e having a capacitive pressure sensor 52u. The MEM device 50e comprises a hollow body 51q having a fluid chamber/channel 55f for holding/streaming fluid media, and a gas compartment 55t filled with gas (e.g., air). An elastically deflectable membrane 53 sealably separates between the fluid chamber/channel 55f and the compartment 55t. One side of the membrane 53 is thus facing the fluid chamber/channel 55f, and contacts the fluid media in it, and its other side is facing the gas compartment 55t.

The capacitive pressure sensor 52u comprises two parallel electrically conducting plates/surfaces, a first electrically conducting surface 57q is provided on a surface of the membrane 53 facing the gas compartment 55t, and a second electrically conducting surface 57q is provided on an inner surface of the compartment 55t that is facing, and opposite to, the membrane 53, such that a gap g (e.g., of about 0.0005 to 0.1 mm) is obtained between the parallel electrically conducting surfaces 57q and 57t.

When pressure conditions evolve inside the chamber/channel 55f of the MEM device 50a the membrane 53 is deflected due to pressure difference between the two sides of the membrane 53. In the deflected state of the membrane 53 the high aspect ratio electrodes are not parallel. As the sensing electrode 57q is deformed responsive to the membrane deflection (reference electrode 57t does not deform), resulting in change of the dielectric gap g and corresponding change in the measurable capacitance of the sensor element 52g. The electrodes 57q and 57t may be fabricated from Gold (Au), Copper (Cu), Nickel (Ni), Aluminum (Al), or Platinum (Pt), or combinations thereof (e.g., applied by electrodeposition, electroforming, electroplating, electroless deposition). In some embodiments a thin adhesion improving layer e.g., made of Titanium (Ti) and/or Chrome (Cr), is applied to the surface of the MEM device to increase the adhesion of the metal electrodes, conducting line and/or contacts, thereto. In addition, a surface treatment may be applied to the polymer surface of the device to improve the adhesion of the electrodes, conducting lines and/or contacts, thereto e.g., by oxygen plasma.

In some possible embodiments the surface area (conductive layers) of each one of the electrodes 57q and 57t is about 0.5 to 50 mm$^2$. Optionally, and in some embodiments preferably, the distance g between the electrodes 57q and 57t in the resting state of the membrane 53 is about 0.0005 to 0.1 mm, for providing a suitable measurable capacitance range of the sensor element 52g. Optionally, and in some embodiments preferably, the electrodes 57q and 57t are coated by one or more dielectric insulating material (e.g., PDMS, Parylene C) to prevent electrical contact with the fluid media passed through/contained in the MEM device or protect them from causes of degradation (e.g., humidity, oxygen).

In some embodiments the electrodes 57q and 57t are not coated by an electrically insulating material and thus in touch/electrical contact with the fluid media inside the chamber/channel 55f. In this case, the sensor element 52g can be used to measure the electrical conductivity of the fluid media inside the MEM device.

The pressure sensor elements described heretofore are types of absolute gauge pressure sensors (except for capacitive pressure sensor 52u in FIG. 6E) configured to measure the pressure relative to atmospheric pressure. The pressure sensors described hereinbelow are types of differential pressure sensors (i.e., that measure the difference between two pressures each applied over one side of the membrane). FIGS. 7A and 7B are sectional views of fluidic MEM devices according to possible embodiments configured to implement differential pressure sensor elements.

FIG. 7A shows a sectional-view of a MEM device 50b, according to possible embodiments, having a body 51g and a sensor element 52e configured to measure differential fluid pressure. In this non-limiting example the MEM device 50b comprises two substantially parallel chambers/channels, 55x and 55y with a communicating bore 55p between them. The bore 55p between the chambers/channels 55x and 55y is sealed by the membrane 53 of the device 50b, so as to prevent fluid communication between them. In case a pressure difference evolves between the two chambers/channels 55x and 55y, the membrane 53 is (elastically) pressed and deformed by the higher fluid pressure in one of the chambers/channels towards the other chamber/channel having the lower pressure conditions, resulting in deflection of the transducing element 57v and/or 57u formed thereon, and responsively in a change in data/signal measured by the sensor element 52e. The transducing elements 57v and/or 57u may be a type of resistive elements as described hereinabove.

While FIG. 7A exemplifies use of two transducing elements 57v and/or 57u located on opposite sides of the membrane (transducing element 57v is associated with chamber 55x and transducing element 57u is associated with chamber 55y), it is understood that one transducing element may be used on one of the sides of the membrane 53, or embedded in it. The conductive transduction layers 57v and 57u, and their respective signal transmission lines may be encapsulated within the membrane 53 and electrically insulated from the fluid (liquid and/or gas) inside the chambers.

FIG. 7B shows a sectional view of fluidic MEM device 60 employing two absolute pressure sensors 52a and 52b (e.g., implemented using any of above-described transducing elements), and a restrictor 66. As seen, one of the absolute pressure sensors 52a is associated with a fluid flow path 65 of the device 60, while the other absolute pressure sensors 52b is associated with a slender fluid passage section 66 of the restrictor. In this way, fluid flow rate may be determined based on a pressure difference between the two absolute pressure sensors 52a and 52b. A flow channel 65 of the MEM device 60, and the restrictor 66 formed therein, can be built within the same fabrication process of the device body 61 with its membranes 66a and 66b, and its contacts 65a (e.g., using the fabrication technique illustrated in FIG. 3).

Optionally, and in some embodiments preferably, in the different embodiments described hereinabove and hereinbelow, all the transduction elements (e.g., sensing electrodes) and their respective conductive lines are electrically isolated (e.g., by PDMS or Parylene).

Figure 8I:
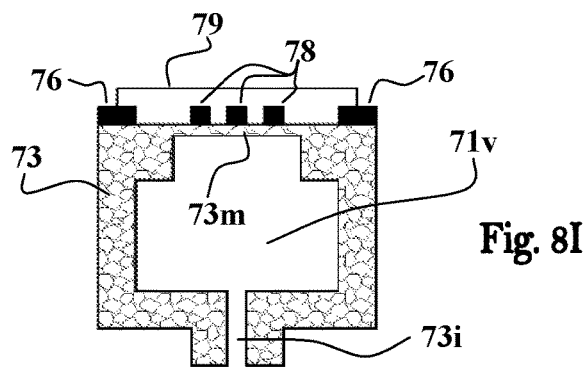

FIGS. 8A to 8I show sectional views schematically illustrating a process suitable for fabricating a fluid MEM device according to some embodiments. In FIG. 8A one or more layers comprising an initial polymeric pattern 73 and sacrificial substance pattern 71 are deposited on a substrate 77. As shown in FIG. 8B, additional layers comprising sacrificial substance 71 patterns and polymeric substance 73 patterns are successively applied one on top of the other using predefined patterns, to thereby construct a predetermined structure for the MEM device. The sacrificial substance patterns 71 and the polymeric substance pattern 73 in each layer may be (but not necessarily) complementary to each other such that each layer of the structure encompasses a complete cross-sectional area of the MEM device, without holes or voids. The structure obtained for the MEM device preferably comprises all the structures/elements of the MEM device, such as, but not limited to, the locking/latching mechanism, and interfacing means (e.g., fluid inlet/outlet).

In FIG. 8C a top thin polymeric layer 73y is applied over the multilayered structure. The thin polymeric layer 73y is used to implement membrane(s) of the MEM device. Optionally, as exemplified in FIG. 8D, a surface treatment 73t (e.g., by oxygen plasma) may be applied to the top polymeric layer 73y to improve adhesion thereto of any successively applied layer(s). In some embodiment one or more thin adhesion improving layers (e.g., made from Chrome (Cr) or Titanium (Ti)), are used to improve adhesion of the metallic electrically conducting lines and/or electrodes to the polymeric surface of the device.

Next, as shown in FIG. 8E, electrically conducting lines 78 are patterned on membrane portions (73m, in FIG. 8I) of the top polymeric layer 73y, and electric contacts (pads) 76 can be deposited on top of non-deformable (or low deflection) regions of the thin polymeric layer 73y e.g., in a single layer applied outside the membrane portions top polymeric layer 73y (the conducting lines and contact pads are also referred to herein as electrically conductive patterns). After applying the electrically conductive patterns 76/78, one or more additional polymeric patterns/layers 79 may be applied over at least a portion of the electrically conductive patterns 76/78, as seen in FIG. 8H that encapsulates the MEM device structure while enabling access to the contact pads of the MEM device.

The fabrication process may be finalized by removal of the substrate 77 and sacrificial substance patterns 71, to thereby empty the chamber 71v and release the membrane 73m, as demonstrated in FIG. 8I. In this non-limiting example the obtained MEM device structure comprises a fluid chamber/channel 71v, an elastically deformable membrane 73m with electrically conductive structure 78 patterned thereon, a fluid inlet (or outlet) 73i, and externally accessible contact pads 76.

In an alternative embodiment, exemplified in FIG. 8F, after applying the electrically conductive patterns shown in FIG. 8E, and before completing the device encapsulation shown in FIG. 8H, additional electrically conducting patterns 78a may be applied over the electrically conducting lines 78 and/or connections pads to thereby form conductive pillars for viases and/or high aspect ratio electrodes, e.g., by electroplating, or electroless plating, or electropolymerization. In yet another possible alternative embodiment, seen FIG. 8G, a polymeric foil 73f comprising the electrically conductive patterns 76/78 (e.g., conducting lines, connection pads, and/or the transducer) may be attached (e.g., by adhesion) on top of the top polymeric layer 73y.

The sacrificial substance can be made from a type of Photoresist material (e.g., SU8, AZ 4562), water-soluble polymers (e.g., polyethylene glycol (PEG), or suchlike, and the polymeric material can be made from PDMS, ABS, PVC, Polyethylene (PE), PEEK, Polycarbonate (PC), Polyetherimide (PEI), Polysulfone (PSU), Polypropylene (PP), Polyurethane (PU), or the like. The sacrificial and polymeric material patterns may be applied one on top of the other by 3D printing or lithography, for example. The electrically conducting patterns may be made, for example, from Gold (Au), Copper (Cu), Nickel (Ni), Aluminum (Al), Platinum (Pt), and they may be applied on the top polymeric layer 73y, for example, by electrodeposition, electroforming, electroplating, or electroless deposition. In some embodiment a thin adhesion layer (e.g., made of Chrome (Cr) or Titanium (Ti)) is deposited on the membrane surface to increase the adhesion of the metal lines/contacts to the surface of the device. In addition, a surface treatment may be applied to the polymer surface of the device to improve the adhesion of the metal lines and/or contacts thereto e.g., by oxygen plasma.

In some embodiments (e.g., employing some 3D printing techniques) the sacrificial layers 71 are not needed.

Figure 9A:
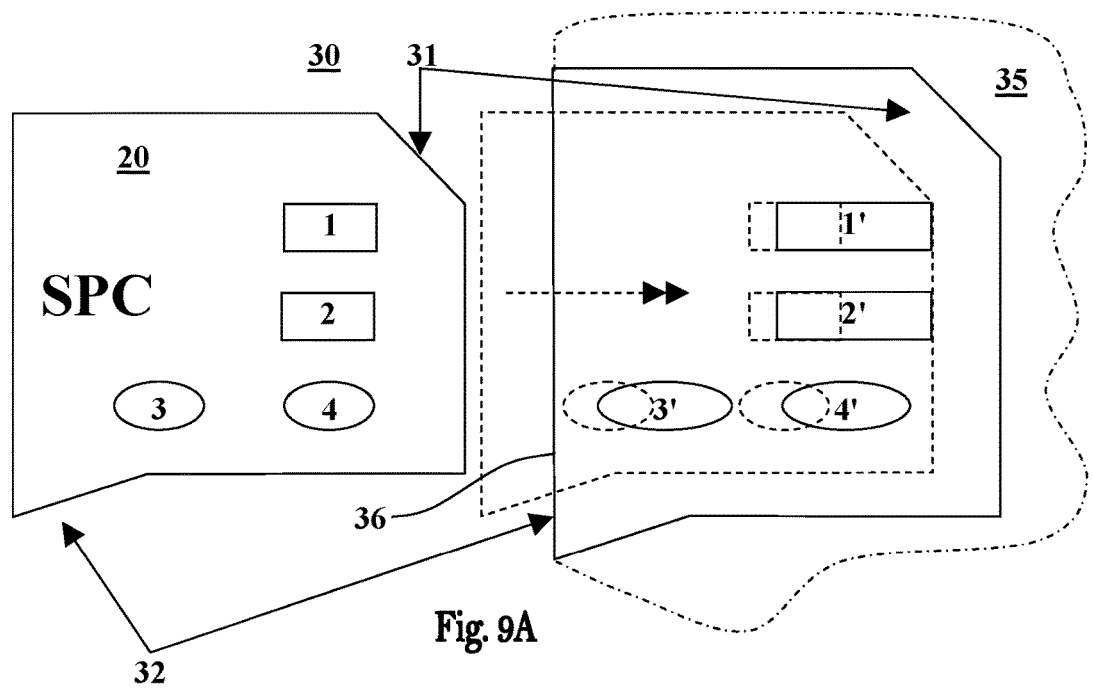
FIGS. 9A and 9B schematically illustrate mechanical and electrical interfacing of the fluidic MEM device with an external device/system according to possible embodiments.
Figure 9B:
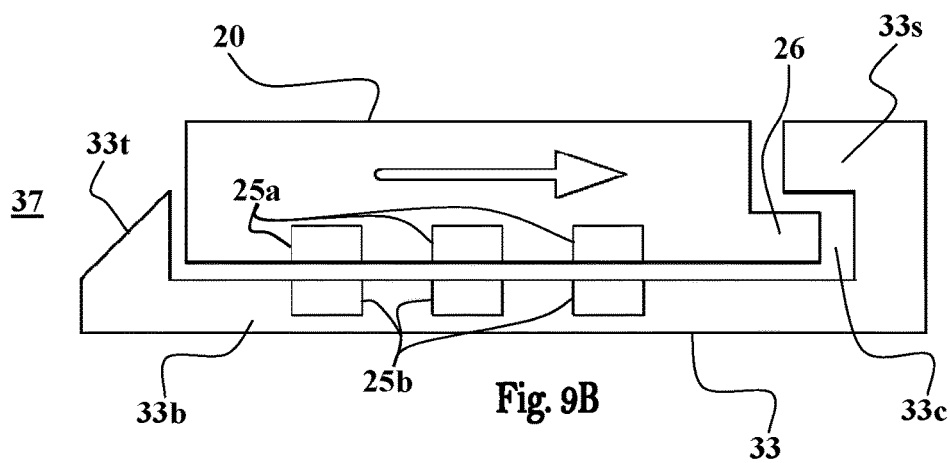

FIGS. 9A and 9B schematically illustrate mechanical and electrical interfacing of the fluidic MEM device 20 with an external device/system according to possible embodiments.

FIG. 9A schematically illustrates a quick connector mechanism 30 of the fluidic MEM device 20 according to some possible embodiments. As described hereinabove, the MEM device 20 according to the various embodiments of the present invention does not require packaging as the entire MEM device 20 is manufactured using similar processes, and within the same fabrication framework, as of the flow restrictor, flow regulators, pressure and temperature sensors. In this non-limiting example the quick connection of mechanism 30 is established by a latching slot (or cavity) 36 adapted to snugly receive the MEM device 20 by pushing it thereinto, as exemplified by dashed lines and arrows in FIG. 9A. The quick connection mechanism 30 comprises a latching/locking mechanism 32 configured and operable to secure the MEM device 20 inside the slot 36, and/or a matching mechanism 31 for assuring that the MEM device 20 fitted into the slot 36 is properly oriented.

FIG. 9B exemplifies another quick connector mechanism 37 with mechanical matching and locking designed to enable quick connection to an external device/system 33 and establishing electrical connectivity therewith. In this non limiting example a fitting socket 33c is provided in the external device 33 that allows locking the MEM device into the socket 33c while providing the needed connectivity with the external device 33. The MEM device 20 may comprise a protruding edge 26 in one end thereof designed to be received inside a cavity (at 33c) formed by a shoulder-shaped member 33s of the socket. After introducing the protruding edge 26 of the MEM device into the cavity of the socket 33c the MEM device 20 is pressed towards a base section 33b of the socket and locked thereinside as butt end (at a side opposite to the protruding edge 26) thereof is pressed against a retaining member 33t (at a side opposite to the cavity) of the socket 33c. The MEM device 20 thus becomes locked inside the socket 33c while electrical connection is established between contacting pads 25a of the MEM device 20 and corresponding contact pads 25b provided in the base section 33b of the socket. The quick connection mechanism 37 may comprise means providing sealable fluid connection between the MEM device 20 and the external device 33.

As exemplified in FIG. 1D, the external devices and/or systems 35 can comprise one or more reservoirs (11), or fluid supply lines coming from them, connectable to the inlet (12i) of the MEM device 20, one or more delivery/dispensing units (14), or liquid delivery lines coming from them, connectable to the outlet (12u) of the MEM device 20, and external (or integrated) control units (13) electrically coupled to the MEM device 20. The electrical connection to the external control unit 13 includes matching electrical connections for reading the temperature, conductivity and/or pressure sensors (e.g., 1-1' and 2-2'), and connectors for actuating the flow regulators (12v) either mechanically, electromagnetically or electrostatically (e.g., 3-3' and 4-4').

The MEM device 20 can include in some embodiments matching, and/or locking, and/or latching mechanisms (e.g., Luer locks, not shown in FIGS. 9A and 9B) configured and operable to establish fluid sealable communication between the MEM device 20 and external devices and/or systems 35.

Figure 10A:
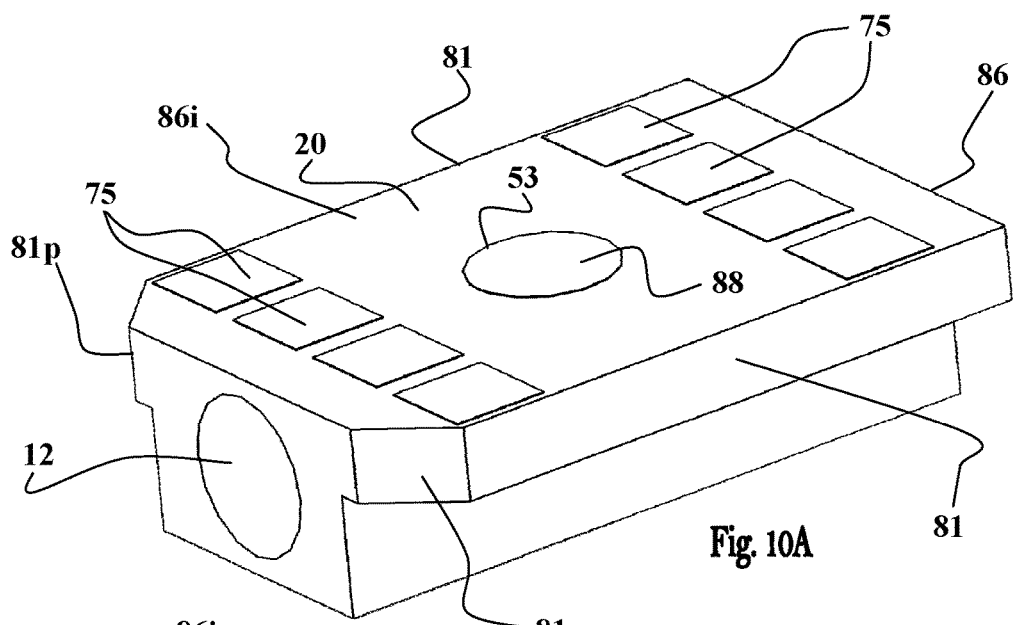
Figure 10B:
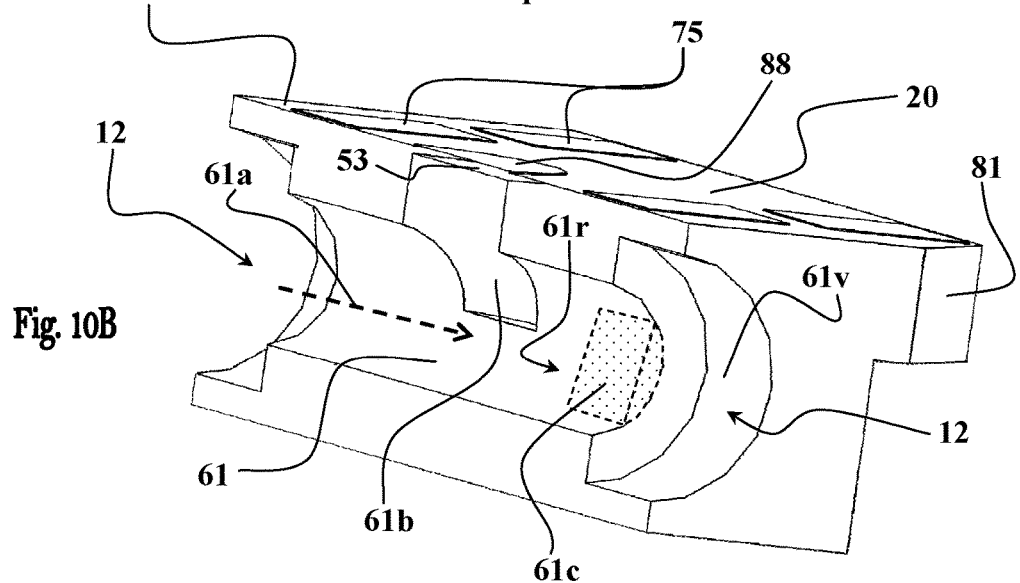

FIGS. 10A and 10B show a possible configuration of the fluidic MEM device 20 according to possible embodiments configured to measure pressure of fluid media. In this non-limiting example the MEM device 20 is made of a substantially rectangular body 86 having a fluid port 12 at each side thereof, for passage of fluid media through the channel 61 passing along the body of the MEM device 20. An interfacing face 86i of the MEM device 20 comprises an array of contact pads 75 for establishing electrical connection between the MEM device 20 and external devices/systems, a deformable membrane 53, and transducing element(s) 88 formed on (or in) the membrane 53 and electrically coupled to the contact pads 75 for measuring fluid pressure inside the channel 61. The interfacing side 86i of the MEM device 20 also comprises two grubbing ears 81 laterally protruding in opposite sideway directions of the device. The grubbing ears 81 may comprise facets 81p formed at one end thereof for matching the MEM device 20 to respective mechanical connection means of an external device/system, as will be exemplified below.

With reference to FIG. 10B, a pass-through bore 61b connecting between the fluid channel 61 and the interfacing face 86i of the device is sealed by the membrane 53 covering the opening of the bore 61b, such that fluid media introduce into the channel 61 can interact with the membrane 53 through the bore 61b. The contact pads 75 provide electrical connection to the transducing element(s) 88 formed on the membrane 53 for measuring the fluid pressure inside the channel 61. The fluid ports 12 may be configured to implement quick connectors (e.g., Luer locks) to allow sealable and quick connection of the MEM device 20 to external device/system.

In some possible embodiments the fluid channel 61 may comprise a restrictor 61r implemented by a constriction 61c formed in the fluid channel 61 usable for implementing a differential flow sensor using a single gauge pressure sensor 88. For example, if the fluid media is introduced into the MEM device via the non-constricted side of the device, as demonstrated by dashed arrowed line 61a, and there are environmental pressure conditions at the outlet 61v of the device, then the same pressure conditions occur across the restrictor 61r and within the non-constricted portion of the fluid channel 61. As there are same pressure conditions on the two sides of the membrane 53 a differential fluid pressure measurement is obtained by the sensor element 88.

Figure 10C:
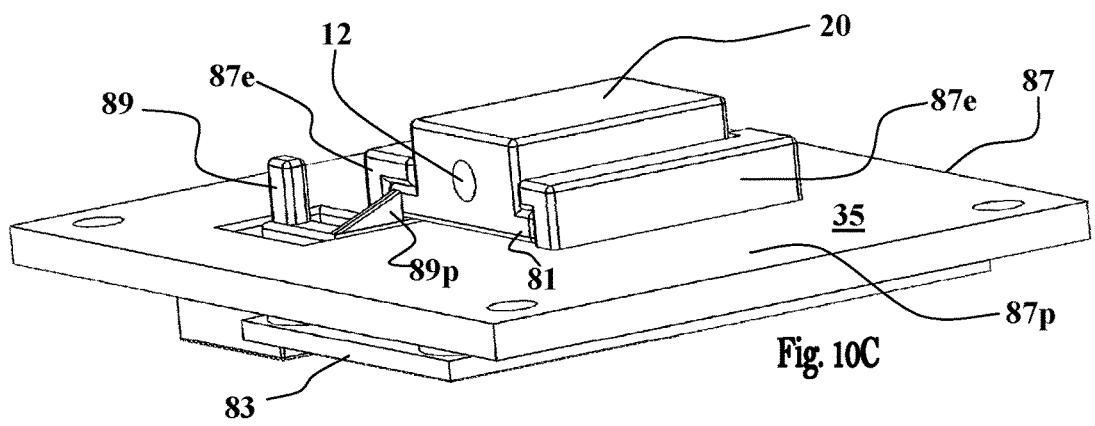

FIGS. 10C to 10F exemplify possible mechanisms for connecting the MEM device to external devices/systems. In FIG. 10C the MEM device 20 is shown in operational settings attached to an external device/system 35. The MEM device 20 is attached to a docking assembly 87 having a support plate 87p with two fastening structures 87e formed on a top side thereof and configured to receive and hold the grubbing ears 81 of the MEM device 20, and a PCB 83 attached to a bottom side of the support plate 87p and configured to establish electrically connection with the contact pads 75 of the MEM device 20 upon attachment thereof to the external device 35.

Figure 10D:
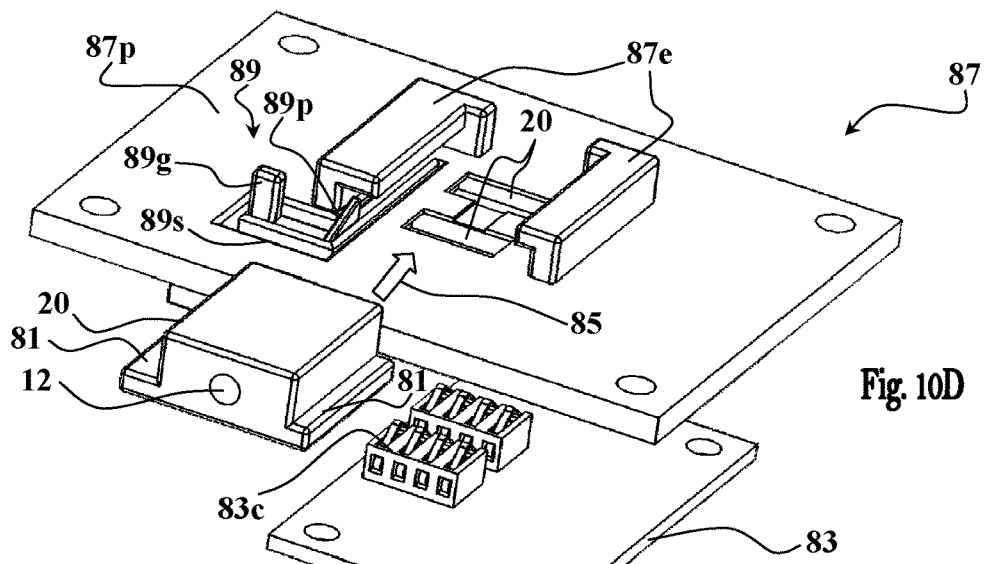

FIG. 10D shows an exploded perspective view of the docking assembly 87. A slot 89s formed in the support plate 87p accommodates a latching mechanism 89 configured to lock the MEM device 20 in its operational setting between the fastening structures 87e. The latching mechanism 89 comprises a depressible tongue 89p configured to be reversibly depressed into the slot 89s while the MEM device 20 is slid along the surface of the support plate 87p towards the fastening structures 879e, as shown by arrow 85. As seen in FIG. 10C, upon fully inserting the MEM device 20 between the fastening structures 87e the depressible tongue 89p emerge upwardly from the slot 89s and locks the MEM device immobilized in its operational state therein. A push button 89g provided in the latching mechanism 89 can be used to move the depressible tongue 89p into the slot 89s for releasing the MEM device 20 from the docking assembly 87.

Also seen in FIG. 10D, an array of upwardly projecting electrical contacts 83c provided on the PCB 83 configured for placement in pass-through bores 20 formed in the support plate 87p, to thereby establish electrical connection with the contact pads 75 of the MEM device 20 upon placement in operational state in the docking assembly.

Figure 10E:
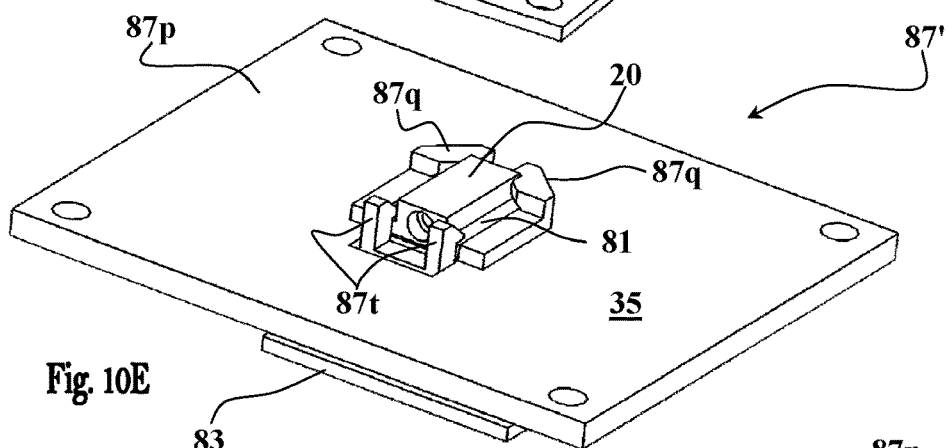
Figure 10F:
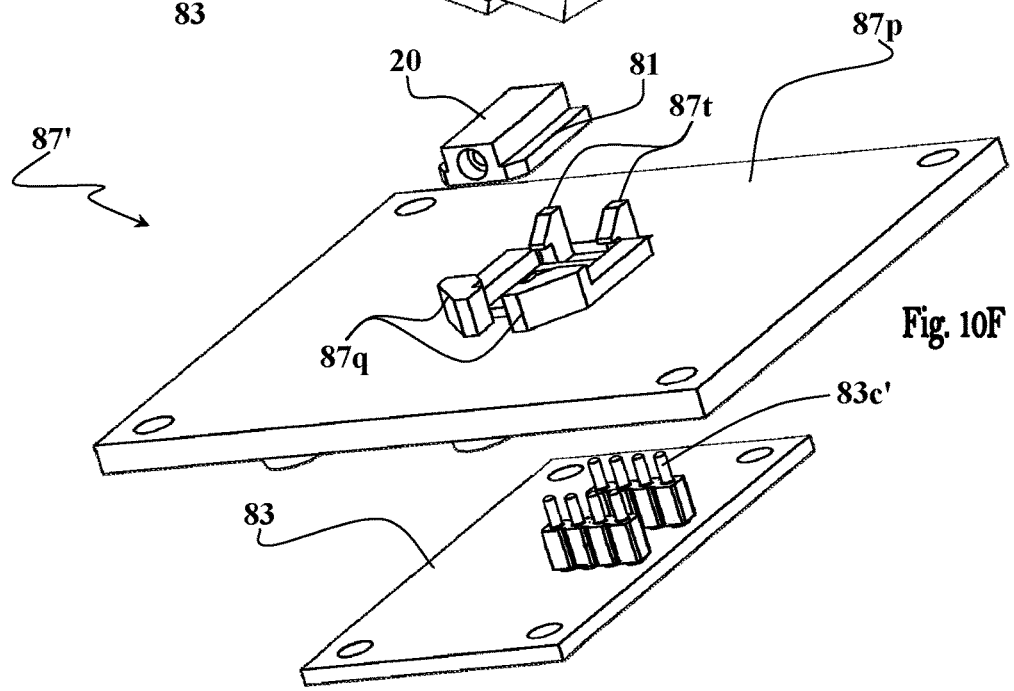

Referring now to FIGS. 10E and 10F, exemplifying another docking assembly 87' according to a possible embodiment wherein two deflectable clamps 87t are used for holding the MEM device 20 immobilized in an operational state on the support plate 87p between two lateral holders 87q. In this embodiment the lateral holders 87q are configured to retain the corners of the grubbing ears 81 of the MEM device 20 at its leading end (with respect to direction of insertion therebetween) in matching cavities, and thereafter the MEM device is pressed towards the support plate 87p and clamped by the clamps 87t as it is fitted between the holders 87q and the clamps 87t are "snapped"/lock over the trailing ends of the grubbing ears 81. In this state the contact pads 75 of the MEM device 20 establish electrical connection with the contactors array 83c' of the PCB 83. In some embodiments the contactors array 83c' are implemented by a type of spring loaded connectors, configured to allow the connectors to move up and down to thereby facilitate in keeping MEM device in place secured to the support plate 87p. The MEM device 20 can be released from the docking assembly by pulling the clamps 87t and lifting the MEM device from the holders 87q.

In possible embodiments the PCB 83 may include additional contact and circuitries, as may be needed by the external device/system 35 (e.g., control units, Wheatstone bridge elements, power source, and suchlike).

Figure 11A:
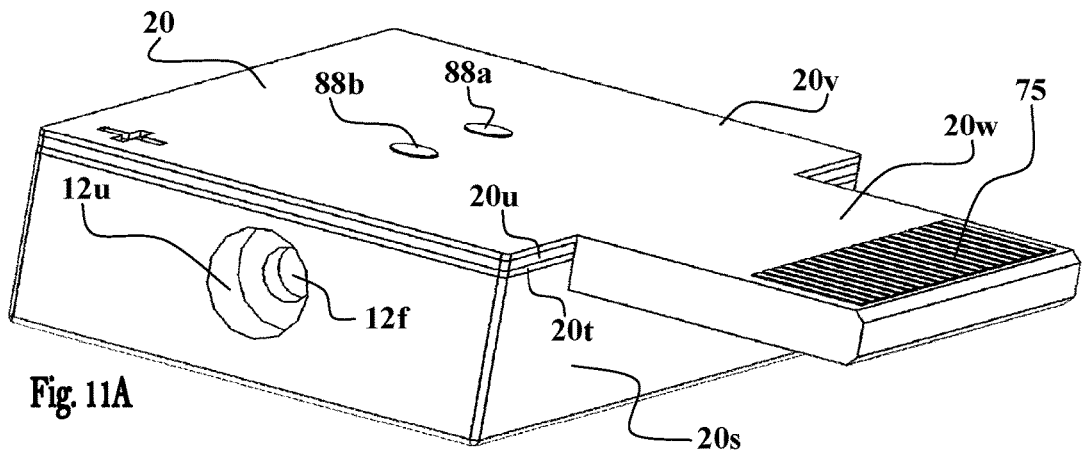
Figure 11B:
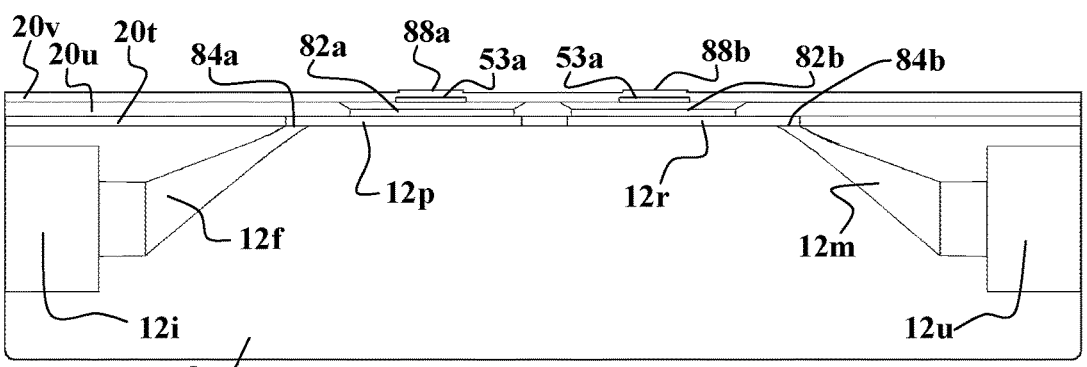
Figure 11C:
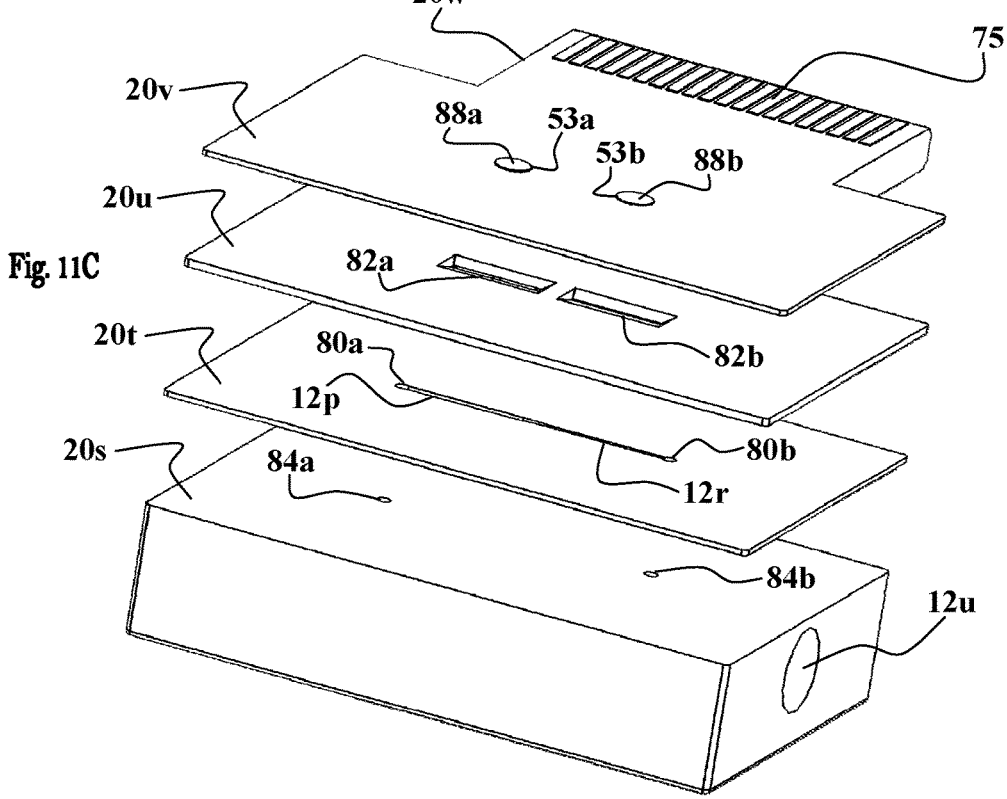

FIGS. 11A to 11C show a fluidic MEM device 20 structure usable according to possible embodiments for measurement of fluid pressure and/or flow rate. The MEM device 20 in this non-limiting example is a multilayered structure comprising a base structure 20s a flow path layer 20t, a fluid chambers layer 20u (also referred to herein as intermediate layer), and a membrane layer 20v (also referred to herein as encapsulating layer). The MEM device further includes a laterally projecting lip 20w comprising a plurality of contact pads configured to provide electrical connectivity to sensing and/or actuating elements of the MEM device 20, and to circuitries and/or other elements (e.g., control module) embedded in the MEM device 20.

With reference to FIG. 11B showing a sectional view of the MEM device 20, the base portion 20s of the device comprises internal flow structures configured to receive fluid media via a fluid inlet 12i thereof, communicate the received fluid media to elements residing in the other layers, receive back the fluid media from the other layers and discharge it via a fluid outlet 12u thereof. The fluid inlet 12i and outlet 12u of the MEM device 20 may be configured as sealable quick connection structures (e.g., Luer lock) to permit quick connection to fluid supplying means (e.g., drug reservoir) and to a fluid delivery system (e.g., drug delivery/dispensing device).

Referring now to FIGS. 11B and 11C, the base structure 20s comprises a receive channel 12f in fluid communication with the inlet 12i and gradually tapering therefrom towards a small opening 84a at the upper surface of the base structure 20s, and a transfer channel 12m in fluid communication with the outlet 12u and gradually tapering therefrom towards another small opening 84b at the upper surface of the base structure 20s. The flow path layer 20t, stacked on top of the base structure 20s, comprises two corresponding holes 80a and 80b (seen in FIG. 11C) configured to be aligned and overlap the small openings 84a and 84b in the upper surface of the base structure 20s. A slot formed in the flow path layer 20t connects between the two holes 80a and 80b, thereby forming a fluid flow path of the MEM device 20. The fluid flow path may comprise two sections having different cross-sectional areas, a first section serving as the fluid channel 12p communicates with the first hole 80a, and a second section having a smaller cross-sectional area and serving as the restrictor 12r communicates between the fluid channel 12p and the second hole 80b. A tapering constriction may be formed between the fluid channel 12p and the restrictor 12r.

The fluid chambers layer 20u stacked on top of the flow path layer 20t comprises two slots 82a and 82b having tapered profiles configured to form fluid chambers in the layer. Each slot has a slender portion passing along the bottom side of the fluid chambers layer 20u, and a wide (enlarged) portion passing along the upper side of the layer. The first slot 82a is aligned with a section (or entire length) of the fluid channel 12p formed in the flow path layer 20t such that its slender portion communicates with the fluid channel 12p, and the second slot 82b is aligned with a section (or entire length) of the restrictor 12r such that its slender portion communicates with the restrictor 12r.

The flow structures of the MEM device 20 are sealed by the uppermost membrane layer 20v configured with two elastically deflectable membranes 53a and 53b, each having a respective transducing sensing element, 88a and 88b, patterned thereon. The location of the membranes 53a and 53b in the membrane layer 20v places each membrane over a respective fluid chamber implemented by the slots 82a and 82b such that the fluid pressures applied by the fluid media introduced into the chambers can be sensed by the respective transducing sensing elements 88a and 88b, as the fluid media in the chambers interacts with the respective membranes, and measured via the contact pads 75 of the MEM device 20.

In this way, fluid media introduced into the MEM device 20 through its inlet 12i is transferred via receive channel 12f into the fluid channel 12p, its restrictor and the fluid chambers formed by the slots 82a and 82b, and therefrom discharged via the transfer channel 12m and outlet 12u. The measurement data/signals obtained from the transducing sensing element 88a is thus indicative of the pressure conditions inside the slot 82a and the fluid channel 12p coupled to it, and the measurement data/signals obtained from the transducing sensing element 88b is indicative of the pressure conditions inside the slot 82b and the restrictor 12r coupled to it. The control unit (13) can use the measurement data to determine the fluid flow rate through the MEM device 20.

The MEM device 20 illustrated in FIGS. 11A to 11C may be manufactured using the same materials and techniques described hereinabove. In some possible embodiments the different layers of the MEM device 20 may be separately prepared in different manufacture procedures, and thereafter sealably glued or welded to each other to form the desired MEM device structure illustrated in FIGS. 11A to 11C. The cross-sectional area of the fluid flow path 12p formed in the layer 20t may be in some embodiment about 0.0001 to 25 mm², and the cross-sectional area of its restrictor 12r may be about 0.0001 to 24.9 mm². Volume of the each fluid chamber formed by the tapered slots 82a and 82b in layer 20u may be in some embodiments about 0.001 to 125 mm³.

In some embodiments a layered structure is constructed by sealably attaching the fluid chambers layer 20u to the flow path layer 20t such that fluid communication is established between the slot 82a and the fluid flow path 12p, and between the slot 82b and the restrictor 12r, and attaching the membrane layer 20v to the fluid chambers layer 20u such that the membrane 53a is placed over the slot 82a, and the membrane 53b is placed over the slot 82b. The layered assembly is then attached to the base structure 20s such that fluid communication is established between the opening 84a and the fluid flow path 12p, and between the opening 84b and the restrictor 12r.

In some possible embodiments the MEM device is constructed without the fluid chambers layer 20u. In this case a layered structure may be assembled by sealably attaching the membrane layer 20v directly to the flow path layer 20t such that membrane 53a is position directly over the fluid flow path, and the membrane 53b is positioned directly over the restrictor 12r.

Figure 11D:
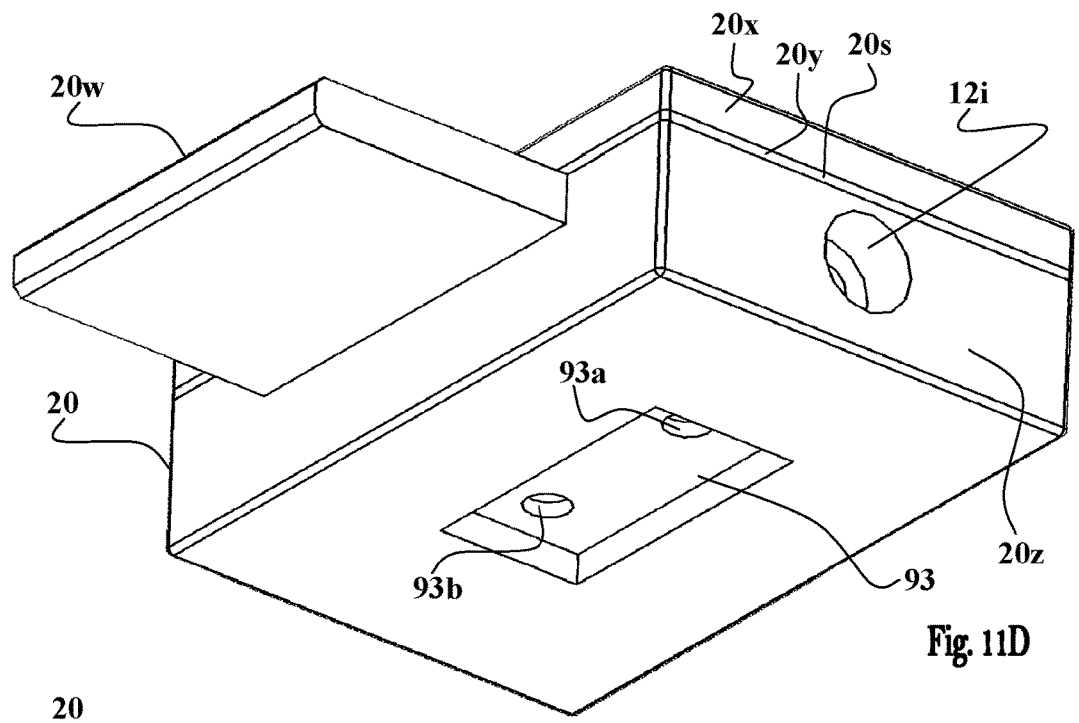
Figure 11E:
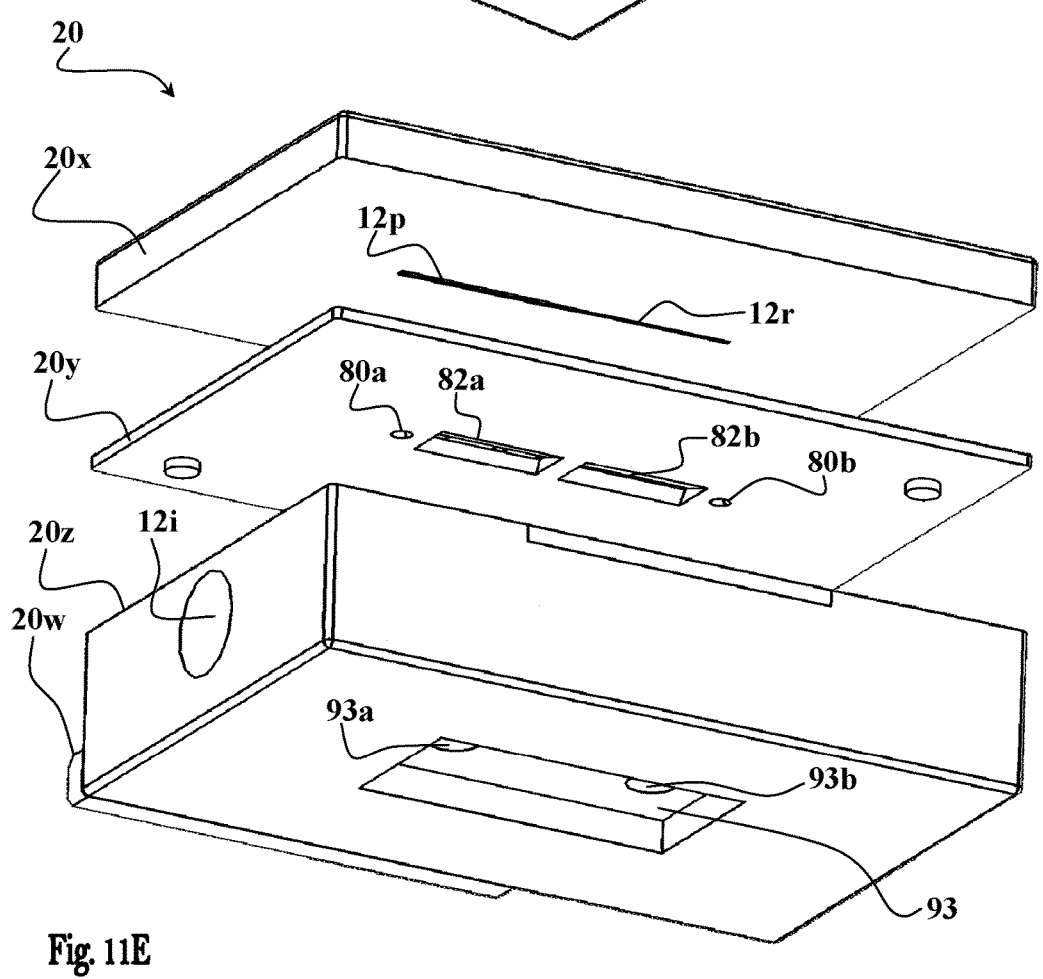
Figure 11F:
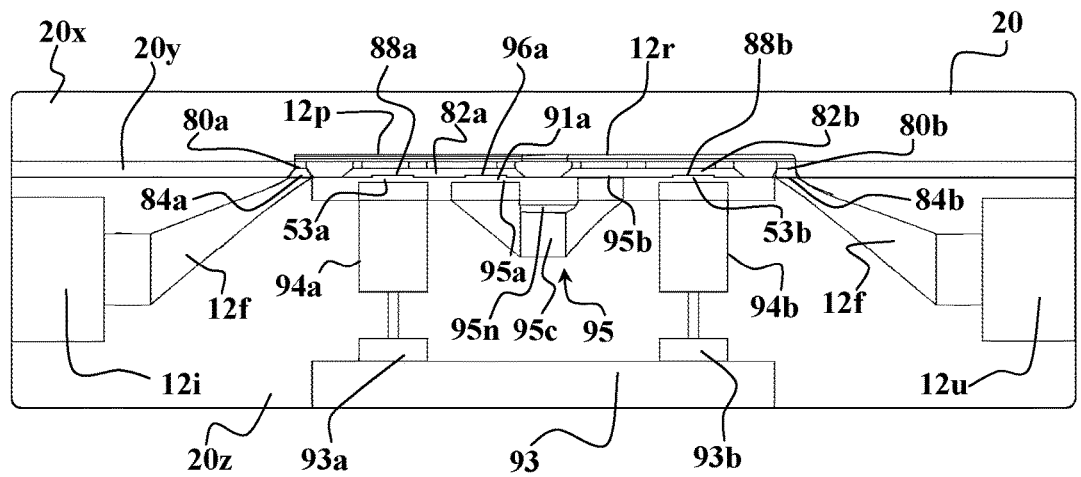

FIGS. 11D to 11F show another configuration of a fluidic MEM device 20 structure usable according to possible embodiments for measurement of fluid pressure and/or flow rate. In this embodiment the MEM device 20 is also a multilayered structure comprising a base structure 20z, an intermediate fluid chambers layer 20y (also referred to herein as transition layer), and a top fluid flow path layer 20x (also referred to herein as encapsulating layer). The MEM device further includes a laterally projecting lip 20w having a plurality of contact pads (75) configured to provide electrical connectivity to sensing and/or actuating elements of the MEM device 20, and to circuitries and/or other elements (e.g., control module) embedded in the MEM device 20. A cavity 93 provided in the bottom side of the base structure 20z includes two openings 93a and 93b communicating with respective internal sensor compartments (94a and 94b, in FIG. 11F) of the device.

As seen in FIG. 11E showing an exploded view of the MEM device, a longitudinal channel formed at the bottom side of the fluid flow path layer 20x implements the fluid flow path 12p and its restrictor 12r. In this case the channel has a certain predetermined depth into the flow path layer 20x to allow sealing it by the intermediate fluid chambers layer 20y and the base structure. The intermediate layer 20y comprises two pass-through bores 80a and 80b for communicating fluid media between the flow structures of the base structure 20z and of the fluid flow path layer 20x.

Referring now to FIG. 11F, in the intermediate layer 20y, a first pass-through bore 80a aligned with, and overlapping the, upper opening 84a of the receive channel 12f in the base structure 20z is used to communicate fluid media received via the inlet 12i to the fluid flow path 12p formed in the flow path layer 20x, and a second pass-through bore 80b aligned with, and overlapping the, upper opening 84b of the transfer channel 12f in the base structure 20z is used to communicate fluid media from the restrictor 12r formed in the flow path layer 20x to the outlet 12u of the device.

The intermediate layer 20y comprises two slots 82a and 82b having tapered profiles configured to form fluid chambers in the layer. Each slot has a slender portion passing along the upper side of the intermediate layer 20y, and a wide (enlarged) portion passing along the bottom side of the layer. The first slot 82a is aligned with a section (or entire length) of the fluid channel 12p formed in the flow path layer 20x such that its slender portion communicates with the fluid channel 12p, and the second slot 82b is aligned with a section (or entire length) of the restrictor 12r such that its slender portion communicates with the restrictor 12r. This structure thus enables communicating fluid passing through the fluid channel 12p and its restrictor 12r into the respective chambers formed by the slots 82a and 82b in the intermediate layer 20y.

The base structure 20z comprises sensor compartments incorporating sensing elements of the device. A first compartment 94a provided in the base structure 20z is connected to the opening 93a in the bottom cavity 93 and covered by a membrane layer 53a having a transducing element 88a formed thereon, and a second compartment 94b provided in the base structure 20z is connected to the opening 93b in the bottom cavity 93 and covered by a membrane layer 53b having a transducing element 88b formed thereon. The membranes 53a and 53b are preferably implemented by thin top layer of the base structure 20z. As seen in FIG. 11F, the membranes 53a and 53b are in contact with the chambers formed in the intermediate layers 20y by the slots 82a and 82b, respectively. Thus, the measurement data/signals obtained from transducing element 88a is indicative of pressure conditions in the first chamber formed in the intermediate layer 20y by the slot 82a, and in the fluid flow path 12p fluidly coupled to it, and the measurement data/signals obtained from transducing element 88b is indicative of pressure conditions in the second chamber formed in the intermediate layer 20y by the slot 82b, and in the restrictor 12r fluidly coupled to it.

In this configuration, if the opening 93a in the bottom cavity 93 is sealed with specific pressure conditions inside the sensor compartment 94a, then the pressure sensor implemented by the transducing element 88a is a sealed pressure sensor (i.e., similar to a gauge pressure sensor except that it measures pressure relative to some fixed pressure rather than the ambient atmospheric pressure). Similarly, if the opening 93b in the bottom cavity 93 is sealed with specific pressure conditions inside the sensor compartment 94b, then the pressure sensor implemented by the transducing element 88b is a sealed pressure sensor. In case the openings 93a and 93b are open such that there are atmospheric pressure conditions inside the sensor compartments 94a and 94b, the sensor elements implemented by the transducing elements 88a and 88b are regular gauge sensors.

The MEM device 20 shown in FIGS. 11D to 11F may further comprise a differential pressure sensor 95. The differential pressure sensor 95 may be implemented using a "U"-shaped differential pressure sensor cavity 95c residing in the base structure 20z, where top opening 95a of one of its arms is sealably closed by thin membrane 91a formed by a top layer of the base structure 20z, while the top opening 95b of the other arm is open to communicate fluid media with restrictor 12r through the second chamber formed in the intermediate layer 20y by the slot 82b. In this way, the upper side of the membrane 91a is in contact with the first chamber formed in the intermediate layer 20y by the slot 82a, and thus the pressure conditions in the fluid flow path 12p are applied on it. On the other hand, the pressure conditions inside the cavity 95c, and that are applied on the bottom part of the membrane 91a, are the same as in the restrictor 12r. Thus, deformations of the membrane 91a corresponds to the pressure difference between the fluid flow path 12p and its restrictor 12r, and accordingly, the measurement data/signals obtained from the transducing element 96a of membrane 91a is indicative of the pressure difference along the fluid channel.

Accordingly, in operation the "U-Shape" channel 95c is filled with the fluid media. If liquid media is used with the MEM device, then air contained within the cavity 95c can be removed through the channel 95n communicating between the two arms of the "U"-shaped cavity 95c. Alternatively, in some embodiments, the cavity 95c is filled with an uncompressible fluid/gel so that the pressure can be completely transmitted to the bottom side of the membrane 95a (as 95b remain opened to the restrictor pressure) e.g., the fluid or gel within the cavity 95c may be sealed by the same coating process used to apply the membrane of the sensing element.

In possible embodiments the opening 95b of the "U"-shaped cavity may be sealed by a thin membrane (not shown), while the opening 95a of the other arm is maintained open (not shown) to communicate fluid media with the fluid flow path 12p through the first chamber formed in the intermediate layer 20y by the slot 82a. Accordingly, in such embodiments the pressure applied over the upper side of the membrane will be the pressure in the restrictor 12r, while the pressure applied over the bottom side of the membrane will be pressure in the fluid flow path 12p.

The use of such differential sensor allows to significantly reduce the precision needed for the flow control (e.g., to about 1% with the differential pressure sensor while using absolute pressure sensors requires precision of about 0.05%). Of course, as the absolute pressure that needs to be measured is increased the accuracy requirements of the absolute pressure sensors are also increased.

Figure 11G:
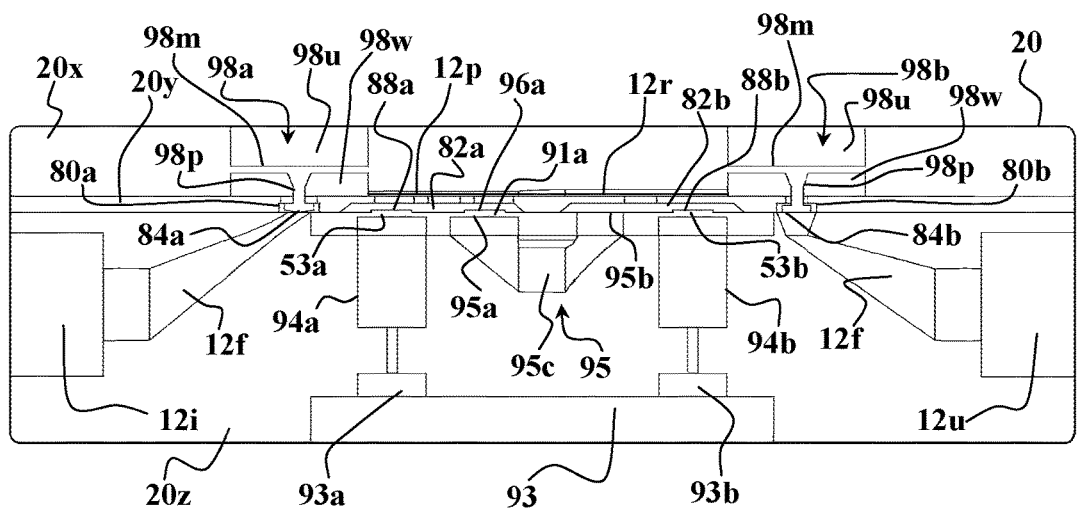

FIG. 11G shows a sectional view of a MEM device 20 structure according to possible embodiments having flow regulators 98a and 98b. The MEM device shown in FIG. 11G is also a multilayered structure comprising a base structure 20z, an intermediate fluid chambers layer 20y (also referred to herein as transition layer), and a top fluid flow path layer 20x (also referred to herein as encapsulating layer). The structure of the layers may be substantially similar to the layers of the MEM device shown in FIGS. 11D to 11F, but not necessarily. The flow regulators 98a and 98b may each be implemented using a thin membrane 98m sealably separating between overlapping upper cavity 98u and lower cavity 98w, formed in the fluid flow path layer 20x, where the lower cavities 98w of each flow regulator are in fluid communication with their respective pass-through bore 80a and 80b. A piston 98p attached to the bottom side of the membranes 98m is usable to restrict (or completely occlude/seal) the passage through the opening 84a/b to the fluid channel 12p and restrictor 12r by actuating mechanical pressure (e.g., using electromagnetic or mechanical actuator) over the upper side of the membrane 98m.

More particularly, in this embodiment fluid media from the receive channel 12f is delivered into the fluid flow path 12p through the lower cavity 98w. Thus, as the piston 98p of the flow regulator 98a is pushed by the respective membrane 98m downwardly towards the top opening 84a of the receive channel 12f the fluid flow passage to the lower cavity 98w is restricted, or becomes fully blocked once the top opening 84a is sealed by the piston 98p. Similarly, as the piston 98p of the flow regulator 98b is pushed by the respective membrane 98m upwardly towards the opening 80b of the transfer channel 12f the fluid flow passage to the lower cavity 98w is restricted, or becomes fully blocked once the top opening 84b is sealed by the piston 98p.

In a normally-open configuration, once the actuating pressure over the membrane is removed, the original state of the membranes 98m is restored, and the pistons 98p are retracted upwardly, thereby releasing the fluid flow restriction over the fluid passage and allowing passage of fluid media to/from the fluid channel of the device. Optionally, and in some embodiments preferably, a normally closed configuration is used, as exemplified in FIG. 11G, wherein actuating means (not shown) are used to push downwardly the membranes 98m and their respective pistons 98p to permit fluid communication to the lower cavities 98w of the flow regulators. Such normally closed configurations of the flow regulators prevent reflow from the output channel to the input channel in case the input pressure falls below the output pressure.

The MEM device of FIG. 11G may be manufactured in a two step process comprising (i) polymer fabrication, and (ii) conductive/sensing layers deposition (e.g., using integrated circuits (IC) technology). Considering the dimension of a MEM device (e.g., about 1 cm$^3$), in mass production of the MEM devices the manufacture may be carried out as follows (i) first, the base structure 20z (FIG. 11E), fluid flow path layer 20x and the intermediate fluid chambers layer 20y are manufactured with their flow structures, (ii) the conducive layers (lines, contact pads 75 and transducing elements) are deposited on the base structure 20z, and (iii) the flow path layer 20x is sealably adhered/welded on top of the fluid chambers layer 20y (in some embodiments the flow path layer 20x and the fluid chamber layer 20y are manufactured as a single unit), which are then sealably adhered/welded on top of the base structure 20z. As seen in FIG. 11E the lip 20w (with contact pads 75) laterally projects from the base structure 20z to facilitate connection to the conducting elements (lines, transducing elements) on the base structure 20z.

In some embodiment a layered structure is assembled by sealably attaching the flow path layer 20x to the fluid chambers layer 20y such that fluid communication is established between the fluid flow path in the flow path layer 20x and the hole 80a and slot 82a in the fluid chambers layer 20y, and between the restrictor 12r in the flow path layer and the hole 80a and slot 82a in the fluid chambers layer 20y. The layered structure is then attached to the base structure 20z such that the slots in the fluid chambers layer 20y are placed over their respective membranes in the base structure 20z (slot 82a is placed over membrane 53a/91a and slot 82b is placed over membrane 53b).

Figure 11H:
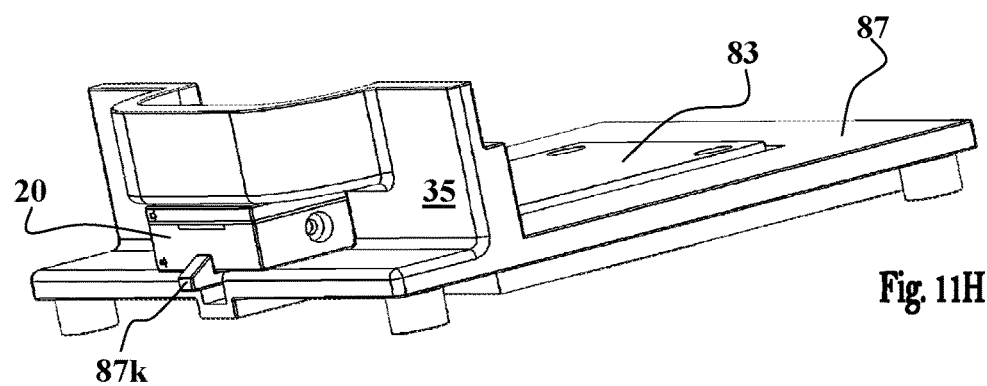
Figure 11I:
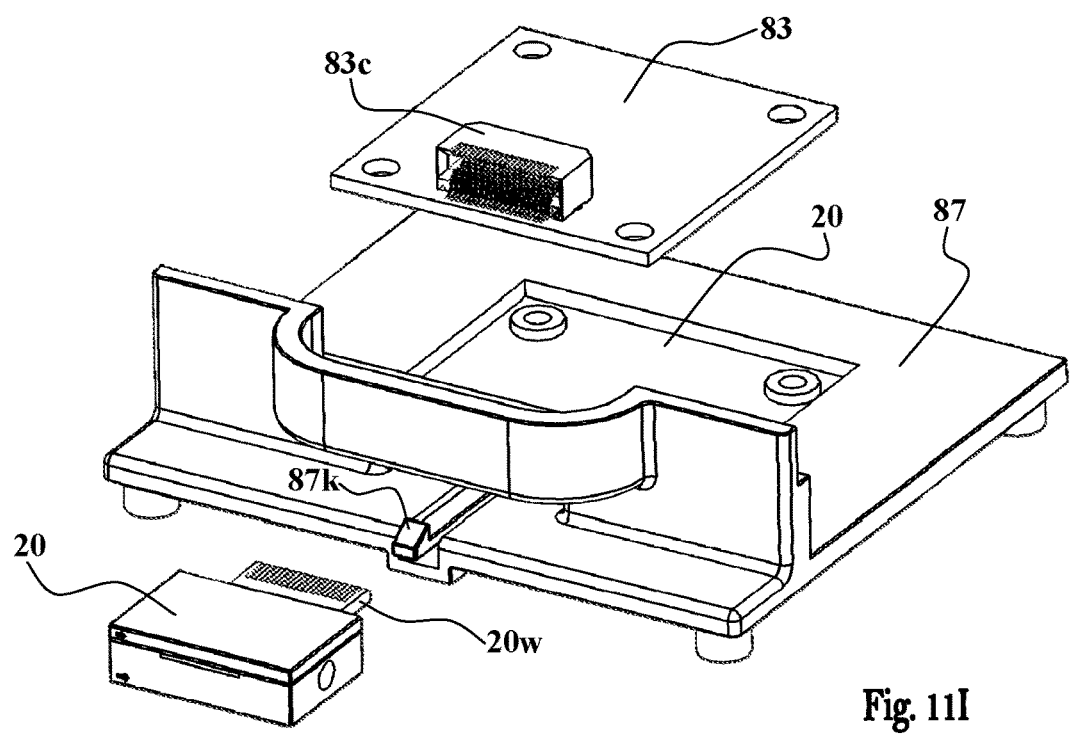

FIGS. 11H and 11I exemplify a possible mechanism for quick connection of the MEM device 20 to external systems 35. In this non-limiting example the docking assembly 87 is designed to receive the MEM device 20 by sliding its projecting lip 20w inside a connector assembly 83c mounted on the PCB 83. As the lip inserted into the connector 83c it is locked and immobilized by a deflectable clamp 87k, and electrical connectivity is established between the contact pads 75 and the PCB 83, allowing the external device to read measurement signals/data from the MEM device and/or provide actuating signals for changing the state of flow regulating elements of the device. This locking system can better hide the contacts of the external electronic when the MEM device is not inserted (e.g., can easily protect the electrical contact of the external electronic from sprinkles of water).

Figure 12A:
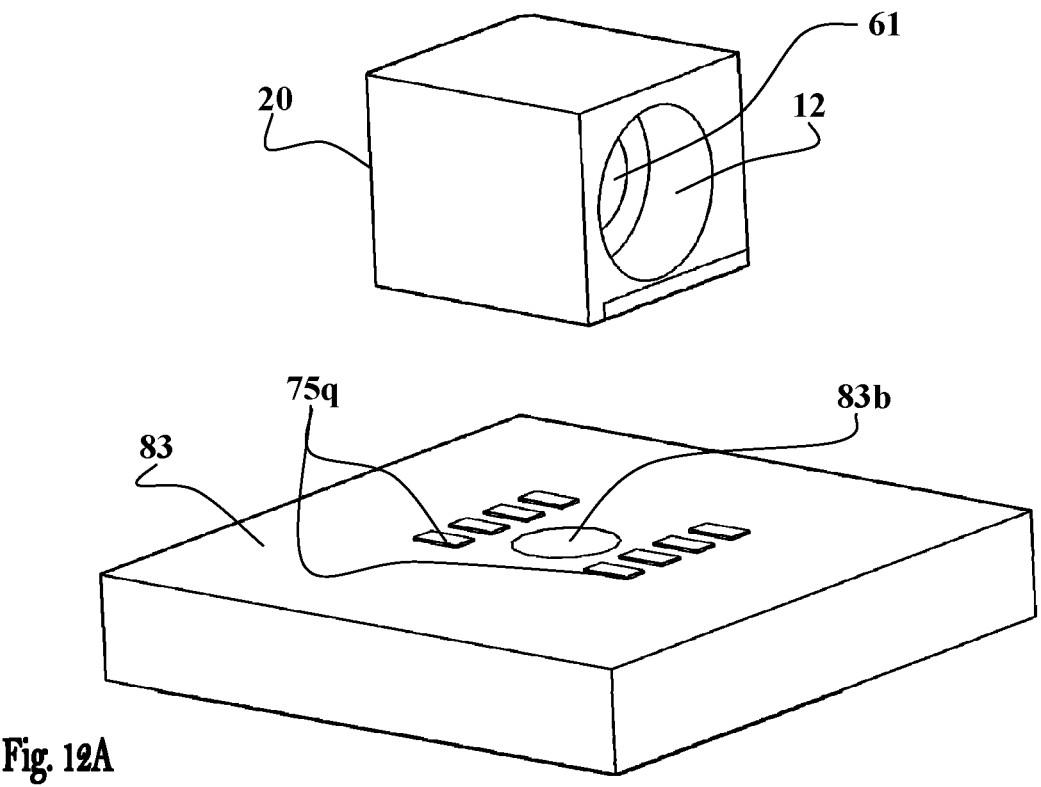
Figure 12B:
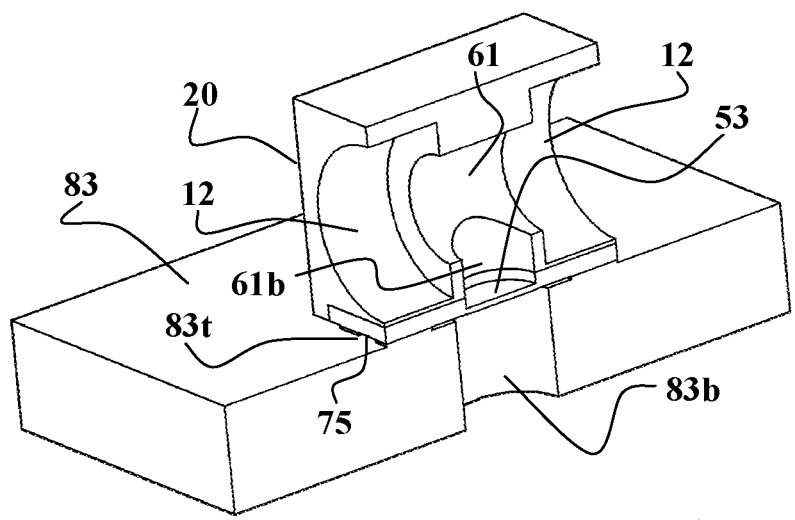

FIG. 12A is an exploded view exemplifying a possible embodiment wherein the MEM device 20 is attached to a printed circuit board 83 having contact pads 75q and a cavity 83b. With reference to FIG. 12B, showing a sectional view of the fluidic MEM device 20 attached to the PCB 83. In this non-limiting example the side surface of the MEM device comprising the membrane 53 with a sensing element (not shown) and the contact pads 75 is attached to the surface of the PCB 83. In order to permit deflection of membrane 53 the MEM device 20 is attached to the PCB 83 (e.g., by contact bonding 83t) by placing the deformable membrane 53 over the cavity 83b.

In some embodiments the MEM device is bonded to a PCB, as exemplified in FIG. 12 described above e.g., as a standard SMD component. In other possible embodiments SMD components are bonded to the MEM device, as exemplified in FIGS. 13A to 13C. In particular, after the metallization process is completed, a polymeric wafer comprising an array of dies of MEM devices 20 (shown in FIG. 14) can be seen as PCB where electronic components/circuitries can be attached (e.g., passive components, SMD chips, ASIC, battery, integrated antenna, etc.).

Figure 13A:
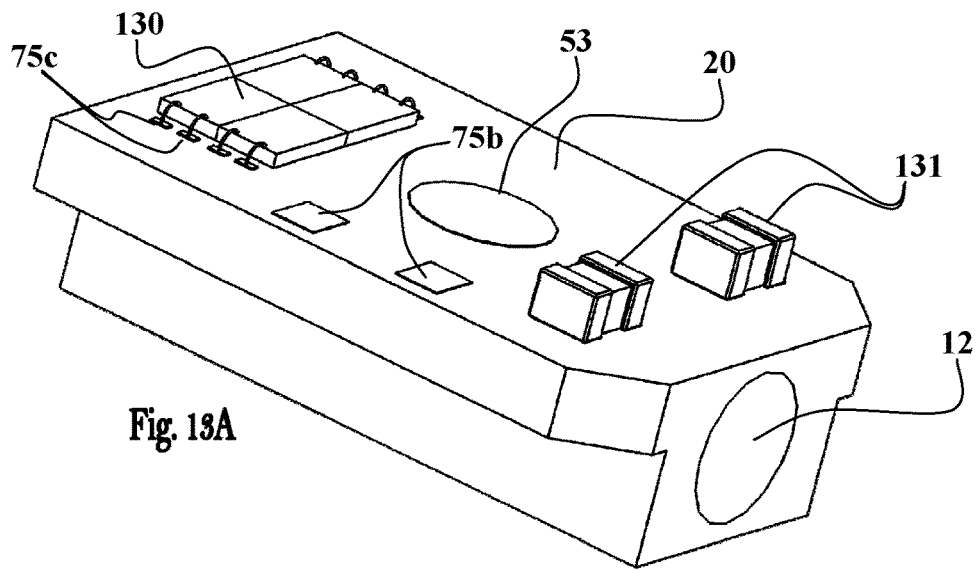
FIGS. 13A to 13C show perspective, exploded and sectional, views, respectively, of a MEM device having electrical elements and/or circuitries attached to its body according to some possible embodiments.
Figure 13B:
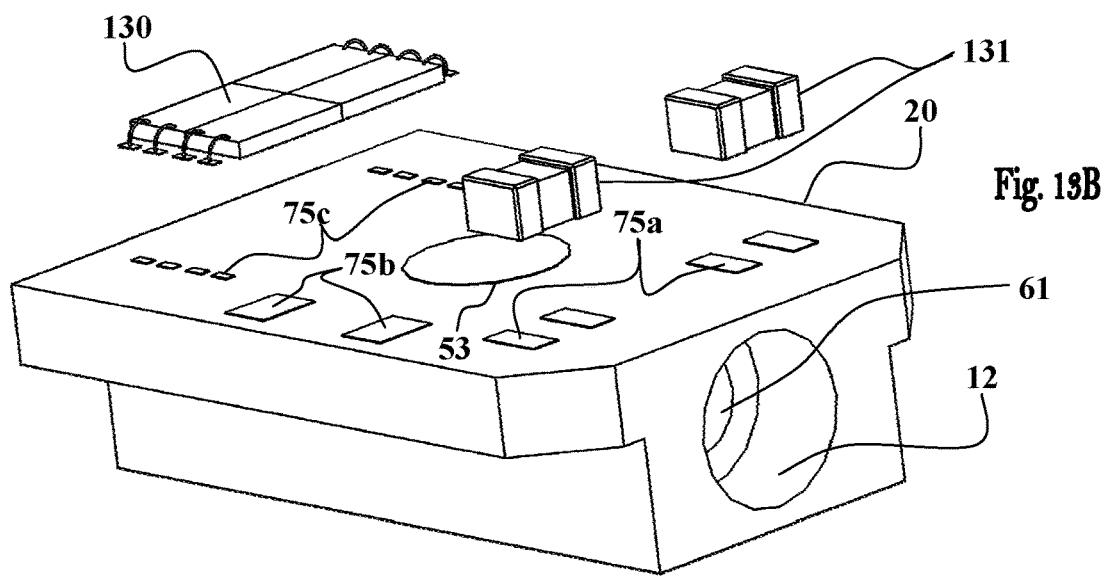
Figure 13C:
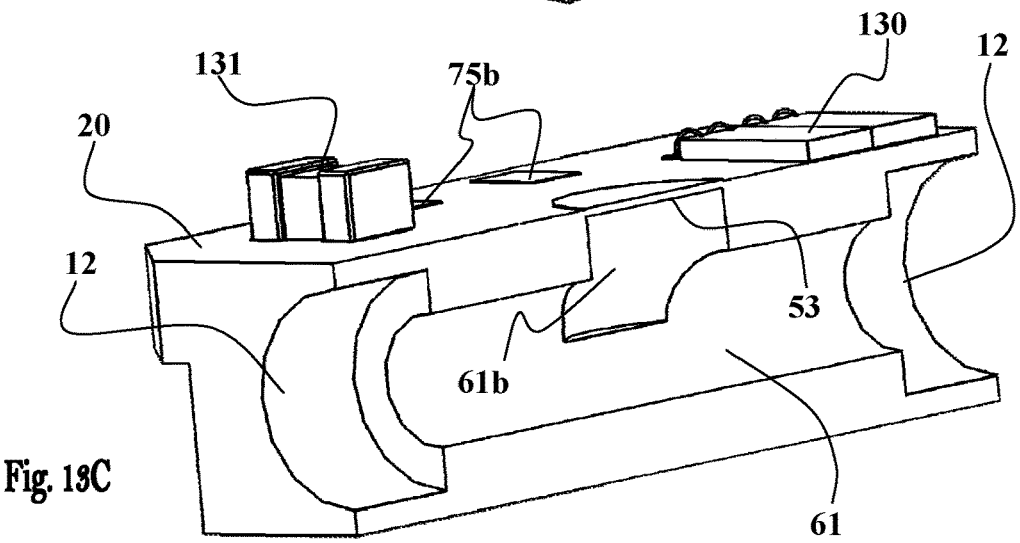

With references to FIGS. 13A to 13C, electronic circuitries (e.g., ASICS) 130 may be mechanically connected (e.g., glued) to the MEM device 20 and electrically connected to respective pads 75c provided on the MEM device 20 e.g., using wire-bonding (the circuitries 130 may be implemented with a power harvesting unit, read-out circuits and/or RF transmitter/receiver). Thereafter, the electronic circuitries 130 may be covered with an insulating layer (e.g., epoxy resin—not shown). In this non-limiting example contact pads 75b provided in MEM device 20 are used to connect a power source (e.g., battery), in case the circuitries 130 is not implemented as a power harvesting unit. Additional electrical/electronic elements 131 may be also electrically connected (e.g., standard SMD components such as resistors, capacitors, integrated RF antenna, etc.) to the MEM device 20 by means of the contact pads 75a provided thereon.

Figure 14A:
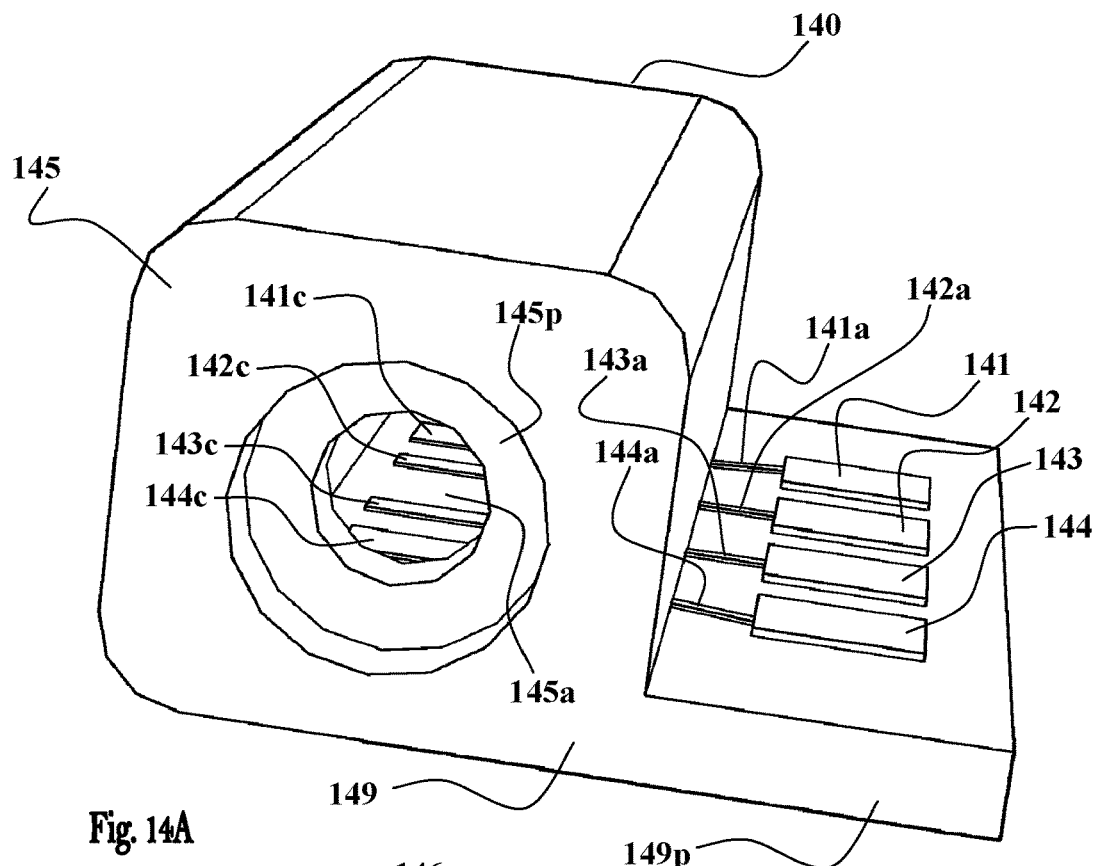
Figure 14B:
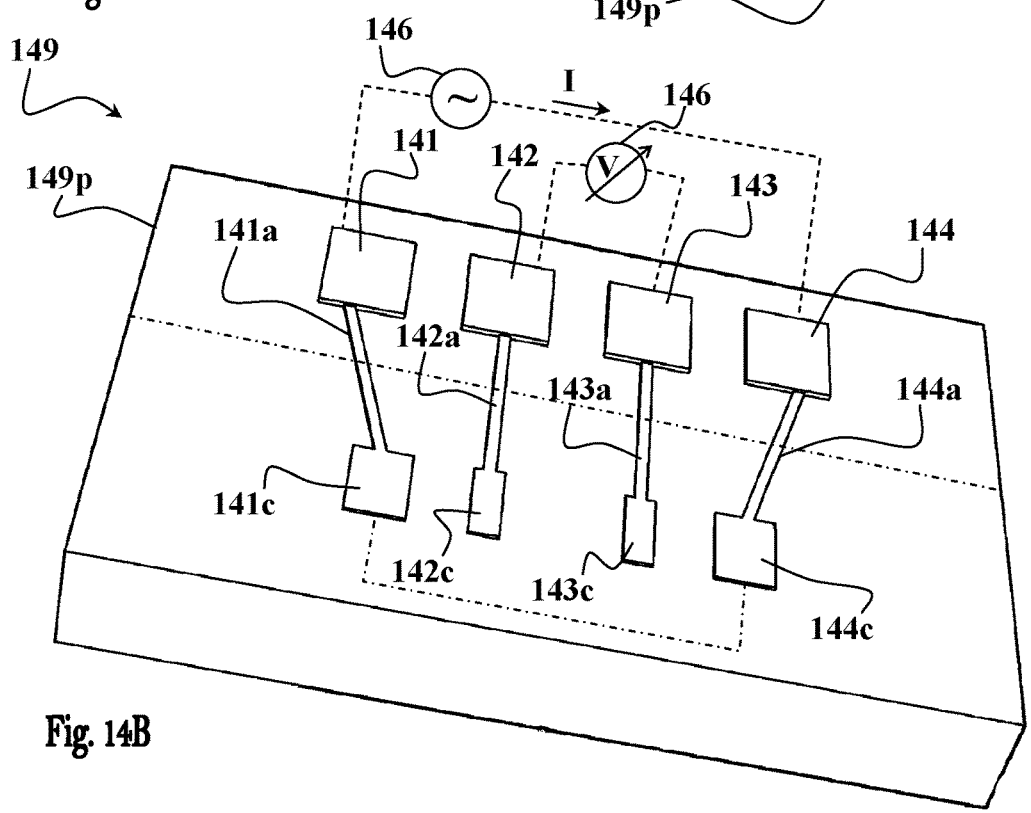

FIGS. 14A and 14B show a MEM device 140 configured according to some possible embodiments to measure electrical conductivity of fluid media. With reference to FIG. 14A, MEM device 140 generally comprises a base plate 149 and a hollow body 145 constructed over a predefined portion of the base plate 149. A fluid channel/chamber 145a provided in the hollow body 145 is accessible for fluid media entry thereinto via a fluid port 145p. In some embodiments the fluid port 145p is used as an inlet, and another fluid port (not shown) provide at the other end of the hollow body 145 is used as an outlet.

A portion 149p of the base plate 149 not occupied by the hollow body 145 is provided with an array of electrical contact pads, each electrically coupled by an electrically conducting line with a respective electrode disposed inside the fluid channel/chamber 145a. In some embodiment two contacts, and two respective electrodes are used for measuring electrical conductivity of the fluid in the channel/chamber 145a. In this non-limiting example four contact pads, 141, 142, 143 and 144, are provided on the uncovered portion 149p of the plate 149, and four conducting lines 141a, 142a, 143a and 144a, are respectively used to connect each contact pad to a respective electrode 141c, 142c, 143c and 144c, inside the chamber/channel 145a. In this configuration the contact pads 141, 142, 143 and 144, are used to connect the MEM device to 140 to an external device (e.g., control unit), and the respective electrode 141c, 142c, 143c and 144c, in direct contact with fluid media in the chamber/channel 145a are used to measure electrical conductivity of the fluid.

Referring now to FIG. 14B showing the base portion/plate 149 of the device 140, without the hollow body 145, the electrical conductivity of the fluid inside the chamber/channel may be measured by applying an alternating current (AC) I between the outer electrodes 144c and 141c (being closer to the lateral sides of the device) and at the same time measuring the electrical voltage V obtained over the inner electrodes 143c and 142c (located between the outer electrodes). The AC current I passing through the fluid (shown by dotted-dashed line) and the measured voltage V can be then used to calculate the electrical conductance G based on the equality G=I/V. The conductivity c can be then calculated based on the cell constant K as follows: c=K*G. The cell constant K depends from geometric parameters of the channel/chamber 145a and of the electrodes, and it can be either calculated or calibrated. Because the conductivity is temperature dependent the temperature sensor can be used from the external control to compensate temperature effects.

Figure 15A:
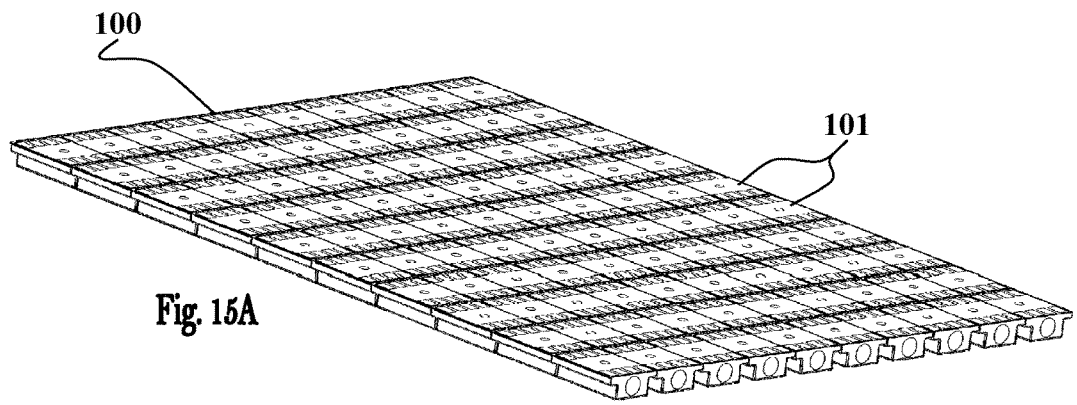
Figure 15B:
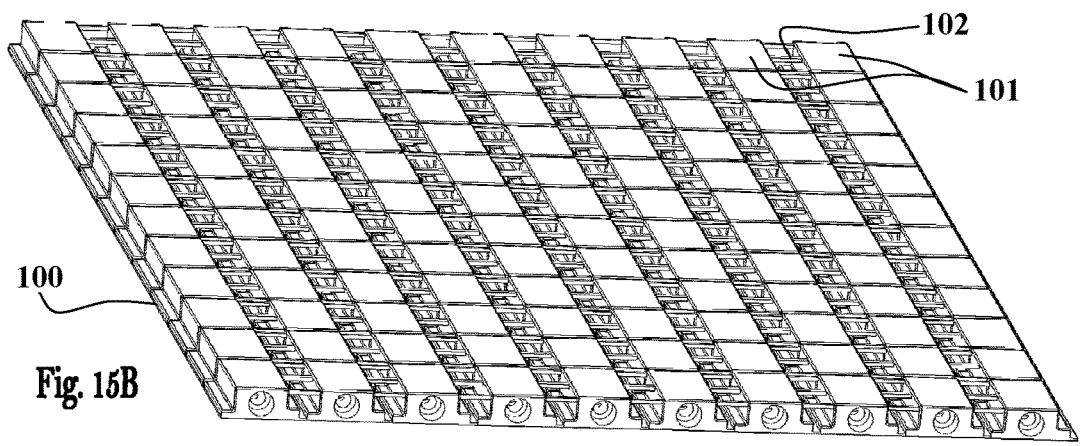

In multilayered MEM device construction approaches exemplified in FIGS. 11A to 11G the attachment (e.g., welding) between the different layers and the base structure can be carried out at die level or at wafer level. FIGS. 15A and 15B demonstrates a possible manufacture of the MEM device in a rectangular wafer 100 comprising an array of dies 101 of the MEM devices. As shown in FIG. 15B, dies of MEM device 101 adjacently located in the wafer 100 may be connected to each other by connecting pins 102 (or by connection layers).

Figure 15C:
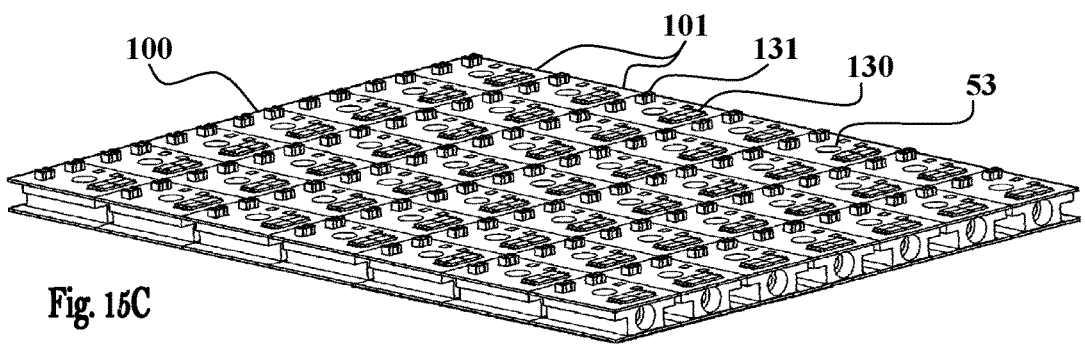

FIG. 15C shows a wafer 100 according to possible embodiments comprising electrical/electronic elements (e.g., SMD) electrically connected to the dies 101 at wafer level. As seen, each die 101 in the wafer 100 comprises a small MEM device serving a PCB with integrated sensing elements and control capabilities and connections to external fluid supply/delivery systems.

Figure 15D:
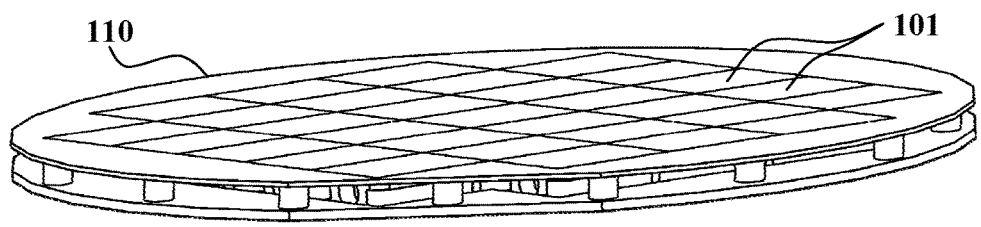
Figure 15E:
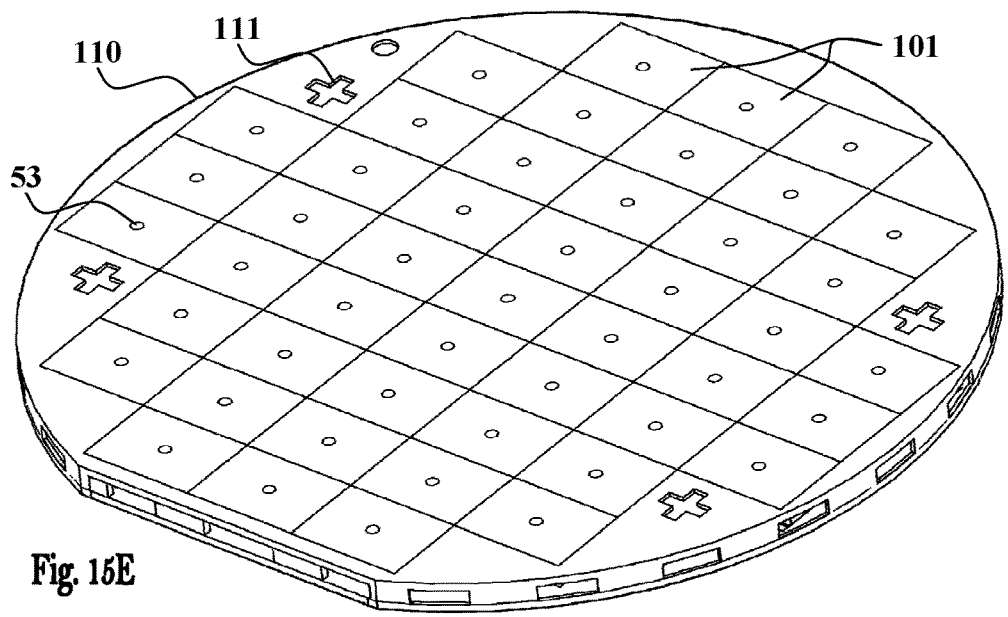

FIGS. 15D and 15E show a circular wafer configuration 110 each comprising an array of dies 101 of the MEM devices. As seen in FIG. 15E, alignment structures 111 may be formed in the wafer 110 for facilitating automated mass production fabrication process.

Figure 15F:
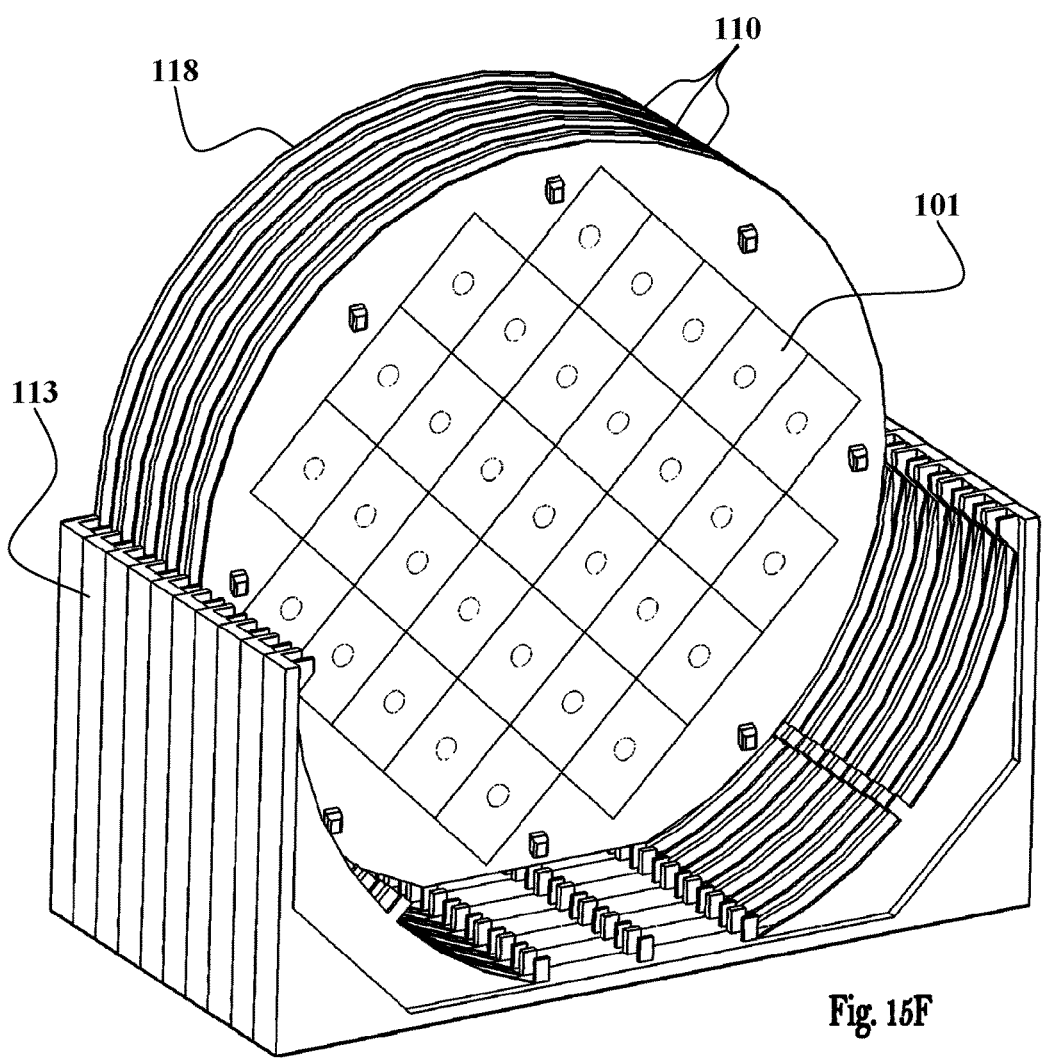

FIG. 15F demonstrates a fabrication technique of a stack 118 of wafers 110, each comprising an array of dies 101 of the MEM devices. The stack 118 is held in a stack holder 113 adapted to receive the wafers in slots. In this non-limiting example, the wafer stack 118 and the holder 113 are built together within the same manufacture process employing any suitable production technique, such as 3D printing. This production technique can thus provide a more efficient and time saving manufacture process. In addition, as the wafer stack 118 and its holder 113 are fabricated as one unit they can be transported easily and without additional staking operations. In some embodiments the stack holder 113 comprises one or more protection layers for the first and last wafers 110 in the stack.

Figure 16A:
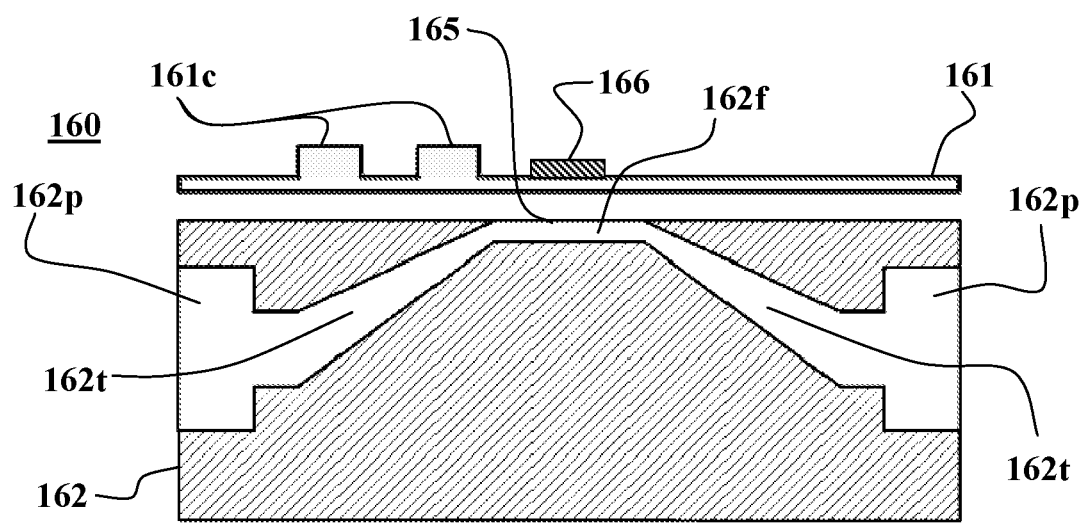

FIG. 16A schematically illustrate a fluidic MEM device 160 according to some possible embodiments. The MEM device 160 comprises a base element 162 having at least one fluid port 162$p$ and at least one cavity or fluid flow path 162$f$ in fluid communication with the at least one fluid port 162$p$ via at least one fluid passage 162$t$, and at least one deformable layer 161 (e.g., thin membrane/film/foil, also referred to herein as encapsulating layer) attached thereto. The base element 162 is structured and arranged with an opening 165 provided in one of its surface areas, said opening 165 being in fluid communication with the at least one cavity or fluid flow path 162$f$ and is sealably closed by the deformable layer 161 attached thereover. In the specific non-limiting example shown in FIG. 16A, the at least one cavity or fluid flow path 162$f$ is formed along a section of the top side surface of the base element 162, and it is in fluid communication with two lateral fluid ports 162$p$ via respective two fluid passages 162$t$ having lumens that taper upwardly towards the at least one cavity or fluid flow path 162$f$. However, lumens of the fluid passages 162$t$ are not essentially having tapering configuration, and indeed in some embodiments the lumens in the MEM device are not tapering, or only slightly/partly tapper.

Numeral 166 designates in FIG. 16A electrical conducting lines, sensing element (e.g., for sensing fluid pressure inside the at least one cavity or fluid flow path 162$f$), and/or actuating means for regulating fluid flow through the at least one cavity or fluid flow path 162$f$, placed on a surface area of the deformable layer 161 located above the at least one cavity or fluid flow path 162$f$, using any of the techniques described hereinabove. Electrical contacts 161$c$ can be also patterned on the deformable layer 161, preferably, but not essentially, on a surface area not affected by its deformations. Accordingly, the MEM device 160 is generally constructed from the two main layers, the base element 160 with its fluid interacting structures, and the deformable layer 161 attached thereover sealing the top opening 165 of the at least one cavity or fluid flow path 162$f$.

In some embodiments, the base element 162 and the deformable layer 161 are made from a same (or different) type of polymeric material, or any other suitable material, as described hereinabove (e.g., lamination, CNC or micro-CNC, 3D printing, micro scale molding, micro machining, nano and micro imprinting, hot embossing, injection molding, lithography, laser micromachining, additive manufacturing, and suchlike).

Figure 16B:
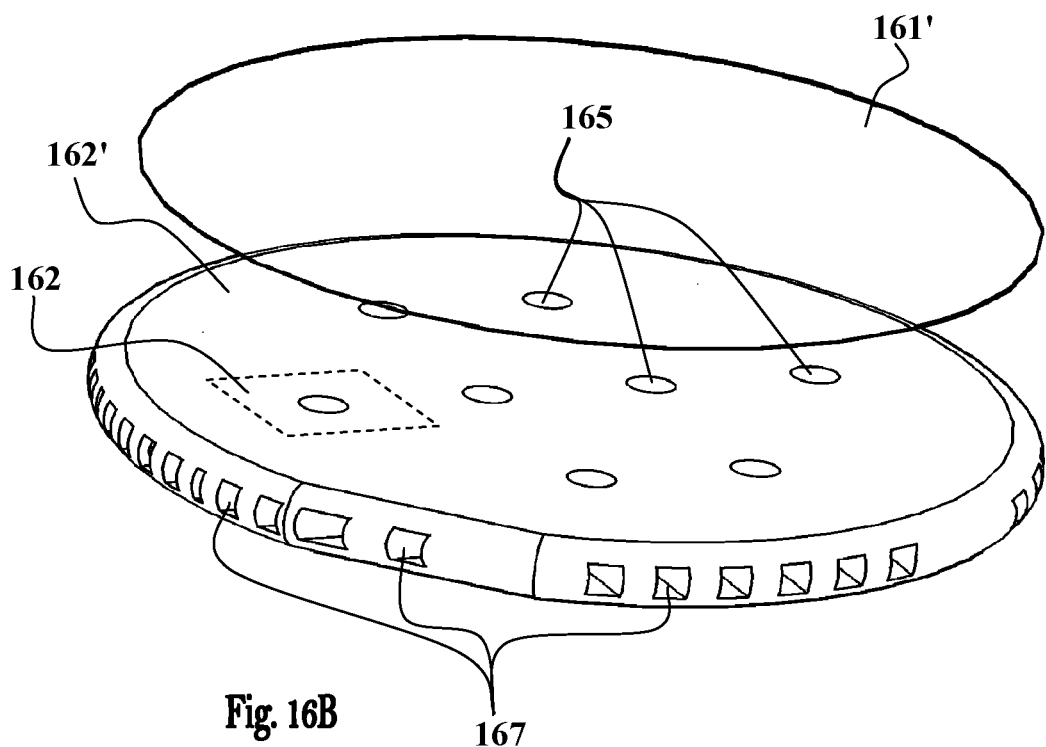

FIG. 16B demonstrates fabrication of a plurality of the fluidic MEM devices 160 according to possible embodiments. The base elements 162 of the MEM devices 160 are fabricated in this non-limiting example as dies in the wafer 162' (also referred to herein as MEM production wafer) structured and arranged to form the inner fluid interacting structures (not shown) of each MEM device 160, in fluid communication with a respective top opening 165 thereof. A common deformable layer 161' is attached (e.g., lamination, ultrasonic welding, bonding, gluing, laser welding) on top of the wafer 161' for sealably closing the top openings of all of the base elements 162 in the wafer 161'. After attaching the deformable layer 161' over the top surface and closing the openings 165, the plurality of MEM device 160 are cut (diced, illustrated by a dashed-line rectangle) out from the obtained layered structure using any known suitable dicing technique.

The electrical contacts (161$c$ in FIG. 16A), and/or the electrical conducting lines, and/or the sensing element, and/or the actuating means (166 in FIG. 16B) can be formed or mounted on the deformable layer before or after cutting out the MEM device 160, using any of the techniques described hereinabove. Optionally, additional circuitries (e.g., a controller, data communication means) are patterned/deposited on the MEM device 160 for handling signals measured by the device and externally received control signals, and for communicating (via the electrical contacts, or wirelessly) these signals with one or more external devices. In some possible embodiments the actuating means placed on the deformable layer are configured to regulate the fluid flow through the at least one cavity or fluid flow path 162$f$ responsive to mechanical or electromagnetic external control e.g., applied by an external device.

The wafer 162' comprises a plurality of lateral openings 167, at least some of which are in fluid communication with its internal fluid interacting structures. As seen, in this specific and non-limiting example, the lateral openings 167 are of rectangular geometrical shape to allow sealing them easily (e.g., using glue, adhesive tape, sealably fitting plugs, and suchlike) to prevent contamination of the inner fluid passages, cavities/flow paths. In possible embodiments the wafer 162' does include the lateral openings 167.

Figure 17A:
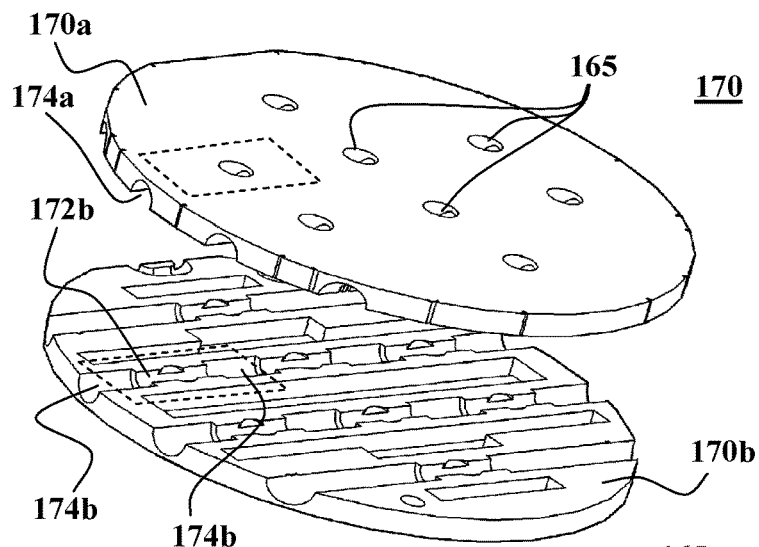
FIGS. 17A and 17B schematically illustrate another possible technique of fabricating a plurality of the fluidic MEM device shown in FIG. 16A according to possible embodiments, wherein FIGS. 17A and 17B respectively show top and bottom perspective views of parts used for assembling a base wafer.
Figure 17B:
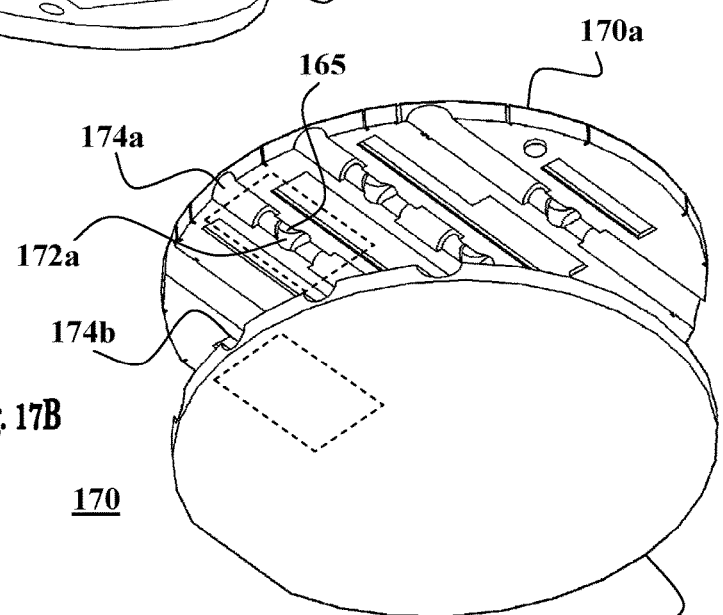
Figure 17C:
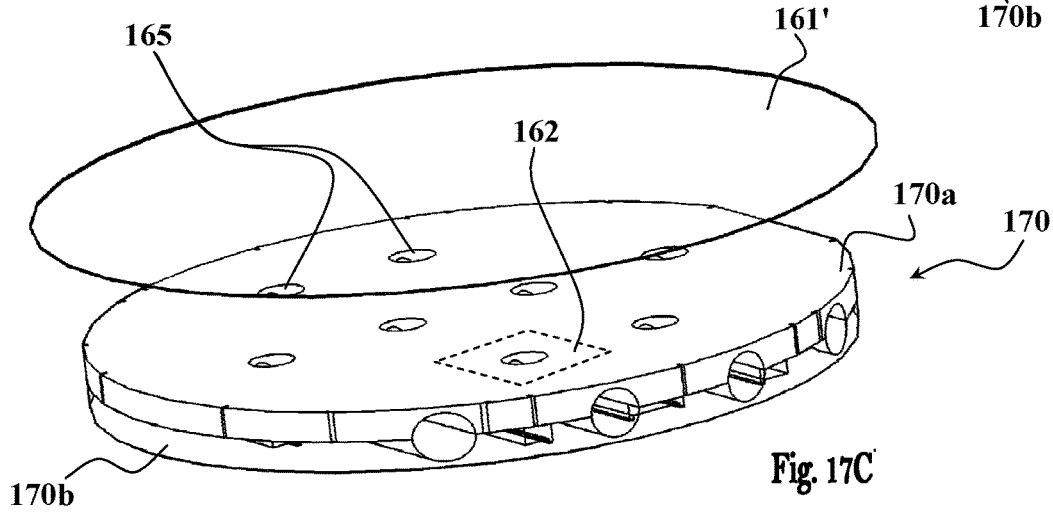
FIG. 17C shows attachment of a membrane to the assembled wafer base.

FIGS. 17A to 17C schematically illustrate another possible technique of fabricating a plurality of the fluidic MEM devices 160 shown in FIG. 16A. As seen in FIGS. 17A and 17B, in this non-limiting example the wafer 170 (also referred to herein as MEM production wafer) is assembled from two layers configured to form the fluid interacting structures of the base elements (162) by sealably attaching one layer to the other. The bottom layer 170$b$ of the wafer 170 is structured and arranged with a fluid port portions 174$b$ and cavity/fluid flow channel portions 172$b$, and the top layer 170$a$ of the wafer 170 is structured and arranged with complementary fluid port portions 174$a$ and cavity/fluid flow channel portions 172$a$, and respective openings 165 in fluid communication with their respective fluid port portions 174$a$.

The top layer 170$a$ can be attached to the bottom layer 170$b$ of the wafer 170 by lamination, ultrasonic welding, bonding, gluing, laser welding. The attachment of the layer 170$a$ and 170$b$ in alignment of their fluid interaction portions sealable construct the fluid ports, fluid passages, and cavities/fluid flow paths of the base elements. For example, and without being limiting, if laser welding is used, the top layer 170$a$ can be a thermoplastic laser adsorbent layer, the bottom layer 170*b* can be a thermoplastic transparent laser layer, and the deformable layer 161' can be a laser transparent.

FIG. 17C shows attachment of a common deformable layer 161' on top of the top layer 170*a* of the assembled wafer 170, sealing the openings 165 of the base elements 162 integrated in it. The deformable layer 161' can be attached on the top layer 170*a* and close its openings 165, using any of the techniques described herein, or any other suitable technique. After attaching the deformable layer 161' over the top surface and closing the openings 165, the plurality of MEM device 160 are cut (diced, illustrated by a dashed-line rectangle) out from the obtained layered structure using any known suitable dicing technique.

In some possible embodiments the top layer 170*a* is structured and arranged to integrally include deformable elements i.e., by fabricating the top layer 170*a* to include elastic/flexible thin regions instead of the opening 165. In this configuration attachment of the common deformable layer 161' on top of the top layer 170*a* is only optional and it can be omitted.

The top and/or bottom layers 170*a* and 170*b*, and/or the deformable layer 161', can be manufactured from polymeric materials (same or different) by any suitable technique, such as described herein. The electrical contacts, and/or the electrical conducting lines, and/or the sensing element, and/or the actuating means, and/or any additional circuitries (e.g., a controller, data communication means), can be mounted on the deformable layer 161' before or after cutting out the MEM device 160, using any of the techniques described herein, or any other suitable technique.

FIGS. 17A to 17C demonstrate aligning the portions of the fluid interacting structures in the layers 170*a* and 170*b* in parallel structures, but of course any other suitable arrangement can be employed instead per implementation and design configuration. In the specific and non-limiting example shown in FIGS. 16B and 17A to 17C the wafer 162' and the deformable layer 161' are of a circular disk shape, and the wafer 162' is structured and arranged to include 8 base elements 162. However, the fabrication technique shown in FIG. 16B of course can used to manufacture wafers comprising any number of MEM devices and having any other suitable shape and dimensions.

The thickness of the deformable layer in some embodiments is in the range of 0.1 to 1000 micrometer, optionally between 20 to 150 micrometer. In possible embodiments at least some of the electrical contacts/patterns, and/or the additional circuitries, and/or the electrical conducting lines, and/or the sensing elements, and/or actuating means, are mounted/deposited on the deformable layer 161' before it is attached to the wafer.

As described hereinabove and shown in the associated Figs., the present invention provides structures and manufacture techniques of fluid MEM device usable for monitoring and regulating flow of a fluid media. While particular embodiments of the invention have been described, it will be understood, however, that the invention is not limited thereto, since modifications may be made by those skilled in the art, particularly in light of the foregoing teachings. As will be appreciated by the skilled person, the invention can be carried out in a great variety of ways, employing more than one technique from those described above, all without exceeding the scope of the invention.

What is claimed:

1. A device for monitoring fluid media, said device comprising:
a base element having at least one fluid port and at least one cavity or fluid flow path fluidly coupled to said at least one fluid port for enabling fluid exchange of fluid media therewith, said base element being a monolithic unit made from a single type of material;
at least one deformable element associated with the at least one cavity or fluid flow path and configured and operable to elastically deform responsive to pressure conditions inside said at least one cavity or fluid flow path;
at least one sensing element associated with said at least one cavity or fluid flow path and comprising at least one transducing element on at least one side of the at least one deformable element and configured and operable for measuring at least one property or condition of fluid media introduced thereinto and generating measurement data or signals indicative thereof; and
electrical elements disposed on said device and electrically coupled to said at least one sensing element.

2. The device according to claim 1 wherein the sensing element comprises two or more electrodes in fluid communication with the at least one cavity or fluid flow path said two or more electrodes being configured and operable to carry out at least one of the following: measure electrical conductivity of the fluid media introduced into the at least one cavity or fluid flow path; and flow by a first pair of spaced apart electrodes a predefined electrical current through the at least one cavity or fluid flow path when filled with the fluid media, and measure by a second pair of spaced apart electrodes an electrical voltage induced by said predefined electrical current.

3. The device of claim 1 wherein the at least one deformable element comprises actuating means coupled thereto and structured and arranged to controllably deform said at least one deformable element to thereby regulate fluid passage through said at least one cavity or fluid flow path.

4. The device of claim 1 comprising at least one deformable element having actuating means structured and arranged to controllably deform said at least one deformable element to thereby regulate fluid passage through the at least one cavity or fluid flow path responsive to external mechanical, electromagnetic, or electromechanical control.

5. The device of claim 1 comprising a constriction in a section of the fluid flow path, and wherein at least one deformable element of the device having at least one sensing element disposed on it is associated with a section including said constriction and being configured and operable to elastically deform responsive to pressure conditions thereinside.

6. The device of claim 5 comprising at least one deformable element in a section of the fluid flow path not including the constriction.

7. The device of claim 5 comprising at least one deformable element coupled to the section of the fluid flow path comprising the constriction, and actuating means coupled to said at least one deformable element and structured and arranged to controllably deform said at least one deformable element to thereby regulate fluid passage through the constriction.

8. A device for monitoring fluid media, said device comprising:
a base element having at least one fluid port and at least one cavity or fluid flow path fluidly coupled to said at least one fluid port for enabling fluid exchange of fluid media therewith;
at least one sensing element associated with said at least one cavity or fluid flow path and configured and operable for measuring at least one property or condition of fluid media introduced thereinto and generating measurement data or signals indicative thereof;

electrical elements disposed on said device and electrically coupled to said at least one sensing element; and at least one transducing element disposed on a surface area of the base element, or on at least one deformable element, of the device not affected by the deformations of the at least one deformable element.

9. The device of claim 8 wherein at least one of the transducing elements disposed on a surface area of the base element, or on the at least one deformable element, not affected by the deformations of the at least one deformable element is used as a temperature sensor.

10. The device of claim 8 wherein the transducing elements are configured and operable to implement Wheatstone bridge circuitry.

11. The device of claim 1 comprising at least one electrical circuitry mounted on the base element, or on at least one deformable element, of the device and electrically coupled to one or more of the electrical elements.

12. The device of claim 11 wherein the electrical circuitry comprises a control unit configured and operable to carry out at least one of the following: receive and process the measurement data generated by the at least one sensing element and generate corresponding control signals for regulating flow of the fluid media; transfer to an external device the measurement data generated by the at least one sensing element via the one or more electrical elements, or wirelessly; receive control signals from an external device via the one or more electrical elements, or wirelessly.

13. A device for monitoring fluid media, said device comprising:

a base element having at least one fluid port and at least one cavity or fluid flow path fluidly coupled to said at least one fluid port for enabling fluid exchange of fluid media therewith;

a layered structure formed on the base element and comprises at least one encapsulating layer structured and arranged to sealably form at least one deformable element over the at least one cavity or fluid flow path to thereby enable the at least one deformable element to interact with fluid media when introduced into said at least one cavity or fluid flow path;

at least one sensing element associated with said at least one cavity or fluid flow path and comprising at least one transducing element on at least one side of the at least one deformable element and configured and operable for measuring at least one property or condition of fluid media introduced thereinto and generating measurement data or signals indicative thereof; and electrical elements disposed on said device and electrically coupled to said at least one sensing element.

14. The device of claim 13 comprising at least one of the following layers: a fluid path layer structured and arranged to sealably connect to the base element and form the at least one cavity or fluid flow path; and an intermediate layer disposed between the fluid path and encapsulating layers and comprising at least one slot, each slot being aligned with a deformable element of the encapsulating layer and configured to receive fluid media from the at least one cavity or fluid flow path of the flow path layer.

15. The device of claim 1 wherein the device has a layered structure formed on the base element, and said base element being structured and arranged to form the at least one deformable element, and wherein the device comprises:

a transition layer, having at least one fluid passage, each fluid passage being associated with a respective fluid port of the base element, and at least one slot, each slot being associated with a deformable element of the base element, said transition layer structured and arranged to sealably connect to the base element and fluidly communicate each fluid passage with its respective fluid port and align each slot with its respective deformable element; and an encapsulating layer having the at least one cavity or fluid flow path and structured and arranged to sealably connect to the transition layer and fluidly communicate between the at least one cavity or fluid flow path of the base element and the at least one fluid passage of the transition layer, thereby enabling passage of fluid media into the at least one cavity or fluid flow path from the at least one fluid port in the base element via a respective fluid passage in the transition layer, and align the at least one cavity or fluid flow path with the at least one slot, to thereby enable each deformable element to interact with fluid media introduced into its respective slot via the respective cavity or fluid flow path.

16. The device of claim 15 comprising a fluid flow path in the encapsulating layer, said fluid flow path having a constriction, and wherein at least one slot of the transition layer is in fluid communication with said constriction to enable its respective deformable element to interact with fluid media introduced thereinto, and at least one other slot is in fluid communication with a non-constricted section of the fluid flow path to enable its respective deformable element to interact with fluid media introduced thereinto.

17. The device of claim 16 comprising a fluid passage in the base element communicating between constricted and non-constricted regions of the fluid flow path, said fluid passage comprising at least one deformable element configured and operable to an elastically deform responsive to pressure differences between said constricted and non-constricted regions of the fluid flow path, said at least one deformable element having a transducing element configured and operable to generate measurement data or signals responsive to said deformations.

18. The device of claim 15 wherein the encapsulating layer comprises at least one elastically deformable element having a flow regulating element configured and operable to engage a fluid passage of the transition layer to thereby alter fluid passage therethrough.

19. The device of claim 15 having at least one transduction element on the encapsulating layer.

20. A device for monitoring fluid media, said device comprising:

a base element having at least one fluid port and at least one cavity or fluid flow path fluidly coupled to said at least one fluid port for enabling fluid exchange of fluid media therewith;

at least one sensing element associated with said at least one cavity or fluid flow path and configured and operable for measuring at least one property or condition of fluid media introduced thereinto and generating measurement data or signals indicative thereof; and electrical elements disposed on said device and electrically coupled to said at least one sensing element, said device being configured and operable for mounting on a PCB while establishing electrical contact with at least some of the electrical elements of the device, said PCB comprises a cavity, and at least one deformable element of the device being adapted to deform towards or away said cavity of the PCB.

21. The device of claim 13 wherein the base element is made from two or more layers structured and arranged to construct the at least one cavity or fluid flow path and the at least one fluid port of the base element by their attachment one to the other.

22. The device of claim 1 comprising quick connection means configured and operable to secure the device to an external device while establishing electrical connectivity, and sealable fluid communication, therewith.

23. A fluid delivery system comprising: at least one monitoring device according to claim 1, and quick connection means configured and operable to secure said monitoring device to an external device while establishing at least one of electrical connectivity and sealable fluid communication, therewith, said monitoring device being configured for at least one of transferring to an external device the measurement data generated by the at least one sensing element via the one or more electrical elements, or wirelessly, and receiving control signals from an external device via the one or more electrical elements, or wirelessly.

24. The system of claim 23 wherein the fluidic MEM device is configured to regulate fluid flow through the at least one cavity or fluid flow path by actuating means mechanically, electromechanically, or electromagnetically controlled by the external device.

25. A method of constructing a fluidic MEM device for monitoring fluid media according to claim 1, the method comprising:
constructing from a specific single type of material the base element comprising the at least one fluid port and the at least one cavity or the fluid flow path in fluid communication with the at least one fluid port for enabling exchange of the fluid media therewith, the base element being the monolithic unit made from the single type of material;
forming at least one deformable element associated with the at least one cavity or fluid flow path, said at least one deformable element being structured and arranged to elastically deform responsive to pressure conditions inside said at least one cavity or fluid flow path;
constructing the at least one sensing element associated with said at least one cavity or fluid flow path of the device at least partially on the deformable element for measuring the at least one property or condition of the fluid media introduced thereinto, and for generating the measurement data or signals indicative thereof; and
forming on said device the electrical elements disposed on the base element of the device and electrically coupled to said at least one sensing element.

26. The method of claim 25 comprising forming on the at least one deformable element electrically conducting patterns of the at least one transducing element.

27. The method of claim 25 wherein the constructing of the base structure comprises forming a constriction in a section of the at least one cavity or fluid flow path and forming at least one elastically deformable element associated with said constriction, and wherein at least one of the deformable elements associated with said section comprising the constriction comprises a sensing element for measuring fluid pressure conditions in said section comprising the constriction, or being mechanically coupled to an actuator for altering fluid passage through said section comprising the constriction.

28. The method of claim 25 comprising: constructing an encapsulating layer structured and arranged to form at least one elastically deformable element; applying electrically conducting patterns of the transducing element on the encapsulating layer, coupling the at least one sensing element to at least one deformable element; and sealably attaching the encapsulating layer to the base structure.

29. The method of claim 25 comprising:
constructing a flow path layer comprising the at least one cavity or fluid flow path;
constructing an intermediate layer comprising at least one slot;
constructing an encapsulating layer comprising at least one elastically deformable element,
constructing the at least one sensing element associated with at least one deformable element on the encapsulating layer;
assembling a layered structure by sealably attaching the encapsulating layer to the intermediate layer such that at least one element of the encapsulating layer is disposed over at least one slot of the intermediate layer, and sealably attaching the intermediate layer to the flow path layer such that fluid communication is established between at least one slot of the intermediate layer and the at least one cavity or fluid flow path of the flow path layer; and
sealably attaching the layered assembly to the base structure such that fluid communication is established between the at least one fluid port of the base structure and the at least one cavity or fluid flow path of the flow path layer.

30. The method of claim 25 wherein constructing of the base structure comprises forming at least one deformable element in the base structure, and wherein the at least one sensing element is associated with said at least one deformable element.

31. The method of claim 25 wherein constructing of the base structure comprises forming at least one deformable element in the base structure, the at least one sensing element is associated with said at least one deformable element, the method further comprising:
constructing a transition layer having at least one fluid passage and at least one slot formed therein;
constructing an encapsulating layer having at least one cavity or fluid flow path or at least one elastically deformable element having a flow regulating element;
assembling a layered structure by sealably attaching the encapsulating layer to the transition layer such that fluid communication is established between the at least one cavity or fluid flow path of the encapsulating layer and at least one fluid passage and at least one slot of the transition layer; and
sealably attaching the layered assembly to the base structure such that fluid communication is established between at least one slot of the transition layer and at least one fluid port of the base structure, at least one slot of the transition layer is positioned over at least one deformable element of the base structure.

32. The method of claims 31 wherein the constructing of the encapsulation layer comprises at least one of the following steps: forming a constriction in a section of the fluid flow path, and wherein the assembling of the layered structure comprises establishing fluid communication between the section comprising said constriction of the encapsulating layer and at least one slot of the transition layer, said at least one slot being associated with one of the deformable elements in the base structure; and forming a fluid passage in the base structure for communicating between constricted and non-constricted sections of the fluid flow path via respective slots of the transition layer, said fluid passage comprising at least one deformable element configured and operable to elastically deform responsive to pressure differences between said constricted and non-constricted regions of the fluid flow path, said deformable element having a transducing element configured and operable to generate measurement data or signals responsive to said deformations.

33. The method of claim 28 comprising constructing a flow path layer comprising the at least one cavity or fluid flow path, sealably attaching the encapsulating layer to the flow path layer such that at least one deformable element of the encapsulating layer is disposed over the at least one cavity or fluid flow path of the flow path layer, and sealably attaching the flow path layer to the base structure such that fluid communication is established between the at least one fluid port of the base structure and the at least one cavity or fluid flow path of the flow path layer.

34. The method of claim 28 comprising constructing the base element, and its at least one fluid port and at least one cavity or a fluid flow path, by sealably attaching first and second parts one to the other, said first and second parts are structured and arranged to form said at least one fluid port and at least one cavity or a fluid flow path by their attachment one to the other.

35. The method of claims 25 wherein the base structure, or layers of the device, are made from a polymeric material, and wherein electrically conducting patterns of the device are made by deposition of conductive material on the polymeric material.

36. The method of claim 25 wherein forming at least one of the base structure and one or more of the sealably attached layers, utilizes one of the following techniques: injection molding, lamination, CNC or micro-CNC, 3D printing, micro scale molding, micro machining, nano imprinting, micro imprinting, hot embossing, additive manufacturing, lithography, and laser micromachining.

37. The method of claims 25 comprising one of the following steps: manufacturing an array of the fluidic MEM devices as dies of a wafer in a mass production process; manufacturing an array of the flow control devices as dies of a wafer in a mass production process wherein at least one face of the wafer is arranged for forming and/or mounting the electrically conducting patterns thereon, while keeping the wafer mechanically prepared for wafer dicing; and manufacturing an array of the flow control devices as dies of a wafer in a mass production process, and manufacturing in the mass production process a wafer stack comprising a plurality of said wafers stack one on top of the other.

38. The method of claim 37 comprising sealing the wafer.

39. A wafer comprising a plurality of dies, each die comprising a monitoring device according to claim 1.

40. The wafer of claim 39 comprising a plurality of lateral openings, at least some of said lateral openings being in fluid communication with the at least one cavity or fluid flow path of the dies, said plurality of lateral openings structured and arranged to facilitate sealing said at least one cavity or fluid flow path to prevent contamination of the internal flow paths or cavities during fabrication.

* * * * *